US011773177B2

(12) United States Patent
Kim

(10) Patent No.: US 11,773,177 B2
(45) Date of Patent: Oct. 3, 2023

(54) VARIANT ANTIBODIES THAT BIND OX40

(71) Applicant: Sorrento Therapeutics, Inc., San Diego, CA (US)

(72) Inventor: Min Soo Kim, San Diego, CA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 213 days.

(21) Appl. No.: 17/409,595

(22) Filed: Aug. 23, 2021

(65) Prior Publication Data

US 2021/0395380 A1    Dec. 23, 2021

Related U.S. Application Data

(63) Continuation of application No. 16/212,349, filed on Dec. 6, 2018, now Pat. No. 11,142,579.

(60) Provisional application No. 62/595,564, filed on Dec. 6, 2017.

(51) Int. Cl.
| | |
|---|---|
| A61K 39/00 | (2006.01) |
| A61K 39/395 | (2006.01) |
| C07K 16/00 | (2006.01) |
| C07K 16/46 | (2006.01) |
| G01N 33/53 | (2006.01) |
| C07K 16/28 | (2006.01) |
| G01N 33/50 | (2006.01) |

(52) U.S. Cl.
CPC ....... *C07K 16/2878* (2013.01); *G01N 33/505* (2013.01); *C07K 2317/21* (2013.01); *C07K 2317/33* (2013.01); *C07K 2317/565* (2013.01); *C07K 2317/74* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,960,515 B2 | 6/2011 | Min et al. | |
| 8,748,585 B2 | 6/2014 | Attinger et al. | |
| 9,163,085 B2 | 10/2015 | Liu et al. | |
| 11,142,579 B2 * | 10/2021 | Kim | C07K 16/2878 |
| 2005/0049402 A1 | 3/2005 | Babcook et al. | |
| 2008/0233133 A1 | 9/2008 | Watkins et al. | |
| 2010/0254982 A1 | 10/2010 | Glover et al. | |
| 2014/0004121 A1 | 1/2014 | Fanslow, III et al. | |
| 2016/0200799 A1 | 7/2016 | Kurosawa et al. | |

FOREIGN PATENT DOCUMENTS

| | | |
|---|---|---|
| WO | 9942585 A1 | 8/1999 |
| WO | 2015153513 A1 | 10/2015 |
| WO | 2018031490 A2 | 2/2018 |

OTHER PUBLICATIONS

Weinberg et al., 2000 J Immunol 164:2160-2169 Engagement of the OX-40 Receptor In Vivo Enhances Antitumor Immunity.
Weinberg et al. 2006 Journal of Immunotherapy 29: 575-585 Anti-OX40 (CD134) Administration to Nonhuman Primates: Immunostimulatory Effects and Toxicokinetic Study.
International Search Report relating to application No. PCT/US2017/045788, completed Dec. 10, 2017, dated Jan. 29, 2018.
Written Opinion relating to application No. PCT/US2017/045788, completed Dec. 10, 2017, dated Jan. 29, 2018.

* cited by examiner

*Primary Examiner* — Maher M Haddad

(74) *Attorney, Agent, or Firm* — BAKER BOTTS L.L.P.

(57) ABSTRACT

The present disclosure provides variant anti-OX40 antibodies that mimic the activity of OX40L by behaving as an agonist against receptor OX40 to enhance T cell clonal expansion and differentiation. The variant anti-OX40 antibodies exhibit improved binding affinity for OX40 and improved agnostic activity, compared to a wild type anti-OX40 antibody (wild type 2B4 clone) from which the variant clones are derived. The variant anti-OX40 antibodies specifically bind OX40 receptors on activated T lymphocytes, stimulate proliferation of effector T cells, stimulate proliferation of effector T cells in the presence of regulatory T cells, and stimulate production of at least one cytokine from effector T cells.

19 Claims, 37 Drawing Sheets
Specification includes a Sequence Listing.

| Clone | ka (1/Ms) | kd (1/s) | KD (M) | Rmax (RU) | Chi$^2$(RU$^2$) |
|---|---|---|---|---|---|
| 2-B4 WT | 1.13E+05 | 0.03752 | 3.32E-07 | 65.63 | 0.884 |
| 5-A6 | 1.23E+05 | 2.96E-4 | 2.41E-09 | 142.9 | 0.838 |
| 5-A8 | 1.12E+05 | 4.91E-04 | 4.37E-09 | 142.9 | 3.33 |
| 5-C8 | 9.73E+04 | 4.27E-04 | 4.39E-09 | 58.61 | 3.82 |
| 5-F5 | 1.06+05 | 3.18E-04 | 3.01E-09 | 145.2 | 1.07 |
| 5-G8 | 1.10E+05 | 4.18E-04 | 3.80E-09 | 141.7 | 3.6 |
| 5-H6 | 1.12E+05 | 3.94E-04 | 3.51E-09 | 148.7 | 3.73 |

Fig. 2H

| Name | ka (1/Ms) | kd (1/s) | Rmax (RU) | KD (M) | Chi2 |
|---|---|---|---|---|---|
| MOXR0916/RG7888 | 1.09E5 | 3.49E-4 | 198.2 | 3.2E-9 | 0.88 |

Fig. 2J

VARIANT ANTIBODIES THAT BIND OX40

This application is a continuation of U.S. patent application Ser. No. 16/212,349 filed Dec. 6, 2018, which claims the benefit of priority under 35 U.S.C. § 119 to U.S. provisional application No. 62/595,564, filed Dec. 6, 2017, and entitled "Improved Variant Antibodies that Bind OX40", the contents of which are incorporated by reference herein in their entirety.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

SEQUENCE LISTING

The instant application contains a Sequence Listing which has been filed electronically in ASCII format and is hereby incorporated by reference in its entirety. Said ASCII copy, created on Dec. 5, 2018, is named SL_S103014_2080US1.txt and is 12,577 bytes in size.

TECHNICAL FIELD

The present disclosure provides anti-OX40 IgG class antibodies that have an improved binding capability from their original wild type sequence and an ability to be manufactured at higher yields. More specifically, the present disclosure provides human antibodies that bind OX40, OX40-binding fragments and derivatives of such antibodies, and OX40-binding polypeptides comprising such fragments.

BACKGROUND

OX40 (also known as CD 134, TNFRSF4, ACT35 or TXGP1L) is a member of the TNF receptor superfamily, which includes 4-1BB, CD27, CD30 and CD40. The extracellular ligand binding domain of OX40 is composed of 3 full cysteine-rich domains (CRDs) and a partial, fourth C-terminal CRD (Bodmer et al, 2002, *Trends Biochem. Sci.*, 27, 19-26). The ligand for OX40, OX40L, is a member of the TNF family and is expressed on activated antigen presenting cells (APC), including B cells, macrophages, endothelial cells and dendritic cells (DC). OX40 is a membrane-bound receptor, However, a soluble isoform has also been detected (Taylor and Schwarz, 2001, *J. Immunol. Methods*, 255, 67-72). OX40 is not expressed on resting T cells, but is transiently expressed on activated T cells after ligation of the T cell receptor (TCR).

OX40 is a major costimulatory receptor with sequential engagement of CD28 and OX40 resulting in optimal T cell proliferation and survival. Ligation of OX40 on activated T cells leads to enhanced cytokine production and proliferation of both CD4+ and CD8+ T cells (Gramaglia et al., 2000, *J. Immunol*, 165, 3043-3050, Bansal-Pakala et al., 2004, *J. Immunol.*, 172, 4821-425) and can contribute to both ongoing Th1 and Th2 responses (Gramaglia et al., 1998, *J. Immunol.*, 161, 6510-6517, Arestides et al., 2002, *Eur. J. Immunol.* 32, 2874-2880). OX40 costimulation prolongs T cell survival beyond the initial effector phase of the immune response and increases the number of memory T cells through inhibition of effector T cell death.

When immune activation is excessive or uncontrolled, pathological allergy, asthma, inflammation, autoimmune and other related diseases may occur.

Tumor cells commonly 'escape' the immune system by induction of an active immune tolerance largely mediated by regulatory T lymphocytes (Tregs et al. *Immunol. Rev.* 2011; 241:104-118). Therefore, the balance between effector (i.e., direct or indirect eradication of tumor cells) T lymphocytes (Teffs) and tolerogenic (i.e., suppression of Teffs effector function and survival) Tregs appears to be important for effective anti-tumor immunotherapy. In other words, an effective anti-tumor immune response can be obtained by enhancing effector function of tumor-specific Teffs and/or by attenuating suppressive function of tumor-specific Tregs. A key receptor that has been shown to mediate these responses is OX40 (CD134). (Sugamura et al., *Nature Rev. Imm.* 2004; 4: 420-431).

In vivo ligation of mouse CD134 receptor (by either soluble mouse OX40 ligand (OX40L)-immunoglobulin fusion proteins or mouse OX40L mimetics, such as anti-mouse CD134-specific antibodies) in tumor-bearing mice enhances anti-tumor immunity, leads to tumor-free survival in mouse models of various murine malignant tumor cell lines, e.g., lymphoma, melanoma, sarcoma, colon cancer, breast cancer, and glioma (Sugamura et al. *Nature Rev. Imm.* 2004; 4:420631). Al-Shamkhani et al. (*Eur. J. Chem.* 1996; 26: 1695-1699) used an anti-OX40 antibody called OX86, which did not block OX40L-binding, in order to explore differential expression of OX40 on activated mouse T-cells; and Hirschhorn-Cymerman et al. (*J. Exp. Med.* 2009; 206: 1103-1116) used OX86 together with cyclophosphamide in a mouse model as a potential chemoimmunotherapy.

Thus, there remains a need in the art for effective treatments based on OX40, particularly anti-OX40 antibodies. The present disclosure provides improved variant antibody sequences compared to its parent fully human wild type sequence.

SUMMARY

The present disclosure found that an antibody (called 2B4) disclosed in U.S. Patent application 62/371,993 filed 8 Aug. 2016 and in PCT/US2017/045788 filed 7 Aug. 2017 (the disclosure of which is incorporated by reference herein) as wild type SEQ ID NO. 24 for the heavy chain and SEQ ID NO. 25 for the light chain for more favorable binding characteristics when modified in both its heavy chain and light chain sequences. The same 2B4 wild type sequences are provided herein as SEQ ID No. 1 for the heavy chain and SEQ ID NO. 2 for the light chain. Therefore, the present disclosure provides a fully human antibody of an IgG class that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

The present disclosure provides a Fab fully human antibody fragment that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

The present disclosure provides a single chain human antibody that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

The present disclosure provides fully a human antibody of an IgG class that binds OX40, or an antigen binding portion thereof, comprising a heavy chain variable domain sequence that is at least 95% identical to the amino acid sequences of SEQ ID NO. 9, and at least 95% identical to a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, fully human anti-OX40 antibodies comprise a heavy chain variable domain that is at least 95% identical to, at least 96% identical to, at least 97% identical to, at least 98% identical to, or at least 99% identical to the amino acid sequence of SEQ ID NO:9. In one embodiment, fully human anti-OX40 antibodies comprise a light chain variable domain that is at least 95% identical to, at least 96% identical to, at least 97% identical to, at least 98% identical to, or at least 99% identical to the amino acid sequence of a group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

In one embodiment, the fully human antibodies a heavy chain/light chain set selected from a group consisting of SEQ ID NO:9/SEQ ID NO:3, SEQ ID NO:9/SEQ ID NO:4, SEQ ID NO:9/SEQ ID NO:5, SEQ ID NO:9/SEQ ID NO:6, SEQ ID NO:9/SEQ ID NO:7, and SEQ ID NO:9/SEQ ID NO:8.

In one embodiment, fully human anti-OX40 antibodies comprise an antigen binding protein that binds OX40, wherein the antigen binding protein comprises a heavy chain variable domain comprising CDRs as set forth in the amino acid sequence of SEQ ID NO:9 and comprises a light chain variable domain comprising CDRs as set forth in the amino acid sequence and selected from a group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

In one embodiment, the fully human antibody binds human OX40. In one embodiment, the fully human antibody binds cynomolgus OX40. In one embodiment, the fully human antibody binds rat and/or mouse OX40, or does not bind rat and/or mouse OX40.

In one embodiment, the fully human antibody binds human OX40 and exhibits a $K_d$ of less than $1 \times 10^{-8}$ M.

In one embodiment, the fully human antibody exhibits OX40 agonist activity. In one embodiment, the fully human antibody induces proliferation of effector T cells (e.g., CD4+ effector T cells). In one embodiment, the fully human antibody induces effector T cells (e.g., CD4+ effector T cells) to increase production of at least one cytokine selected from a group consisting of gamma-interferon, IL-2, IL-4 and tumor necrosis factor (TNF). In one embodiment, the fully human antibody induces proliferation of effector T cells (e.g., CD8+ effector T cells). In one embodiment, the fully human antibody inhibits regulatory T cell function, for example inhibits suppressive function of regulatory T cells. In one embodiment, the fully human antibody induces proliferation of effector T cells (Teff) in the presence of regulatory T cells (Treg).

In one embodiment, the fully human antibody induces OX40-mediated signal transduction in an OX40-expressing target cell. For example, OX40-mediated signal transduction can be monitored using transgenic cells that express OX40 and a reporter gene fused to an NFkB promoter, where contacting the transgenic cells with a variant anti-OX40 antibody induces increased NFkB transcription which is detectable using an assay for the reporter gene. In one embodiment, the reporter gene comprises luciferase.

One embodiment comprises a nucleic acid encoding the heavy chain variable domain sequence that is at least 95% identical to the amino acid sequences of SEQ ID NO. 9. One embodiment comprises a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

One embodiment comprises a vector comprising a nucleic acid encoding the heavy chain variable domain sequence that is at least 95% identical to the amino acid sequences of SEQ ID NO. 9. One embodiment comprises a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

One embodiment comprises a host cell harboring a vector comprising a nucleic acid encoding the heavy chain variable domain sequence that is at least 95% identical to the amino acid sequences of SEQ ID NO. 9. One embodiment comprises a host cell harboring a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the host cell is transfected or transformed with the vector comprising the nucleic acid.

One embodiment comprises a pharmaceutical composition, comprising: (a) a fully a human antibody of an IgG class that binds OX40, comprising a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein); and (b) a pharmaceutically acceptable carrier, diluent or excipient.

The present disclosure provides a Fab fully human antibody fragment that binds OX40, or an antigen binding portion thereof, which has a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO.

6 called 5-F5 herein SEQ ID NO. 7 (called 5-G8 herein), and SEQ ID NO. 8 (called 5-H6 herein). In one embodiment, Fab fully human anti-OX40 antibodies comprise a heavy chain variable domain that is at least 95% identical to, at least 96% identical to, at least 97% identical to, at least 98% identical to, or at least 99% identical to the amino acid sequence of SEQ ID NO:9. In one embodiment, Fab fully human anti-OX40 antibodies comprise a light chain variable domain that is at least 95% identical to, at least 96% identical to, at least 97% identical to, at least 98% identical to, or at least 99% identical to the amino acid sequence of a group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

In one embodiment, the Fab fully human antibody comprises a heavy chain/light chain set selected from a group consisting of SEQ ID NO:9/SEQ ID NO:3, SEQ ID NO:9/SEQ ID NO:4, SEQ ID NO:9/SEQ ID NO:5, SEQ ID NO:9/SEQ ID NO:6, SEQ ID NO:9/SEQ ID NO:7, and SEQ ID NO:9/SEQ ID NO:8.

In one embodiment, the Fab fully human anti-OX40 antibodies comprise an antigen binding protein that binds OX40, wherein the antigen binding protein comprises a heavy chain variable domain comprising CDRs as set forth in the amino acid sequence of SEQ ID NO:9 and comprises a light chain variable domain comprising CDRs as set forth in the amino acid sequence and selected from a group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

In one embodiment, the Fab fully human antibody binds human OX40. In one embodiment, the Fab fully human antibody binds cynomolgus OX40. In one embodiment, the fully human antibody binds rat and/or mouse OX40, or does not bind rat and/or mouse OX40.

In one embodiment, the Fab fully human antibody binds human OX40 and exhibits a $K_d$ of less than $1 \times 10^{-8}$ M.

In one embodiment, the Fab fully human antibody exhibits OX40 agonist activity. In one embodiment, the Fab fully human antibody increases proliferation of effector T cells (e.g., CD4+ effector T cells). In one embodiment, the Fab fully human antibody induces effector T cells (e.g., CD4+ effector T cells) to increase production of at least one cytokine selected from a group consisting of gamma-interferon, IL-2, IL-4 and tumor necrosis factor (TNF). In one embodiment, the Fab fully human antibody increases proliferation of effector T cells (e.g., CD8+ effector T cells). In one embodiment, the Fab fully human antibody inhibits regulatory T cell function, for example inhibits suppressive function of regulatory T cells. In one embodiment, the Fab fully human antibody induces proliferation of effector T cells (Teff) in the presence of regulatory T cells (Treg).

In one embodiment, the Fab fully human antibody induces OX40-mediated signal transduction in an OX40-expressing target cell. For example, OX40-mediated signal transduction can be monitored using transgenic cells that express OX40 and a reporter gene fused to an NFkB promoter, where contacting the transgenic cells with a variant anti-OX40 antibody induces increased NFkB transcription which is detectable using an assay for the reporter gene. In one embodiment, the reporter gene comprises luciferase.

One embodiment comprises a nucleic acid encoding the heavy chain variable domain sequence that is at least 95% identical to the amino acid sequences of SEQ ID NO. 9. One embodiment comprises a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

One embodiment comprises a vector comprising a nucleic acid encoding the heavy chain variable domain sequence that is at least 95% identical to the amino acid sequences of SEQ ID NO. 9. One embodiment comprises a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

One embodiment comprises a host cell harboring a vector comprising a nucleic acid encoding the heavy chain variable domain sequence that is at least 95% identical to the amino acid sequences of SEQ ID NO. 9. One embodiment comprises a host cell harboring a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the host cell is transfected or transformed with the vector comprising the nucleic acid.

One embodiment comprises a pharmaceutical composition, comprising: (a) a fully a human antibody of an IgG class that binds OX40, comprising a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein); and (b) a pharmaceutically acceptable carrier, diluent or excipient.

The present disclosure provides a single chain fully human antibody that binds OX40, or an antigen binding portion thereof, which has a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, single chain fully human anti-OX40 antibodies comprise a heavy chain variable domain that is at least 95% identical to, at least 96% identical to, at least 97% identical to, at least 98% identical to, or at least 99% identical to the amino acid sequence of SEQ ID NO:9. In one embodiment, single chain fully human anti-OX40 antibodies comprise a light chain variable domain that is at least 95% identical to, at least 96% identical to, at least 97% identical to, at least 98% identical to, or at least 99% identical to the amino acid sequence of a group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein).

In one embodiment, the single chain fully human antibody of claim 1, comprising a heavy chain/light chain set selected from a group consisting of SEQ ID NO:9/SEQ ID NO:3, SEQ ID NO:9/SEQ ID NO:4, SEQ ID NO:9/SEQ ID NO:5, SEQ ID NO:9/SEQ ID NO:6, SEQ ID NO:9/SEQ ID NO:7, and SEQ ID NO:9/SEQ ID NO:8.

In one embodiment, the single chain fully human anti-OX40 antibodies comprise an antigen binding protein that binds OX40, wherein the antigen binding protein comprises a heavy chain variable domain comprising CDRs as set forth in the amino acid sequence of SEQ ID NO:9 and comprises a light chain variable domain comprising CDRs as set forth in the amino acid sequence and selected from a group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

In one embodiment, the single chain fully human antibody binds human OX40. In one embodiment, the single chain fully human antibody binds cynomolgus OX40. In one embodiment, the fully human antibody binds rat and/or mouse OX40, or does not bind rat and/or mouse OX40.

In one embodiment, the single chain fully human antibody binds human OX40 and exhibits a $K_d$ of less than $1 \times 10^{-8}$ M.

In one embodiment, the single chain fully human antibody exhibits OX40 agonist activity. In one embodiment, the single chain fully human antibody increases proliferation of effector T cells (e.g., CD4+ effector T cells). In one embodiment, the single chain fully human antibody induces effector T cells (e.g., CD4+ effector T cells) to increase production of at least one cytokine selected from a group consisting of gamma-interferon, IL-2, IL-4 and tumor necrosis factor (TNF). In one embodiment, the single chain fully human antibody increases proliferation of effector T cells (e.g., CD8+ effector T cells). In one embodiment, the single chain fully human antibody inhibits regulatory T cell function, for example inhibits suppressive function of regulatory T cells. In one embodiment, the single chain fully human antibody induces proliferation of effector T cells (Teff) in the presence of regulatory T cells (Treg).

In one embodiment, the fully human antibody induces OX40-mediated signal transduction in an OX40-expressing target cell. For example, OX40-mediated signal transduction can be monitored using transgenic cells that express OX40 and a reporter gene fused to an NFkB promoter, where contacting the transgenic cells with a variant anti-OX40 antibody induces increased NFkB transcription which is detectable using an assay for the reporter gene. In one embodiment, the reporter gene comprises luciferase.

One embodiment comprises a nucleic acid encoding the heavy chain variable domain sequence that is at least 95% identical to the amino acid sequences of SEQ ID NO. 9. One embodiment comprises a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

One embodiment comprises a vector comprising a nucleic acid encoding the heavy chain variable domain sequence that is at least 95% identical to the amino acid sequences of SEQ ID NO. 9. One embodiment comprises a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

One embodiment comprises a host cell harboring a vector comprising a nucleic acid encoding the heavy chain variable domain sequence that is at least 95% identical to the amino acid sequences of SEQ ID NO. 9. One embodiment comprises a host cell harboring a vector comprising a nucleic acid encoding the light chain variable domain sequence which is selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein). In one embodiment, the host cell is transfected or transformed with the vector comprising the nucleic acid.

One embodiment comprises a pharmaceutical composition, comprising: (a) a fully a human antibody of an IgG class that binds OX40, comprising a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein); and (b) a pharmaceutically acceptable carrier, diluent or excipient.

The present disclosure provides a method for inducing proliferation of effector T cells, comprising: contacting the effector T cells with an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein). In one embodiment, the method further comprises: detecting an increase in proliferation of the effector T cells. In one embodiment, the anti-OX40 antibody comprises a fully human antibody of an IgG class that binds OX40 or an antigen binding portion thereof, a Fab fully human antibody, or a single chain fully human antibody. In one embodiment, the effector T cells are contacted with CD3 and the fully human antibody that binds OX40. In one embodiment, the fully human antibody contacts the effector T cells which are CD4+ effector T cells. In one embodiment, the proliferation of the effector T cells increases by about 5%, or 5-10%, or 10-20%, or 20-30%, or 30-40%, or 40-50%, or 50-100%. In one embodiment, the proliferation of the effector T cells increases about 1-5 fold, or about 5-10 fold, or more.

The present disclosure provides a method for inducing proliferation of effector T cells, comprising: contacting the effector T cells with an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein). In one embodiment, the method further comprises: detecting an increase in proliferation of the effector T cells. In one embodiment, the anti-OX40 antibody comprises a fully human antibody of an IgG class that binds OX40 or an antigen binding portion thereof, a Fab fully human antibody, or a single chain fully human antibody. In one embodiment, the effector T cells are contacted with CD3 and the fully human antibody that binds OX40. In one embodiment, the fully human antibody contacts the effector T cells which are CD8+ effector T cells. In one embodiment, the proliferation of the effector T cells increases by about 5%, or 5-10%, or 10-20%, or 20-30%, or 30-40%, or 40-50%, or 50-100%. In one embodiment, the proliferation of the effector T cells increases about 1-5 fold, or about 5-10 fold or more.

The present disclosure provides a method for inducing effector T cells to increase production of at least one cytokine, comprising: contacting effector T cells with an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the method further comprises: detecting an increase in production of the at least one cytokine by the effector T cells. In one embodiment, the anti-OX40 antibody comprises a fully human antibody of an IgG class that binds OX40 or an antigen binding portion thereof, a Fab fully human antibody, or a single chain fully human antibody. In one embodiment, the at least one cytokine is selected from a group consisting of gamma-interferon, IL-2, IL-4 and tumor necrosis factor (TNF). In one embodiment, the effector T cells are contacted with CD3 and the fully human antibody that binds OX40. In one embodiment, the fully human antibody contacts effector T cells which are CD4+ effector T cells. In one embodiment, the production of gamma-interferon, IL-2, IL-4 and/or tumor necrosis factor (TNF) by the effector T cells increases by about 5%, or 5-10%, or 10-20%, or 20-30%, or 30-40%, or 40-50%, or 50-100%. In one embodiment, the production of gamma-interferon, IL-2, IL-4 and/or tumor necrosis factor (TNF) by the effector T cells increases by about 1-5 fold, or about 5-10 fold or more.

The present disclosure provides a method for inhibiting suppressive function of regulatory T cells (Treg), comprising: contacting regulatory T cells with an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the method further comprises: detecting a decrease function or inhibited suppressive function of the regulatory T cells. In one embodiment, the anti-OX40 antibody comprises a fully human antibody of an IgG class that binds OX40 or an antigen binding portion thereof, a Fab fully human antibody, or a single chain fully human antibody. In one embodiment, the regulatory T cells are contacted with CD3 and the fully human antibody that binds OX40. In one embodiment, the fully human antibody contacts regulatory T cells which are CD4+ regulatory T cells. In one embodiment, the suppressive function of the regulatory T cells is inhibited or decreases by about 5%, or 5-10%, or 10-20%, or 20-30%, or 30-40%, or 40-50%, or 50-100%. In one embodiment, the suppressive function of the regulatory T cells is inhibited or decreases by about 1-5 fold, or about 5-10 fold or more.

The present disclosure provides a method for inducing proliferation of effector T cells (Teff) in the presence of regulatory T cells (Treg), comprising: contacting the effector T cells and the regulatory T cells with an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the method further comprises: detecting an increase in proliferation of the effector T cells. In one embodiment, the anti-OX40 antibody comprises a fully human antibody of an IgG class that binds OX40 or an antigen binding portion thereof, a Fab fully human antibody, or a single chain fully human antibody. In one embodiment, the effector T cell and the regulatory T cell are contacted with CD3 and the fully human antibody that binds OX40. In one embodiment, the effector T cells express CD25-low. In one embodiment, the effector T cells produce at least one cytokine selected from a group consisting of IL-2, IL-4 and INFγ. In one embodiment, the regulatory T cells express CD25-high. In one embodiment, the T regulatory cells produce IL-10 and/or TGFβ. In one embodiment, the proliferation of the effector T cells increases by about 5%, or 5-10%, or 10-20%, or 20-30%, or 30-40%, or 40-50%, or 50-100%. In one embodiment, the proliferation of the effector T cells increases about 1-5 fold, or about 5-10 fold. In one embodiment, the suppressive function of the regulatory T cells is inhibited or decreases by about 5%, or 5-10%, or 10-20%, or 20-30%, or 30-40%, or 40-50%, or 50-100%. In one embodiment, the suppressive function of the regulatory T cells is inhibited or decreases by about 1-5 fold, or about 5-10 fold or more.

The present disclosure provides a method for treating a subject having cancer, comprising administering an effective amount of an anti-OX40 antibody to the subject, wherein the anti-OX40 antibody comprises an anti-OX40 antibody, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8) herein), SEQ ID NO. 6 called 5-F5 herein SEQ ID NO. 7 (called 5-G8 herein), and SEQ ID NO. 8 (called 5-H6 herein). In one embodiment, the anti-OX40 antibody comprises a fully human antibody of an IgG class that binds OX40 or an antigen binding portion thereof, a Fab fully human antibody, or a single chain fully human antibody. In one embodiment, the cancer is selected from a group consisting of prostate cancer, breast cancer, ovarian cancer, head and neck cancer, bladder cancer, melanoma, colorectal cancer, pancreatic cancer, lung cancer, leiomyoma, leiomyosarcoma, glioma, glioblastoma, esophageal cancer, liver cancer, kidney cancer, stomach cancer, colon cancer, cervical cancer, uterine cancer, liver cancer and a hematological cancer. In one embodiment, the cancer is selected from the group consisting of B chronic lymphocytic leukemia (B-CLL), B and T acute lymphocytic leukemia (ALL), acute myeloid leukemia (AML), chronic lymphocytic leukemia (CLL), chronic myelogenous leukemia (CML), hairy cell leukemia (HCL), myeloproliferative disorder/neoplasm (MPDS), myelodysplasia syndrome, non-Hodgkin's lymphoma (NHL), including Burkitt's lymphoma (BL), Waldenstrom's Macroglobulinemia, mantle cell lymphoma, AIDS-related lymphoma, Hodgkin's Lymphoma (HL), T cell lymphoma (TCL), multiple myeloma (MM), plasma cell myeloma, plamocytoma, giant cell myeloma, heavy-chain myeloma, and light chain or Bence-Jones myeloma.

The present disclosure provides a method for treating a subject having an inflammatory disease, the method comprising: comprising administering an effective amount of an anti-OX40 antibody to the subject, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8), SEQ ID NO. 6 called 5-F5 herein SEQ ID NO. 7 (called 5-G8 herein), and SEQ ID NO. 8 (called 5-H6 herein). In one embodiment, the anti-OX40 antibody comprises a fully human antibody of an IgG class that binds OX40 or an antigen binding portion thereof, a Fab fully human antibody, or a single chain fully human antibody. In one embodiment, the inflammatory disease is selected from the group consisting of allergy, COPD, autoimmune disease, rheumatoid arthritis, asthma, graft versus host disease, Crohn's disease, ulcerative colitis, type-1 diabetes, multiple sclerosis, Systemic lupus erythematosis, lupus nephritis, Myasthenia Gravis, Grave's disease, transplant rejection, Wegener's granulomatosis, Henoch-Schonlein purpura, systemic sclerosis, and viral-induced lung inflammation.

The present disclosure provides a method for treating a subject having an infection, comprising: administering an effective amount of an anti-OX40 antibody to the subject, wherein the fully human antibody comprises a heavy chain variable domain sequence that is at least 95% identical to the amino acid sequences of SEQ ID NO. 9, and a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein). In one embodiment, the anti-OX40 antibody comprises a fully human antibody of an IgG class that binds OX40 or an antigen binding portion thereof, a Fab fully human antibody, or a single chain fully human antibody. In one embodiment, the infection is selected from a group consisting of a bacterial infection, a viral infection and a pathogen infection.

The present disclosure provides anti-OX40 antibodies that are labeled or unlabeled for diagnostic purposes. The anti-OX40 antibodies include fully a human antibody, or an antigen binding portion thereof, or Fab fully human antibody fragment, or single chain human antibody, that are attached to a label or are unlabeled. Labels include radionuclides, fluorescers, enzymes, enzyme substrates, enzyme co-factors, enzyme inhibitors and ligands (e.g., biotin). In one embodiment, diagnostic procedures comprise contacting a labeled anti-OX4 antibody (e.g., radionuclide or fluorophore-labeled) with OX40 antigen, and detecting formation of a complex containing a labeled anti-OX40 antibody bound to OX40 (e.g., detecting the radionuclide or fluorescence). In one embodiment, enzyme immunoassays comprise contacting an enzyme-labeled anti-OX40 antibody with OX40 antigen to form a complex, and contacting the complex with a substrate that interacts with the enzyme that is attached to the anti-OX40 antibody under conditions suitable to cause the enzyme to catalyze a reaction that generates a detectable change (e.g., colorimetric detection).

BRIEF DESCRIPTION OF THE FIGURES

FIG. 2H shows a table listing various binding kinetic values derived from surface plasmon resonance of parent clone 2B4 (WT) and the six variant clones.

FIG. 2J shows a table listing various binding kinetic values derived from surface plasmon resonance data of FIG. 9H of MOXR0916/RG7888.

DETAILED DESCRIPTION

Figure 1:
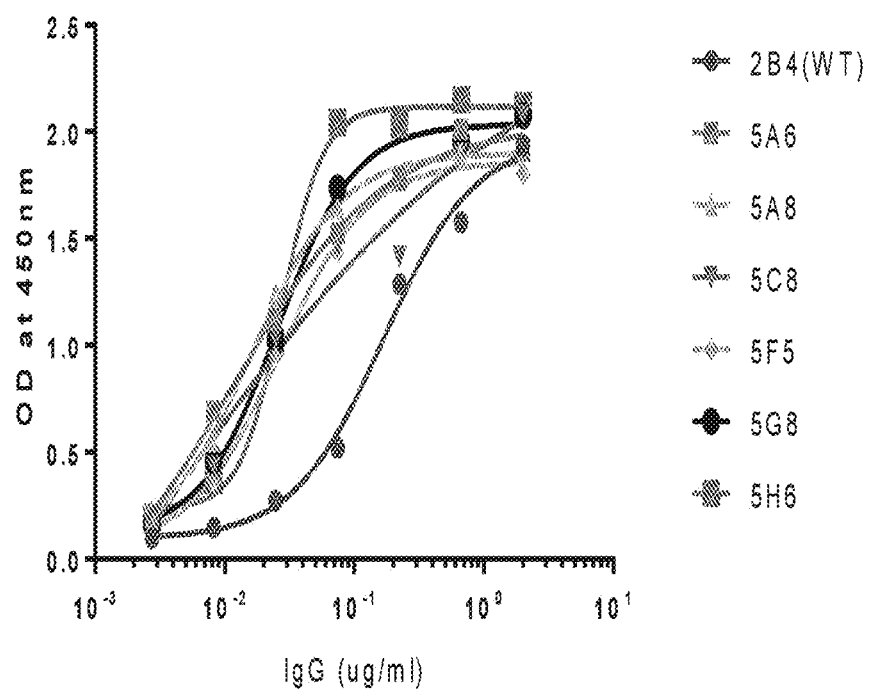
FIG. 1 shows a comparison of ELISA binding data comparing 6 variant clones to the binding of their parent wild type 2B4 sequence (FIG. 1). The IC50 data are compared in the table in FIG. 1.
Figure 2A:
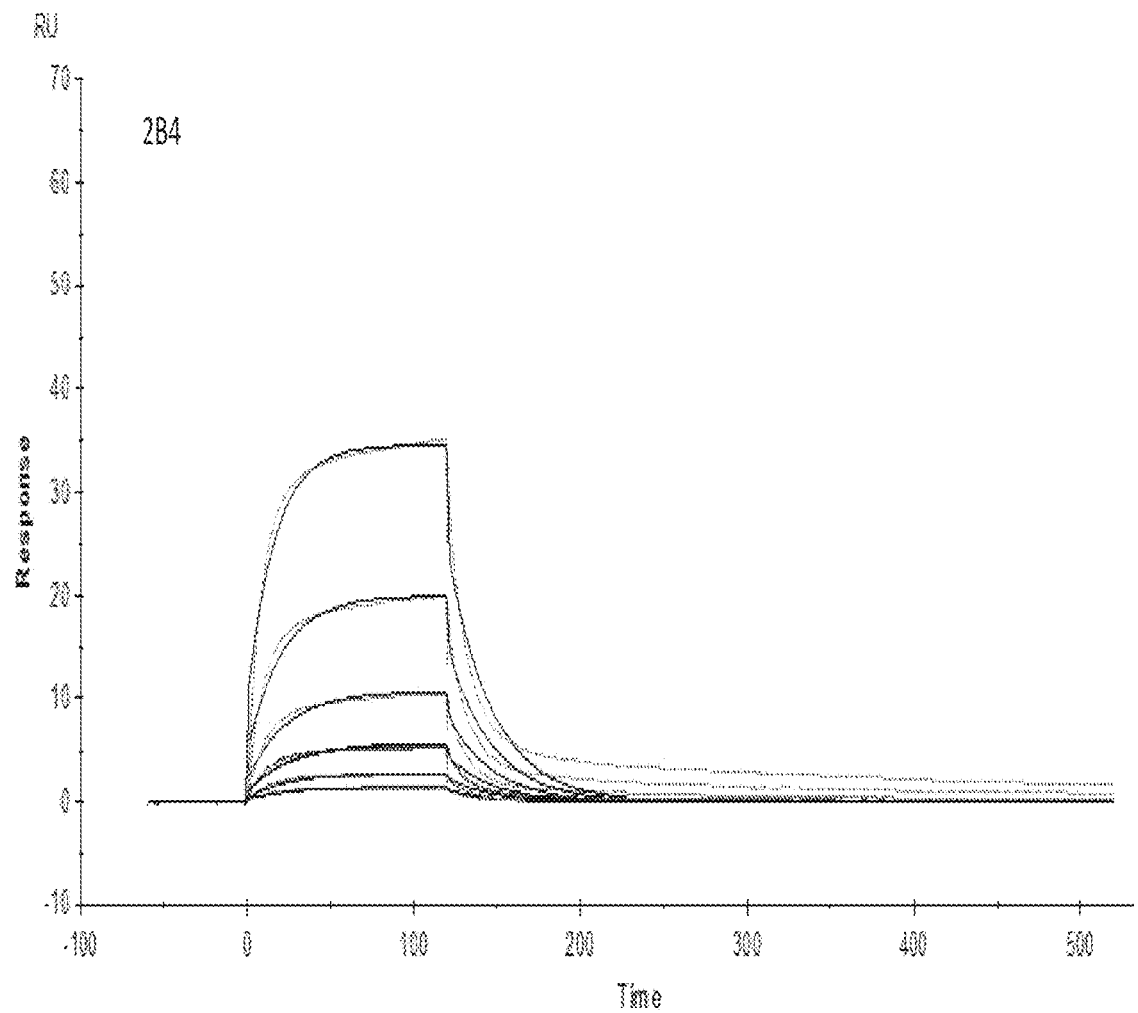
FIG. 2A shows an SPR sensogram generated via surface plasmon resonance for antibody-antigen affinity of 2B4 (WT) and a table listing various binding kinetics.
Figure 2B:
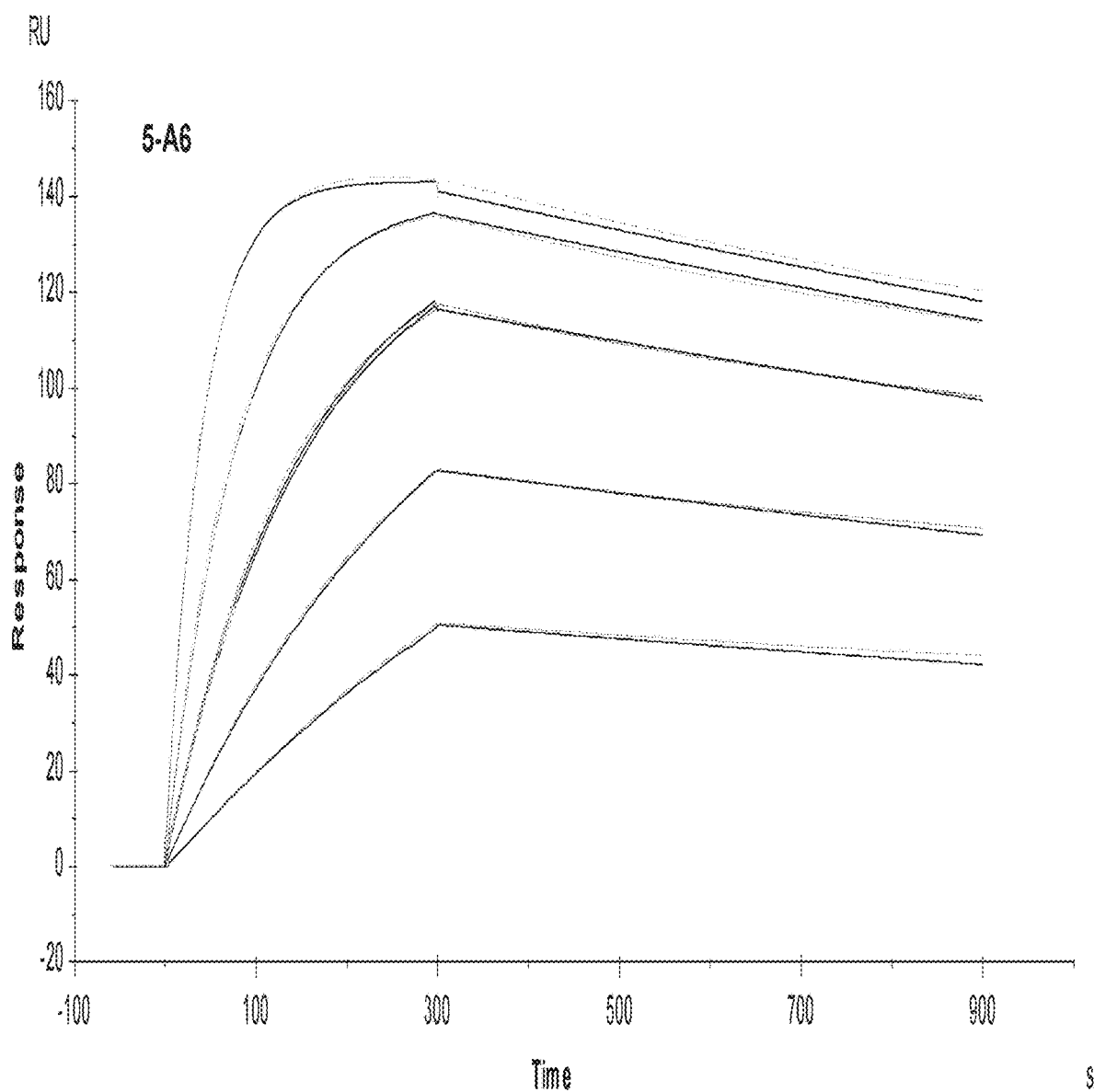
FIG. 2B shows an SPR sensogram generated via surface plasmon resonance for antibody-antigen affinity of clone 5A6.
Figure 2C:
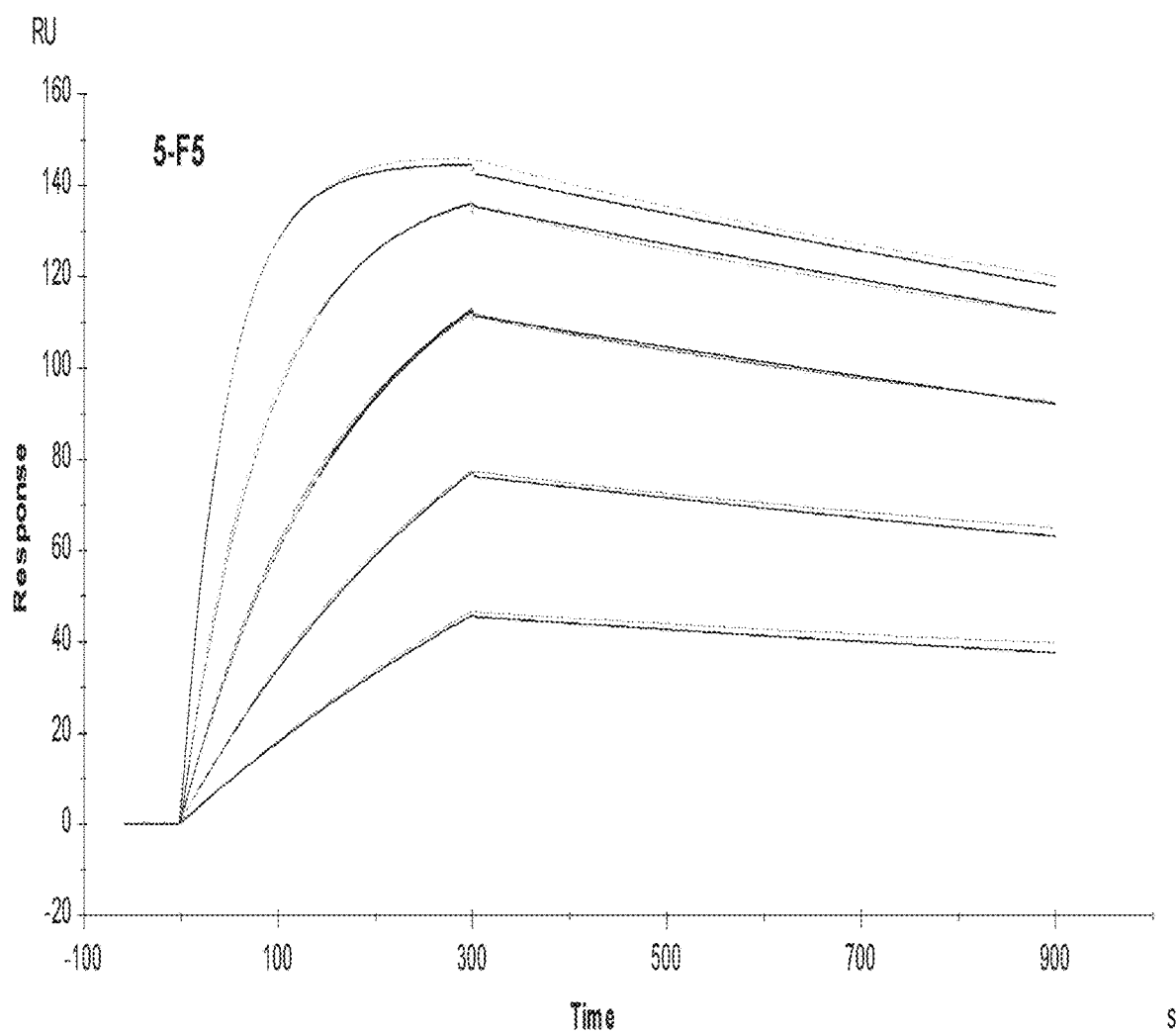
FIG. 2C shows an SPR sensogram generated via surface plasmon resonance for antibody-antigen affinity of clone 5F5.
Figure 2D:
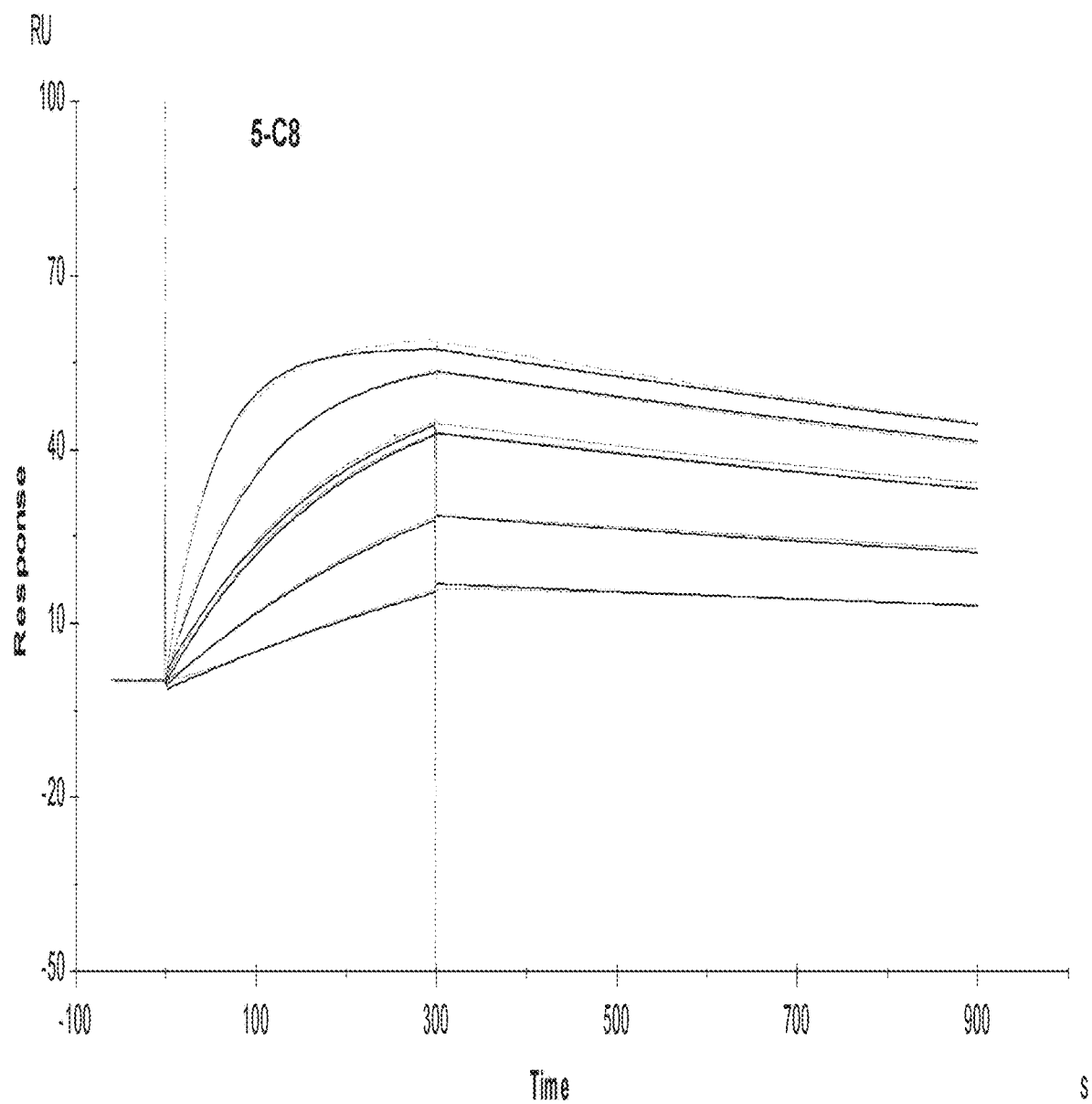
FIG. 2D shows an SPR sensogram generated via surface plasmon resonance for antibody-antigen affinity of clone 5C8.
Figure 2E:
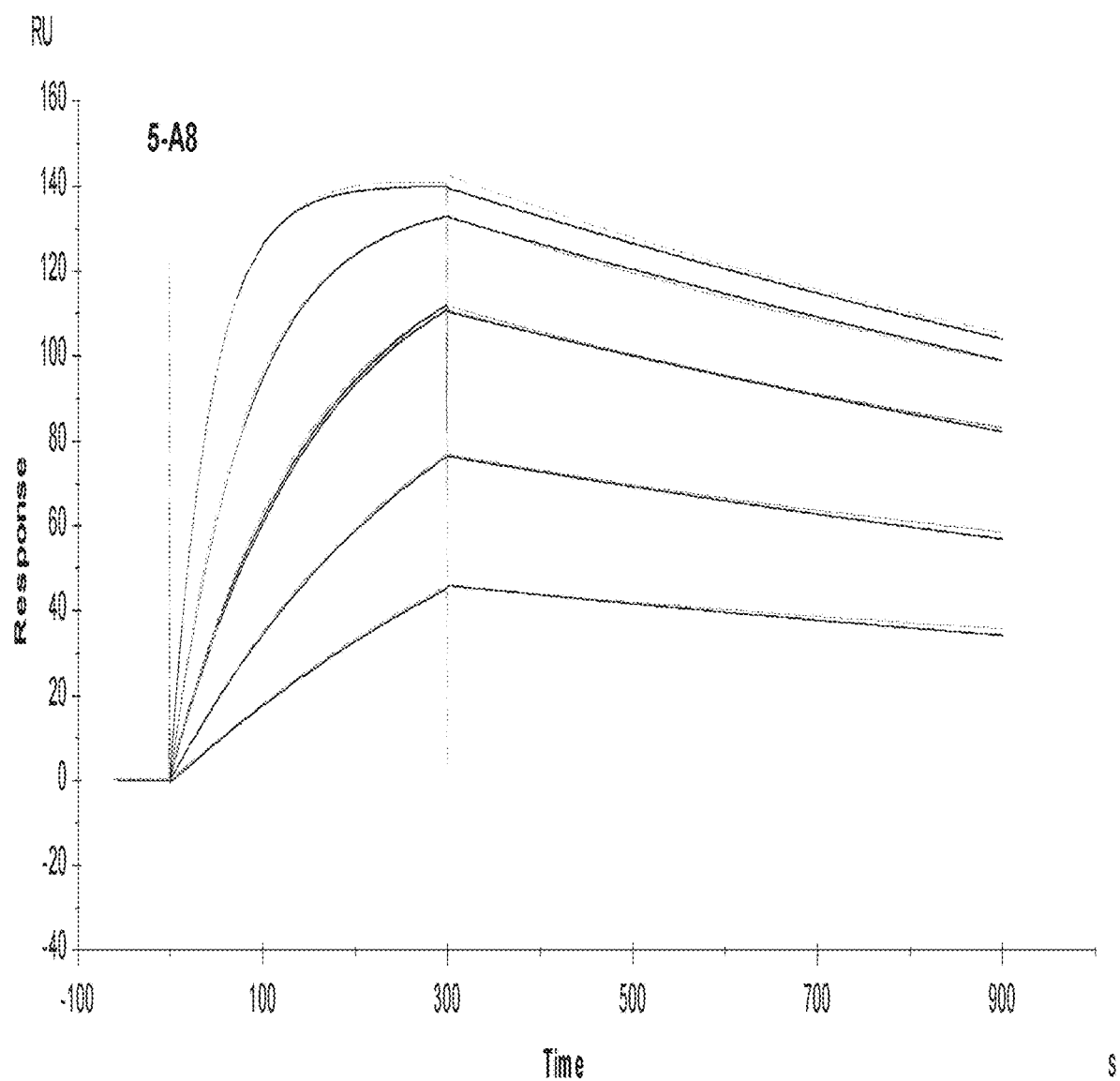
FIG. 2E shows an SPR sensogram generated via surface plasmon resonance for antibody-antigen affinity of clone 5A8.
Figure 2F:
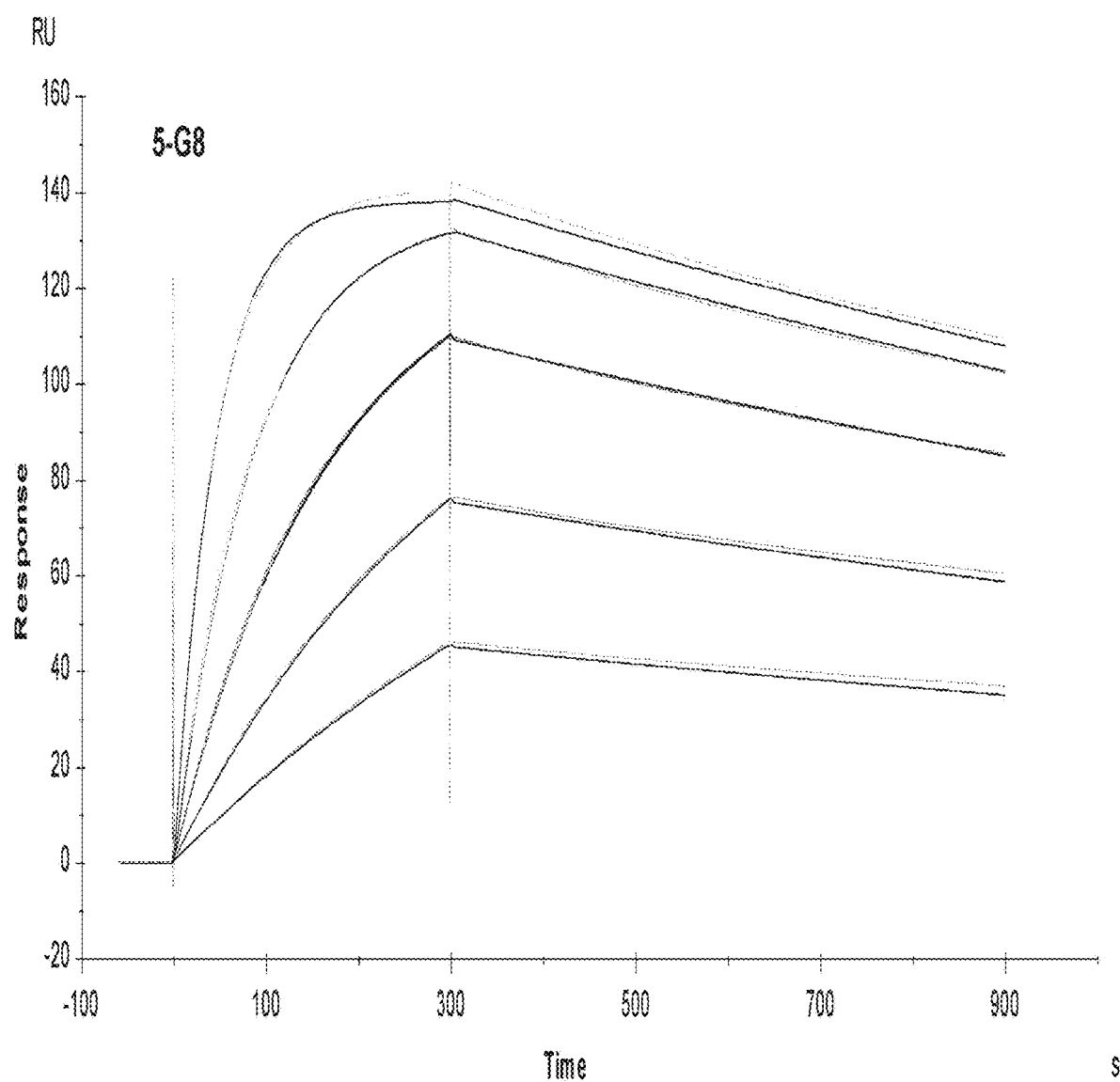
FIG. 2F shows an SPR sensogram generated via surface plasmon resonance for antibody-antigen affinity of clone 5G8.
Figure 2G:
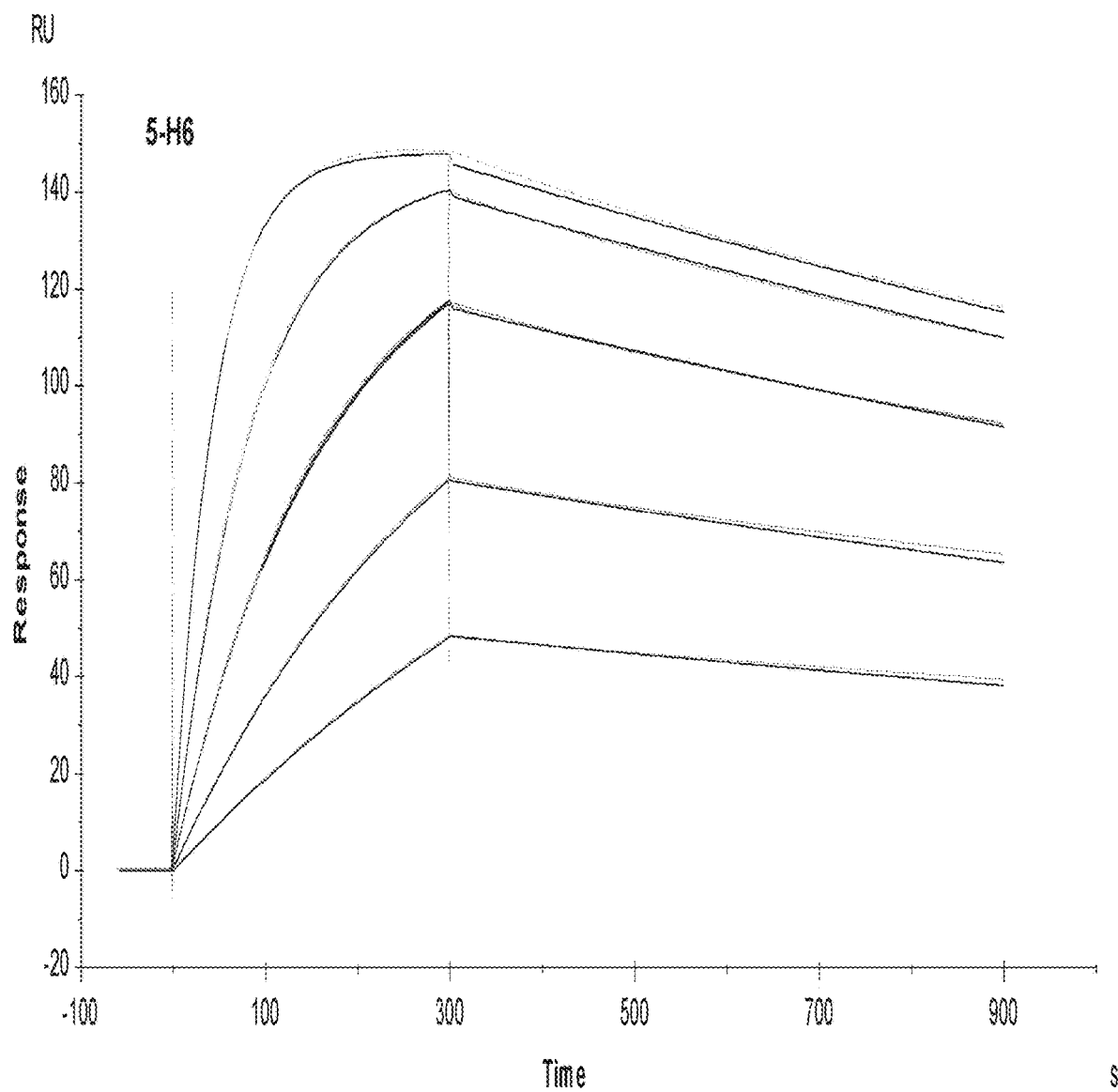
FIG. 2G shows an SPR sensogram generated via surface plasmon resonance for antibody-antigen affinity of clone 5H6.
Figure 2I:
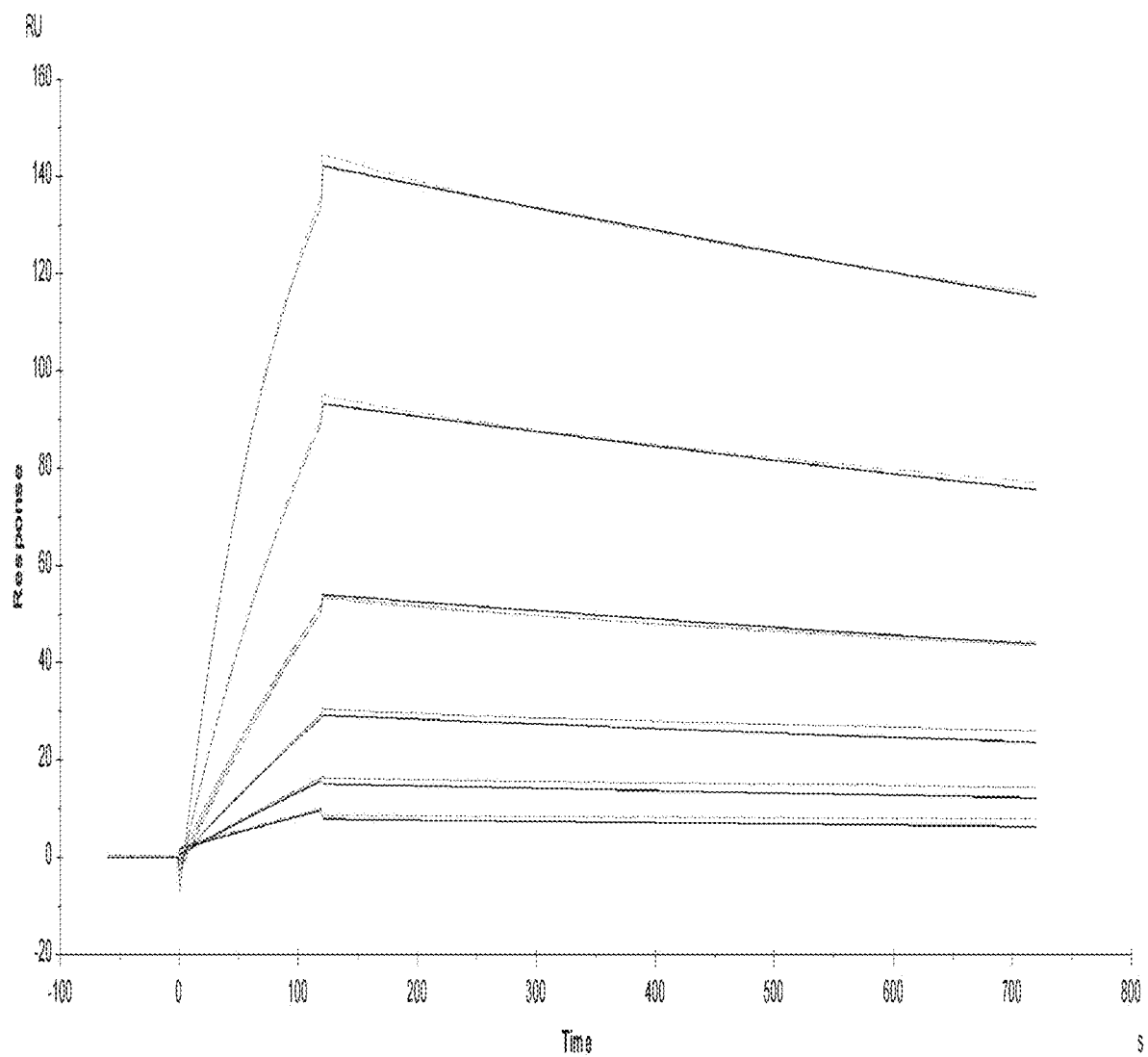
FIG. 2I shows an SPR sensogram generated via surface plasmon resonance for antibody-antigen affinity of MOXR0916/RG7888.

The present disclosure found that an antibody (called 2B4) disclosed in U.S. Patent application 62/371,993 filed 8 Aug. 2016 and in PCT/US2017/045788 filed 7 Aug. 2017 (the disclosure of which is incorporated by reference herein) as wild type SEQ ID NO. 24 for the heavy chain and SEQ ID NO. 25 for the light chain for more favorable binding characteristics when modified in both its heavy chain and light chain sequences. The same 2B4 wild type sequences are provided herein as SEQ ID No. 1 for the heavy chain and SEQ ID NO. 2 for the light chain. Therefore, the present disclosure provides a fully human antibody of an IgG class that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

The present disclosure provides a Fab fully human antibody fragment that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

The present disclosure provides a single chain human antibody that binds to an OX40 epitope, which has a heavy chain variable domain sequence that is at least 95% identical to the amino acid sequences of SEQ ID NO. 9, and that has a light chain variable domain sequence selected from the group consisting of SEQ ID NO. 3 (called 5-A6 herein), SEQ ID NO. 4 (called 5-A8 herein), SEQ ID NO. 5 (called 5-C8 herein), SEQ ID NO. 6 called 5-F5 herein SEQ ID NO. 7 (called 5-G8 herein), and SEQ ID NO. 8 (called 5-H6 herein).

Definitions

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT®. (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alfa, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

The basic antibody structural unit is a tetramer. Each tetramer is composed of two identical pairs of polypeptide chains, each pair having one "light" (about 25 kDa) and one "heavy" chain (about 50-70 kDa). Generally, the amino-terminal portion of each antibody chain includes a variable region that is primarily responsible for antigen recognition. The carboxy-terminal portion of each chain defines a constant region, e.g., responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "j" region of about 12 or more amino acids, with the heavy chain also including a "D" region of about 3 or more amino acids. The variable regions of each heavy/light chain pair (VH/VL), respectively, form the antigen binding site. The variable regions of antibody heavy and light chains (VH/VL exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is known in the art, including, for example, definitions as described in Kabat et al. in Sequences of Proteins of Immunological Interest, 5$^{th}$ Ed., US Dept. of Health and Human Services, PHS, MH, NIH Publication no. 91-3242, 1991 (herein referred to as "Kabat numbering"). For example, the CDR regions of an antibody can be determined according to Kabat numbering.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US App. Pub.20/0202512; 2004/0202995; 2004/0038291; 2004/0009507; 2003/0039958, and Ward et al., *Nature* 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The term "isolated" refers to a protein (e.g., an antibody) or polynucleotide that is substantially free of other cellular material. A protein may be rendered substantially free of naturally associated components (or components associated with the cellular expression system used to produce the antibody) by isolation, using protein purification techniques well known in the art. In one embodiment, the anti-OX antibodies or antigen binding portions thereof, of the present disclosure are isolated.

The terms "anti-OX40 antibody" and "an antibody that binds to OX40" refer to an antibody that is capable of binding OX40 with sufficient affinity such that the antibody is useful as a diagnostic and/or therapeutic agent in targeting OX40, including human OX40.

An "epitope" is the portion of a molecule that is bound by an antigen binding, protein (e.g., by an antibody). An epitope can comprise non-contiguous portions of the molecule (e.g., in a polypeptide amino add residues that are not contiguous in the polypeptide's primary sequence but that, in the context of the polypeptide's tertiary and quaternary structure, are near enough to each other to be bound by an antigen binding protein). Generally the variable regions, particularly the CDRs, of an antibody interact with the epitope.

The terms "specific binding", "specifically binds" or "specifically binding", as used herein in the context of an antibody, refer to non-covalent or covalent preferential binding of an antibody to an antigen relative to other molecules or moieties (e.g., an antibody specifically binds to a particular antigen relative to other available antigens). In one embodiment, an antibody specifically binds to an antigen (e.g., OX40) if it binds to the antigen with a dissociation constant $K_d$ of $10^{-5}$ M or less (e.g., $10^{-6}$ M or less. $10^{-7}$ M or less, $10^{-8}$ M or less, $10^{-9}$ M or less, or $10^{-10}$ M or less).

In one embodiment, a dissociation constant ($K_d$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

An "antibody fragment" "antibody portion", "antigen-binding fragment of an antibody", or "antigen-binding portion of an antibody" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well azo dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment.

The term "human antibody", as used herein, refers to an antibody, or an antigen binding fragment of an antibody, comprising heavy and lights chains derived from human immunoglobulin sequences. In one embodiment, variable and constant regions of the heavy and light chains are derived from human immunoglobulin sequences (e.g., fully human antibodies). Human antibodies may be prepared in a variety of ways, including by immunization with an antigen of interest of a mouse that is genetically modified to express antibodies derived from human heavy and/or light chain-encoding genes. In one embodiment, a human antibody is made using recombinant methods such that the glycosylation pattern of the antibody is different than an antibody having the same sequence if it were to exist in nature.

The terms "nucleic acid", "polynucleotide" and "oligonucleotide" and are used interchangeably and refers to polymers of nucleotides. Nucleic acids include naturally-occurring, recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof.

The terms "peptide", "polypeptide" and "protein" are used interchangeably and refer to a polymer of amino acids and are not limited to any particular length. Polypeptides comprise natural and non-natural amino acids. Polypeptides can be naturally-occurring or recombinant or chemically-synthesized forms. These terms encompass native and artificial proteins, protein fragments and polypeptide analogs (such as muteins, variants, chimeric proteins and fusion proteins) of a protein sequence as well as post-translationally, or otherwise covalently or noncovalently, modified proteins. A peptide, polypeptide, or protein may be monomeric or polymeric. Polypeptides includes antibodies, portions of antibodies, antibody chains, scFv and chimeric antigen receptor constructs.

The "percent identity" or "percent homology" refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters.

In one embodiment, an anti-OX40 antibody may be similar but not identical to any of the anti-OX40 antibodies described herein. The similar anti-OX40 antibody can be at least 95%, or at or at least 96% identical, or at least 97% identical, or at least 98% identical, or at least 99% identical, to any of the anti-OX40 antibodies described herein. In one embodiment, similar anti-OX40 antibodies can contain amino acid substitutions within a heavy and/or light chain. In one embodiment, the amino acid substitutions comprise one or more conservative amino acid substitutions, A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

A "vector" refers to a nucleic acid molecule (e.g., DNA or RNA) which can be operably linked to foreign genetic material (e.g., nucleic acid transgene). Vectors can be single-stranded or double-stranded nucleic acid molecules. Vectors can be linear or circular nucleic acid molecules. Vectors can be used as a vehicle to introduce foreign genetic material into a cell (e.g., host cell). One type of vector is a "plasmid," which refers to a linear or circular double stranded extra-chromosomal DNA molecule which can be linked to a transgene, and is capable of replicating in a host cell, and transcribing and translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral and adeno-associated vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can contain one or more regulatory sequences, such as inducible and/or constitutive promoters and enhancers, or can contain ribosomal binding sites and/or polyadenylation sites. Regulatory sequences direct transcription, or transcription and translation, of a transgene linked to the expression vector which is transduced into a host cell. The regulatory sequence(s) can control the level, timing or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, *Nucleic Acids Res.* 23:3605-3606.

A transgene is "operably linked" to a vector when there is linkage between the transgene and the vector to permit functioning or expression of the vector sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" refer to a process by which exogenous nucleic acid (e.g., transgene) is transferred or introduced into a host cell. A "transfected" or "transformed" or "transduced" host cell is one which has been transfected, transformed or transduced with exogenous nucleic acid. The host cell includes the primary subject cell and its progeny.

A "host cell" or "or a population of host cells" refers to a cell (or a population thereof) into which foreign (exogenous) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an anti-OX40 antibody, as disclosed herein. In one example, the host cell (or population thereof) can be introduced with an expression vector operably linked to a nucleic acid encoding the anti-OX40 antibody, or an antigen binding portion thereof, described herein.

A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding an anti-OX40 antibody thereby generating a transfected/transformed host cell which is cultured under conditions suitable for expression of the anti-OX40 antibody by the transfected/transformed host cell, and optionally recovering the anti-OX40 antibody from the transfected/transformed host cells or from the culture medium. Examples of host cells include the COS-7 line of monkey kidney cells (ATCC CRL 1651) (see Gluzman et al., 1981, Cell 23: 175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293,293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Anti-OX40 antibodies can be prepared using conventional procedures. In one embodiment, hosts cells can harbor an expression vector that carries a nucleic acid that encode the anti-OX40 antibody, where the host cells are cultured under conditions suitable to induce expression of the anti-OX40 antibody. In one embodiment, the nucleic acid encoding the anti-OX40 antibody includes a protein tag for purification procedures so that the expressed anti-OX40 antibody includes a protein tag. Tags include histidine tags, FLAG tags, myc tags, HA tags and GST tags. The anti-OX40 antibody can be enriched/purified from the cell culture medium to produce anti-OX40 antibody preparation that is substantially free of cellular components. In one embodiment, the protein tag is used to purify the anti-OX40 antibody.

The term "effective amount" as used herein, refers to that amount of an antibody or an antigen binding portion thereof that binds OX40, that when administered to a subject, is sufficient to effect a measurable improvement or prevention of a disease or disorder associated with OX40 signaling. Therapeutically effective amounts of antibodies provided herein, when used alone or in combination, will vary depending upon the relative activity of the antibodies and combinations (e.g. in inhibiting cell growth) and depending upon the subject and disease condition being treated, the weight and age and sex of the subject, the severity of the disease condition in the subject, the manner of administration and the like, which can readily be determined by one of ordinary skill in the art.

In one embodiment, a therapeutically effective amount will depend on certain aspects of the subject to be treated and the disorder to be treated, and may be ascertained by one skilled in the art using known techniques. In general, the polypeptide is administered at about 0.01 g/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

The anti-OX40 antibody, or antigen binding portion thereof, described herein can be administered to a subject by a variety of methods known in the art, although for many therapeutic applications, the preferred route/mode of administration is parenteral, subcutaneous injection, intravenous injection, infusion or oral. Oral administration can include the anti OX40 antibody, or antigen binding portion thereof, in the form as a pill, tablet, capsule, liquid or sustained release tablet. Methods are well known in the art for preparing pharmaceutical formulations, for example, in "Remington: The Science and Practice of Pharmacy" (20th ed., ed. A. R. Gennaro A R., 2000, Lippincott Williams & Wilkins, Philadelphia, Pa.).

As will be appreciated by the skilled artisan, the route and/or mode of administration will vary depending upon the desired results. In certain embodiments, the active compound may be prepared with a carrier (or diluent or excipient) that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, S. R. Robinson, ed., (Marcel Dekker, Inc., New York, 1978).

The term "OX40," as used herein, refers to any native OX40 from any vertebrate source, including mammals such as primates (e.g., humans) and rodents (e.g., mice and rats), unless otherwise indicated. The term encompasses "full-length," unprocessed OX40 as well as any form of OX40 that results from processing in the cell. The term also encompasses naturally occurring variants of OX40, for example, splice variants or allelic variants. In one embodiment, an exemplary human OX40 (lacking the signal peptide) comprising the amino acid sequence of SEQ ID NO. 10: LHCVGDTYPSNDRCCHECRPGNGMVSRCSR-SQNTVCRPCG
PGFYNDVVSSKPCKPCTWCNLRSGSERKQLC-TATQDTVCRCRAGT
QPLDSYKPGVDCAPCPPGHFSPGDNQACK-PWTNCTLAGKHTLQPA
SNSSDAICEDRDPPATQPQETQGPPARPITVQP-TEAWPRTSQGPSTRP
VEVPGGRAVAAILGLGLVLGLLGPLAILLA-LYLLRRDQRLPPDAHKP
PGGGSFRTPIQEEQADAHSTLAKI. In one embodiment, the anti-OX40 antibody, or antigen binding portion thereof, binds to OX40 comprising the amino acid sequence according to SEQ ID NO: 10.

Variant Anti-OX40 Antibodies

One of the hallmarks of OX40-specific co-stimulation is enhanced T cell clonal expansion and differentiation due to increased survival of the activated T cells. OX40 co-stimulation also promotes accumulation of effector T cells (Teff) expressing IL-2, IL-4 and IFNγ, and reduces the suppressive activity of regulatory T cells (Treg).

The present disclosure provides variant anti-OX40 antibodies (clones 5A6, 5A8, 5C8, 5F5, 5G8 and 5H6) that mimic the activity of OX40L by behaving as an agonist against receptor OX40 to enhance T cell clonal expansion and differentiation. The variant anti-OX40 antibodies specifically bind OX40 receptor. The variant anti-OX40 antibodies exhibit improved binding affinity for OX40 and improved agnostic activity, compared to wild type 2B4 antibody from which the variant clones are derived. The variant anti-OX40 antibodies specifically bind OX40 receptors on activated T lymphocytes, stimulate proliferation of effector T cells (e.g., CD4+ effector T cells), stimulate proliferation of effector T cells in the presence of regulatory T cells, and stimulate production of at least one cytokine (e.g., IL-2, IL-4 and IFNγ) from effector T cells (e.g., CD4+ effector T cells).

The immobilized variant anti-OX40 antibodies exhibit better binding capabilities to human OX40 compared to the wild type 2B4 antibody (FIG. 1). In one embodiment, the variant anti-OX40 antibodies bind human OX40 with an IC50 that is at least one order of magnitude lower than the IC50 of wild type B24 antibody as measured by an ELISA assay (see table at FIG. 1).

The variant anti-OX40 antibodies exhibit binding affinities that are about two orders of magnitude better compared to wild type 2B4 antibody. The variant anti-OX40 antibodies bind human OX40 with an affinity of less than 5 nM. The variant antibodies exhibit overall improved affinity and binding kinetics compared to wild type 2B4 as demonstrated by surface plasmon resonance (SPR) analysis (FIGS. 2A-J). All of the variant anti-OX40 antibodies bind to human OX40 with a $K_d$ of less than $5 \times 10^{-}$M (see the table at FIG. 2H) which is comparable to the $K_d$ of MOXR0916/RG7888 (Genentech) (see table at FIG. 2J).

Figure 3A:
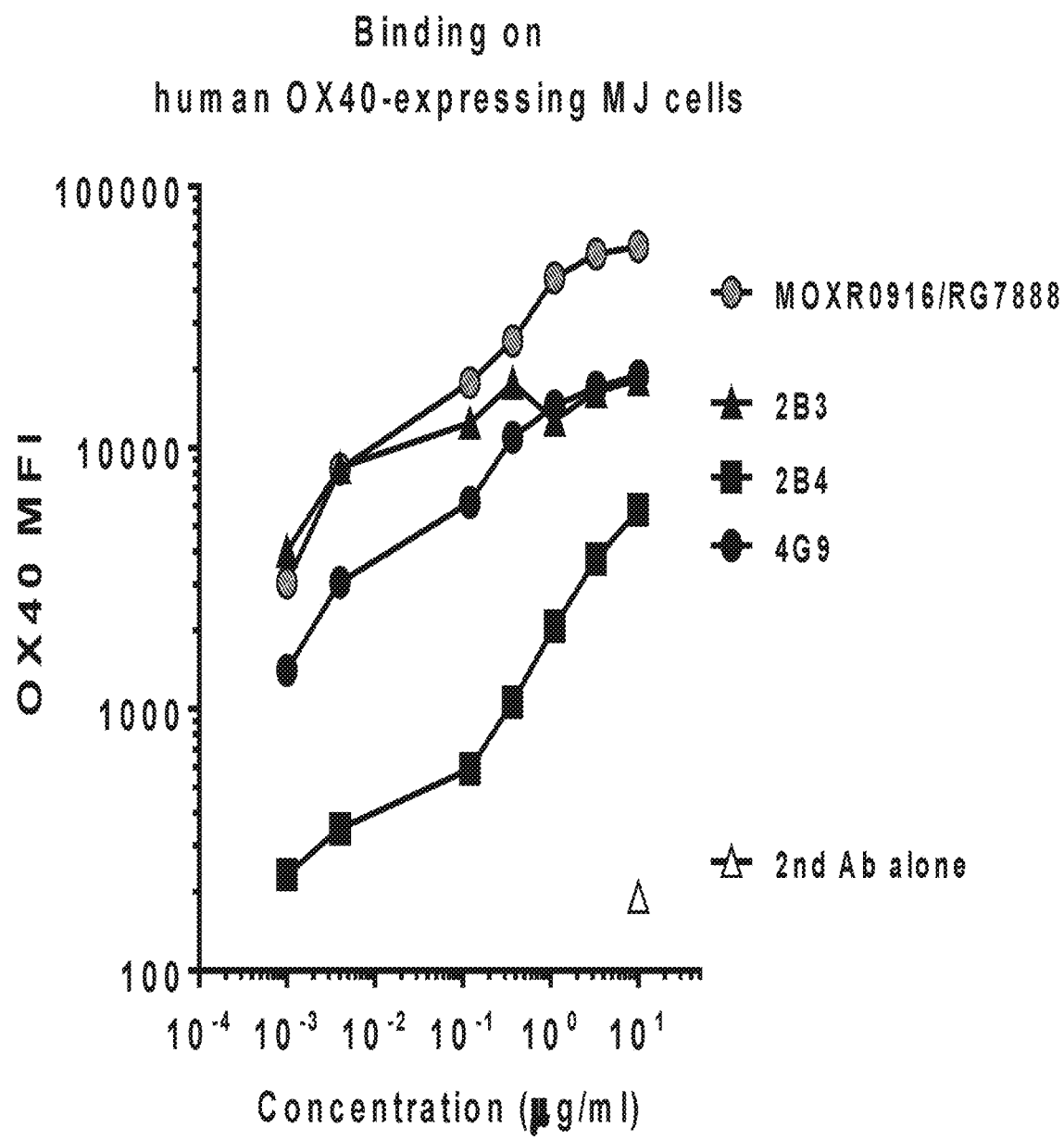
FIG. 3A shows FACS binding data of antibody clone 2B4 (WT) and two other clones with MJ cells (human cutaneous T-cell lymphoma).
Figure 3B:
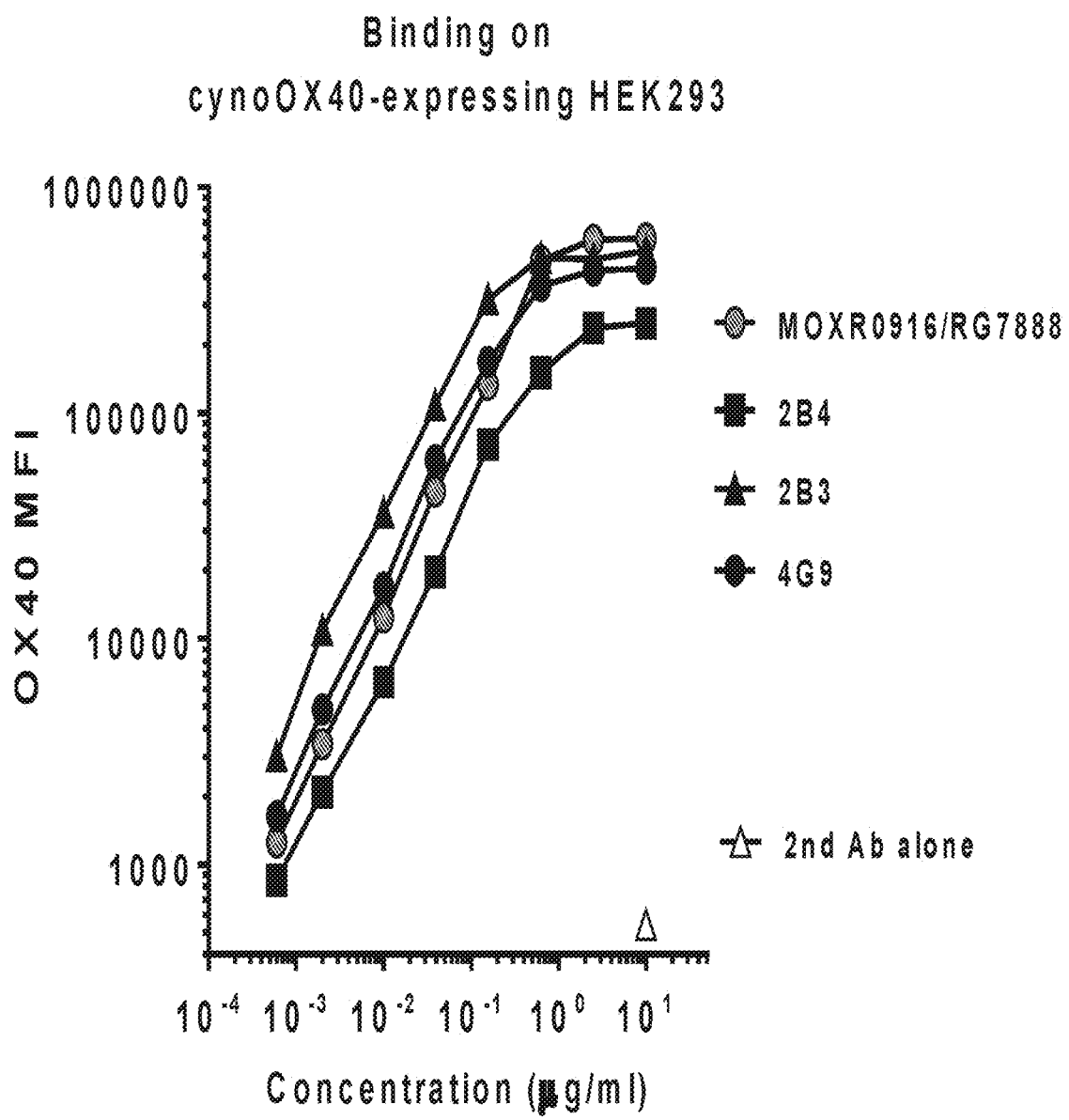
FIG. 3B shows FACS binding data of antibody clone 2B4 (WT) and two other clones with HEK293 cells (human embryonic kidney cells).
Figure 3C:
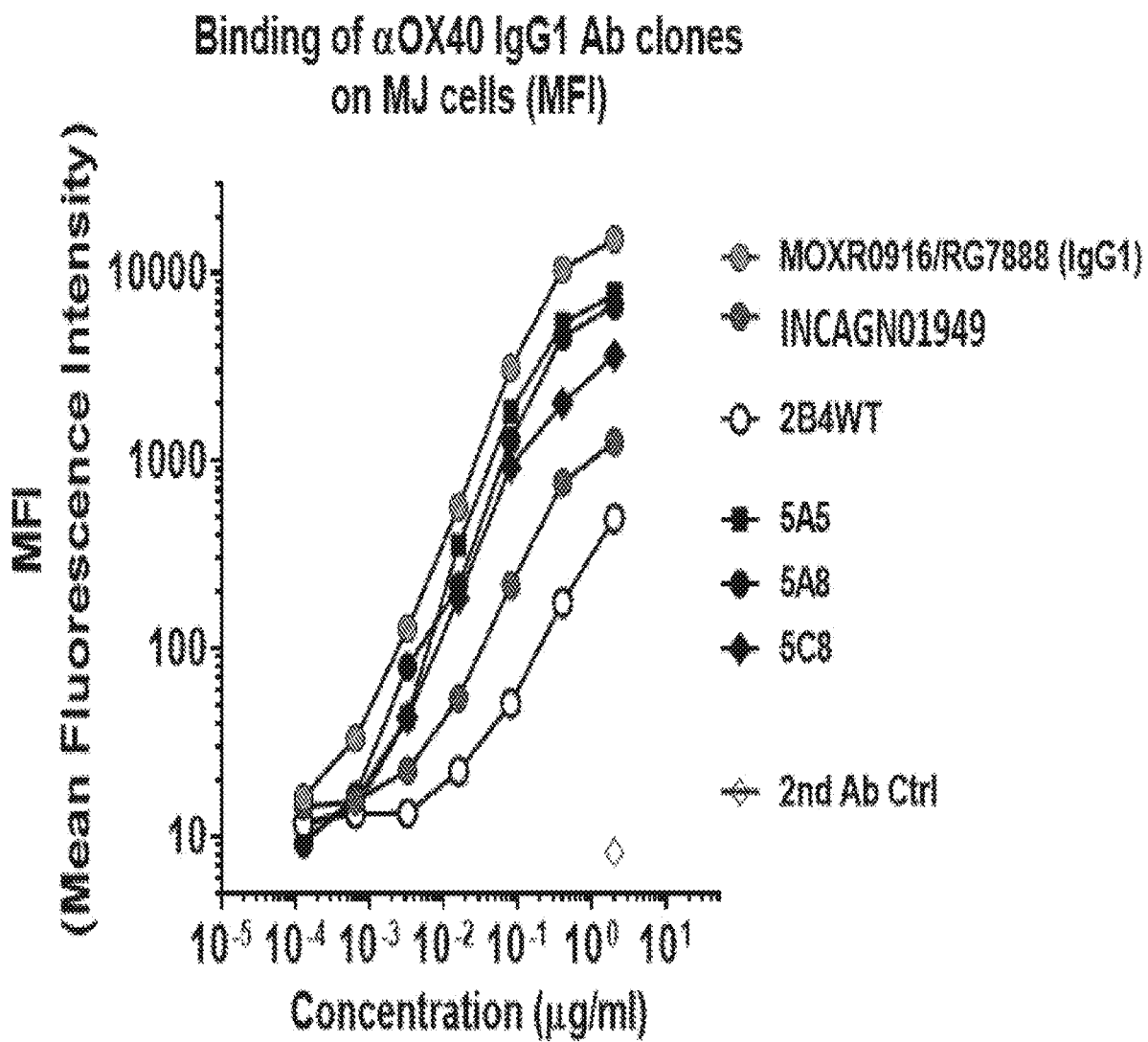
FIG. 3C shows a comparative cell binding activity of 2B4 affinity-optimized anti-OX40 antibody clones 5A5, 5A8 and 5C8, and competitor anti-OX40 clone from Genentech (MOXR0916/RG7888) on human OX40-expressing cell lines. Dose-dependent binding tested on human OX40-expressing MJ cells. All three variant clones exhibit better cell binding than wild type 2B4 clone.
Figure 3D:
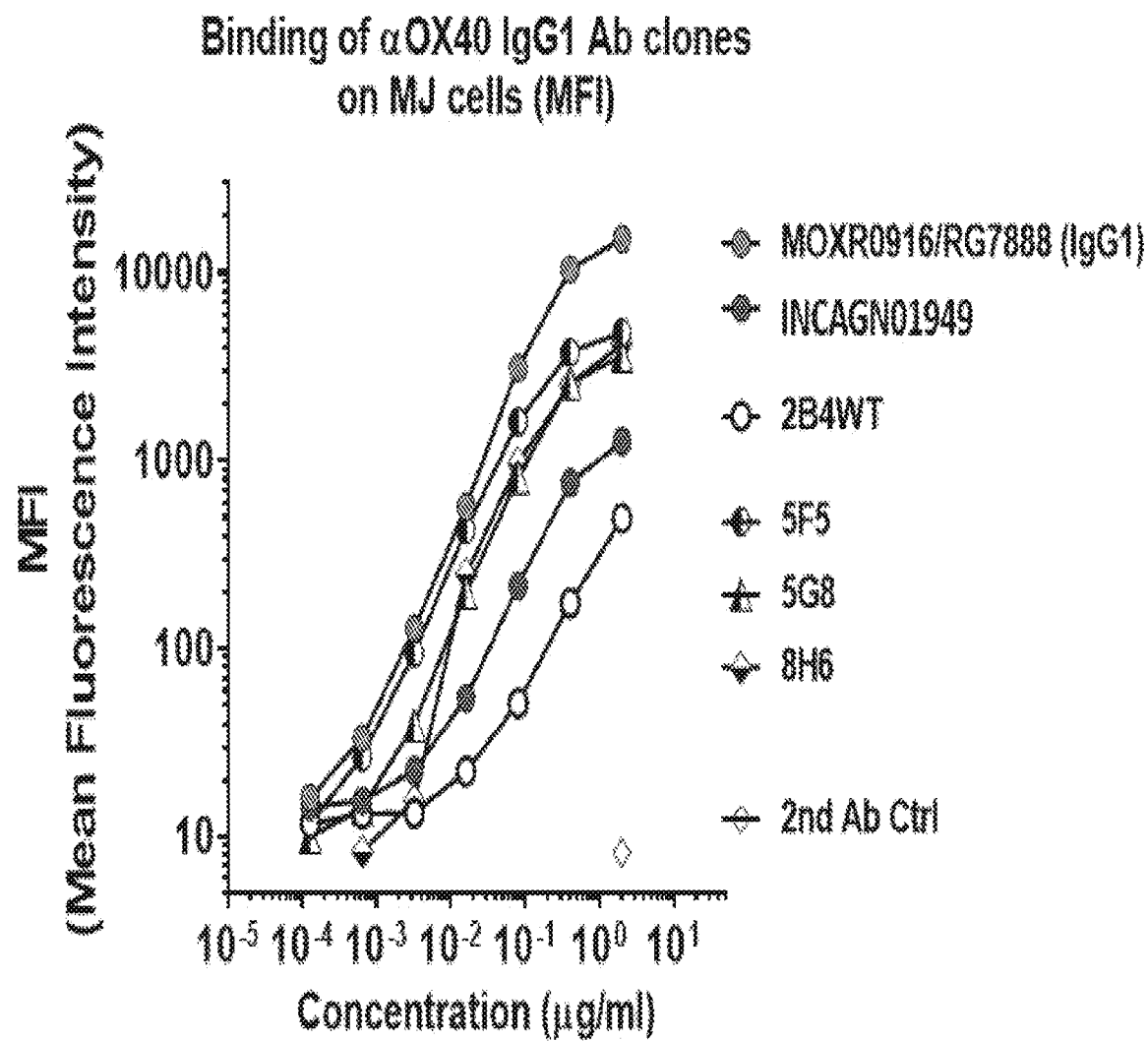
FIG. 3D shows a comparative cell binding activity of 2B4 affinity-optimized anti-OX40 antibody clones 5F5, 5G8 and 8H6, and competitor anti-OX40 clone from Genentech (MOXR0916/RG7888) on human OX40-expressing cell lines. Dose-dependent binding tested on human OX40-expressing MJ cells. All three variant clones exhibit better cell binding than wild type 2B4 clone.

The variant anti-OX40 antibodies exhibit better binding to membrane-bound human OX40 (cells expressing OX40) compared to the wild type 2B4 and INCAGN01949 antibody (from Agenus) (FIGS. 3C and D).

Figure 4A:
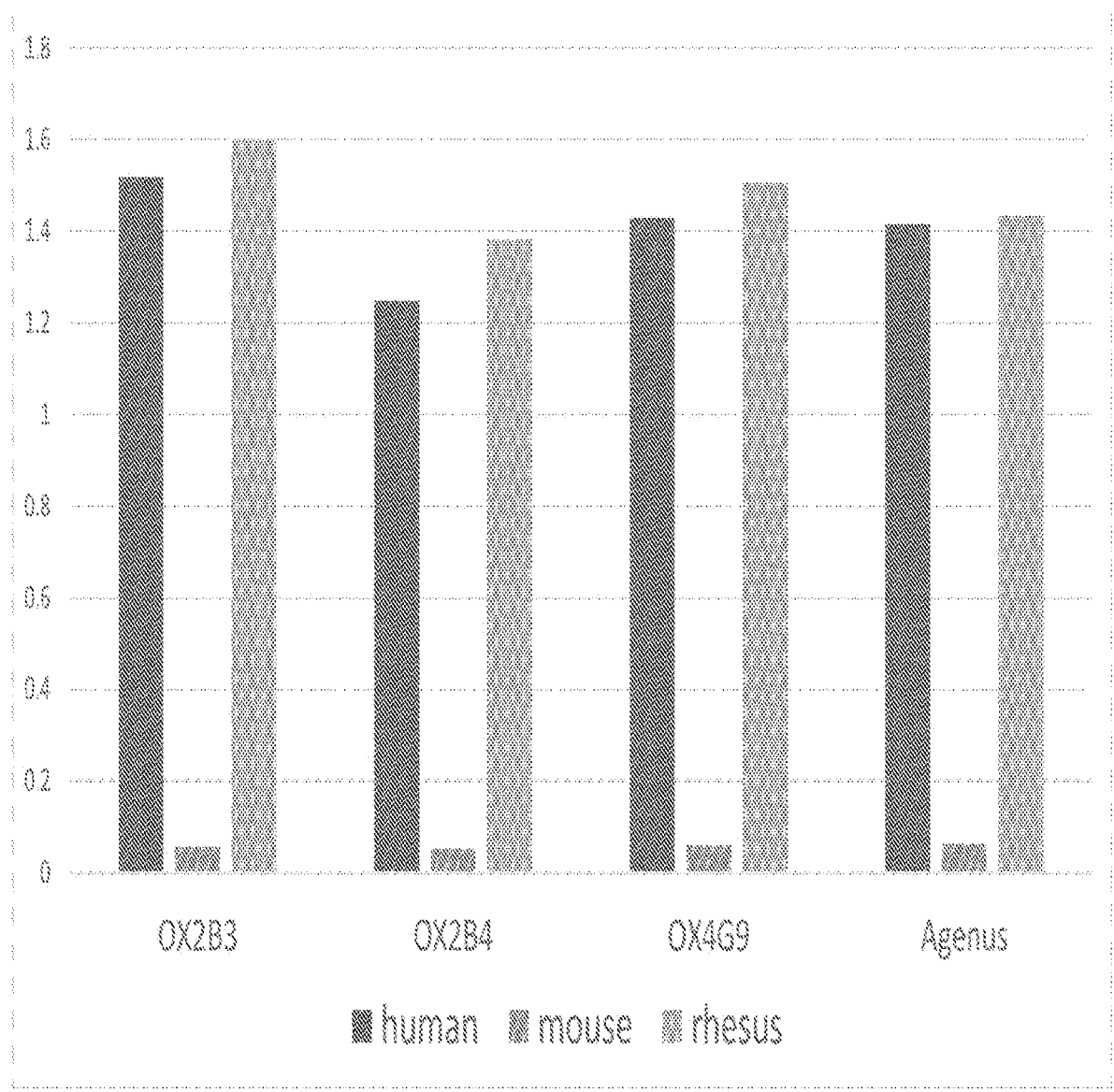
FIG. 4A shows binding cross-reactivity from an ELISA assay comparing INCAGN01949, 2B4(WT) and two other clones.
Figure 4B:
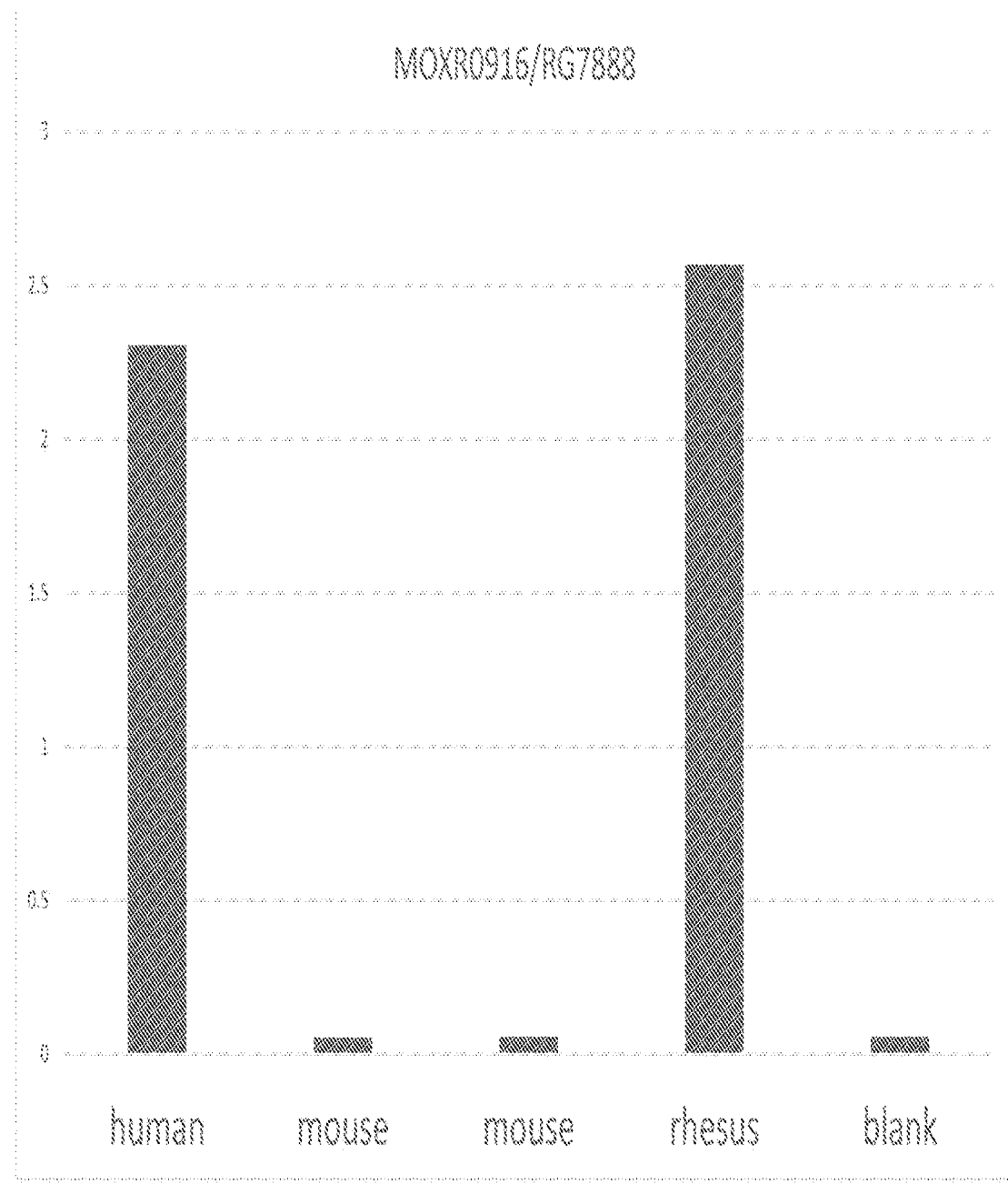
FIG. 4B shows binding cross-reactivity from an ELISA assay of MOXR0916/RG7888.

In one embodiment, the wild type 2B4 anti-OX40 antibody and two other wild type anti-OX40 antibodies exhibit cross-reactivity as they bind human OX40 and cynomolgus OX40 but do not bind mouse OX40 (FIG. 4A).

The variant anti-OX40 antibodies exhibit improved agnostic capabilities compared to INCAGN01949 (Agenus), including enhanced CD3-mediated proliferation of T cells, increased IFNγ production in OX40-expressing human T cells, and enhanced IFNγ production. The variant anti-OX40 antibodies are agnostic antibodies that increase CD4+ effector T cell proliferation and increase cytokine production by CD4+ effector T cell cells, compared to wild type 2B4 antibody and compared to INCAGN01949 (Agenus).

Figure 5A:
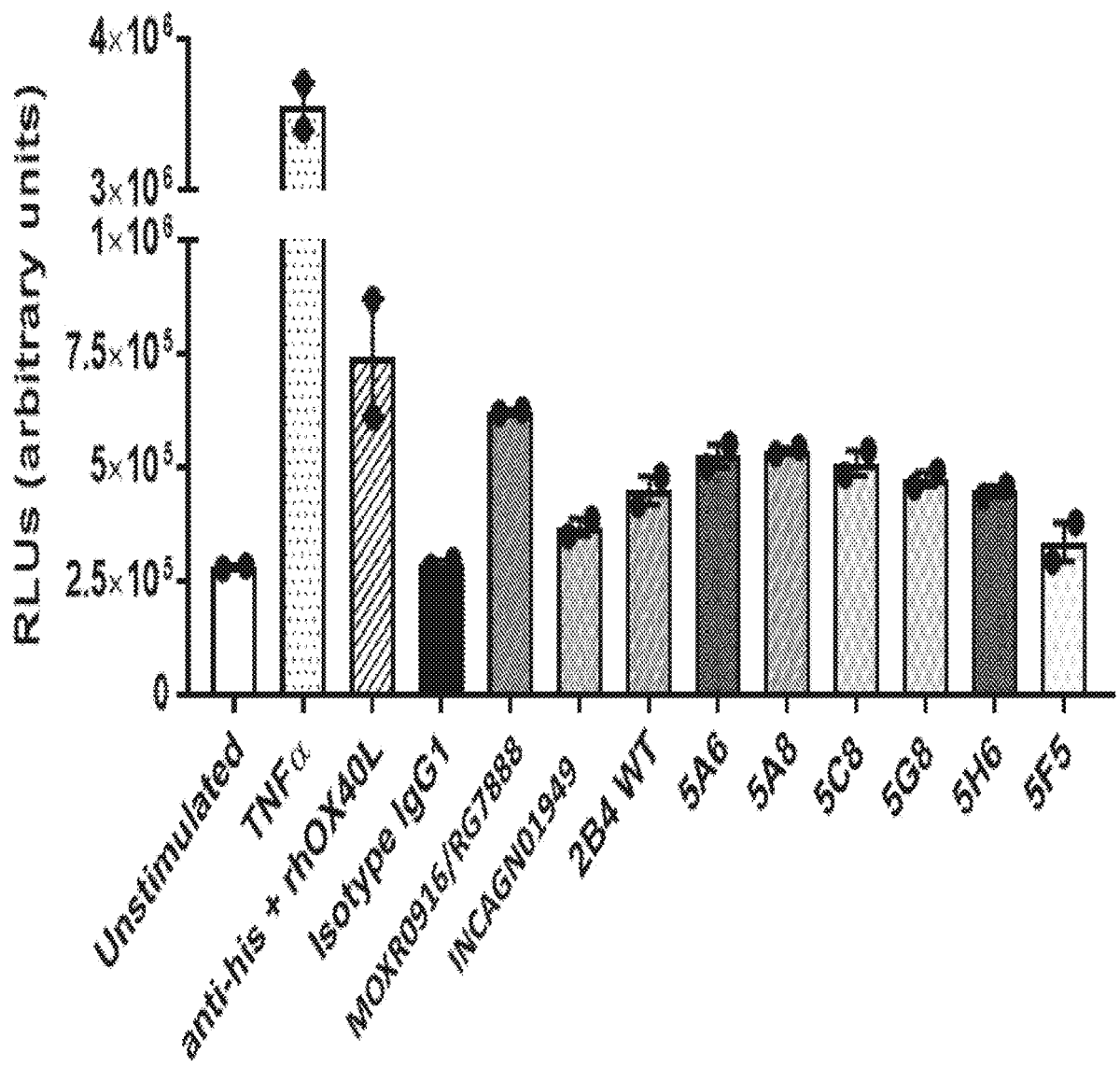
FIG. 5A shows a comparison of the six variant clones (5A6, 5A8, 5C8, 5G8, 5H6 and 5F5), wild type 2B4 clone, Genentech (MOXR0916/RG7888) and Agenus (INCAGN01949) antibodies to evaluate the ability of anti-OX40 antibodies to activate the NFkB signaling pathway on human OX40-expressing cell lines at 10 µg/ml antibody concentration (plate-bound assay).

The variant anti-OX40 antibodies induce nuclear factor kappa B (NFkB) signal transduction in a target cell expressing OX40, as detected by monitoring NFkB signaling. Several of the variant anti-OX40 antibodies are more effective in activating NFkB signaling pathway in human OX40-expressing cell lines compared to wild type 2B4 and INCAGN01949 antibody (from Agenus) (FIG. 5A; plate-bound assay).

Figure 6A:
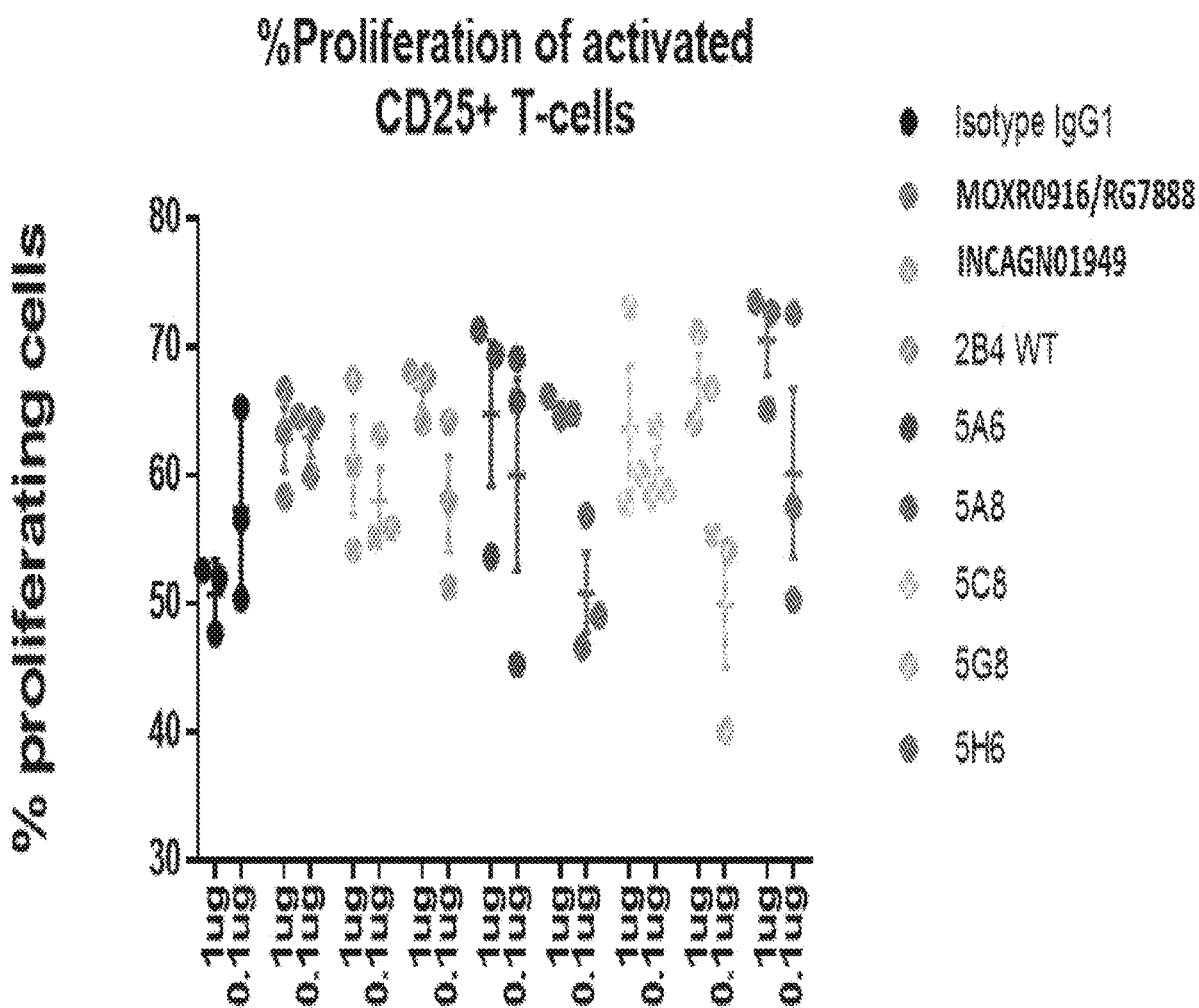
FIG. 6A shows a comparison of the six anti-OX40 variants, parent 2B4, Genentech (MOXR0916/RG7888) and Agenus (INCAGN01949) antibodies to increase CD3-mediated activation of primary human T cells by inducing a co-stimulatory (agonist) signal at 10 µg/ml antibody concentration. The graph shows from left to right along the X-axis: isotype IgG1, MOXR0916/RG7888, INCAGN01949, 2B4 (WT), 5A6, 5A8, 5C8, 5G8 and 5H6.

The variant anti-OX40 antibodies induce CD3-mediated proliferation of CD25-expressing T cells at a level comparable to MOXR0916/RG78888 (Genentech), and at a greater level compared to wild type 2B4 and INCAGN01949 (Agenus) antibodies (FIGS. 6A and B).

Figure 6B:
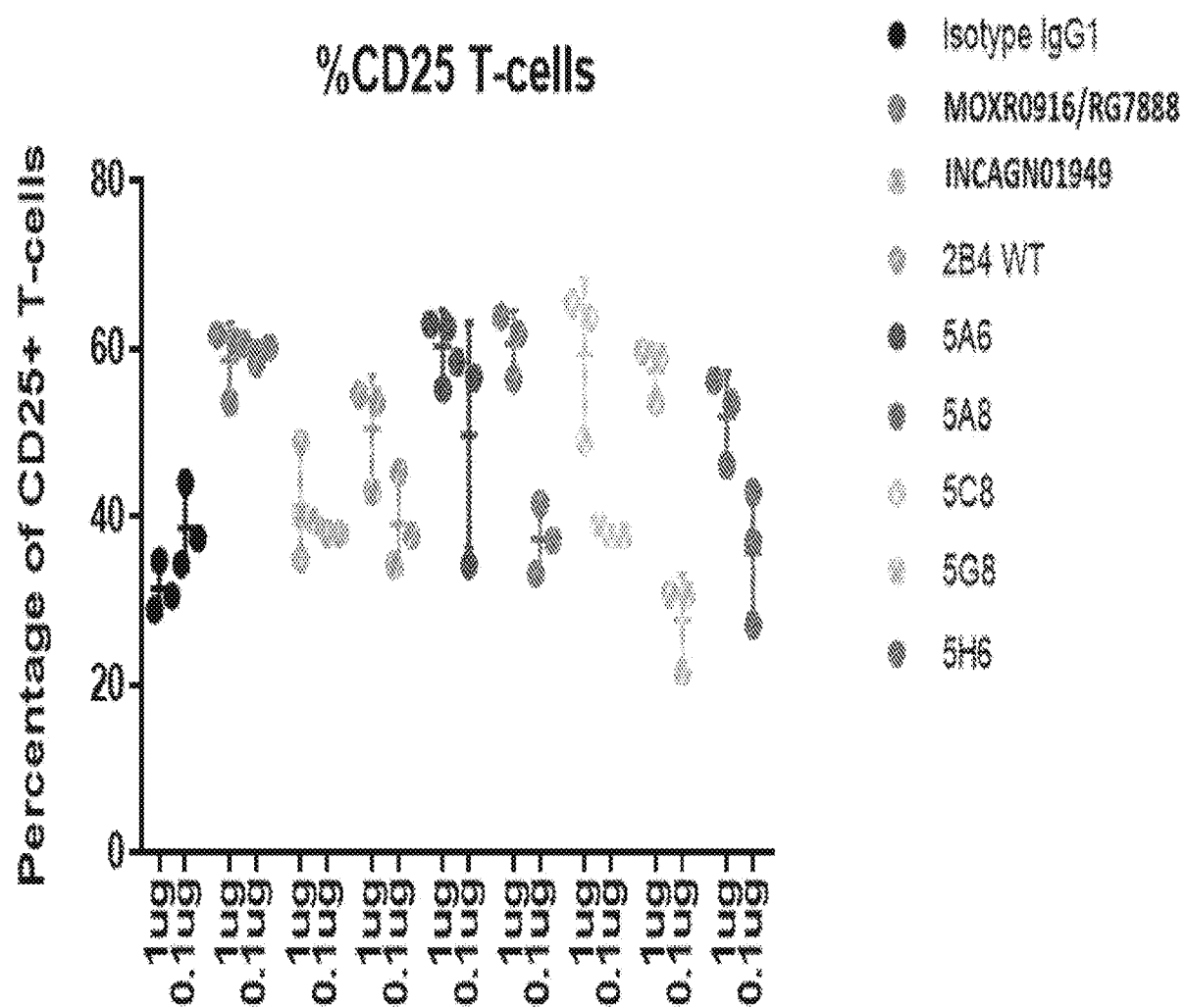
FIG. 6B shows a comparison of the six anti-OX40 variants to parent 2B4, Genentech (MOXR0916/RG7888) and Agenus (INCAGN01949) to increase CD3-mediated activation of primary human T cells by inducing a co-stimulatory (agonist) signal at 10 µg/ml antibody concentration. The graph shows from left to right along the X-axis: isotype IgG1, MOXR0916/RG7888, INCAGN01949, 2B4 (WT), 5A6, 5A8, 5C8, 5G8 and 5H6.
Figure 6C:
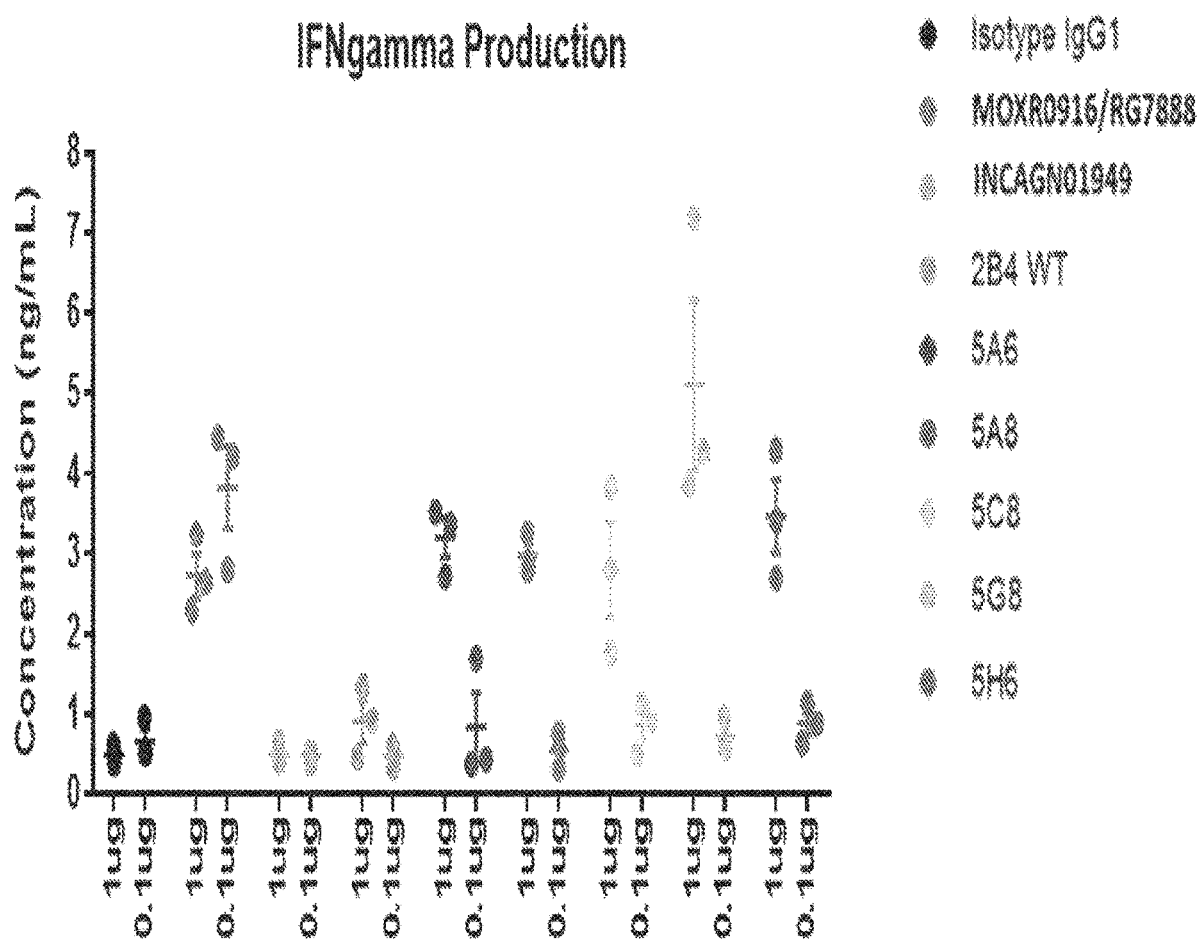
FIG. 6C shows a comparison of the six anti-OX40 variants to parent 2B4, Genentech (MOXR0916/RG7888) and Agenus (INCAGN01949) to increase CD3-mediated activation of primary human T cells by inducing a co-stimulatory (agonist) signal at 10 µg/ml antibody concentration. The graph shows from left to right along the X-axis: isotype IgG1, MOXR0916/RG7888, INCAGN01949, 2B4 (WT), 5A6, 5A8, 5C8, 5G8 and 5H6.

In a CD3-mediated T cell activation assay, the variant anti-OX40 antibodies induce IFNγ production at a higher level compared to wild type 2B4 and INCAGN01949 antibodies (FIG. 6C). Two of the variant clones, 5A6 and 5G8, induced IFNγ production at a level that is comparable to MOXR0916/RG7888 antibody (FIG. 6C).

Figure 7:
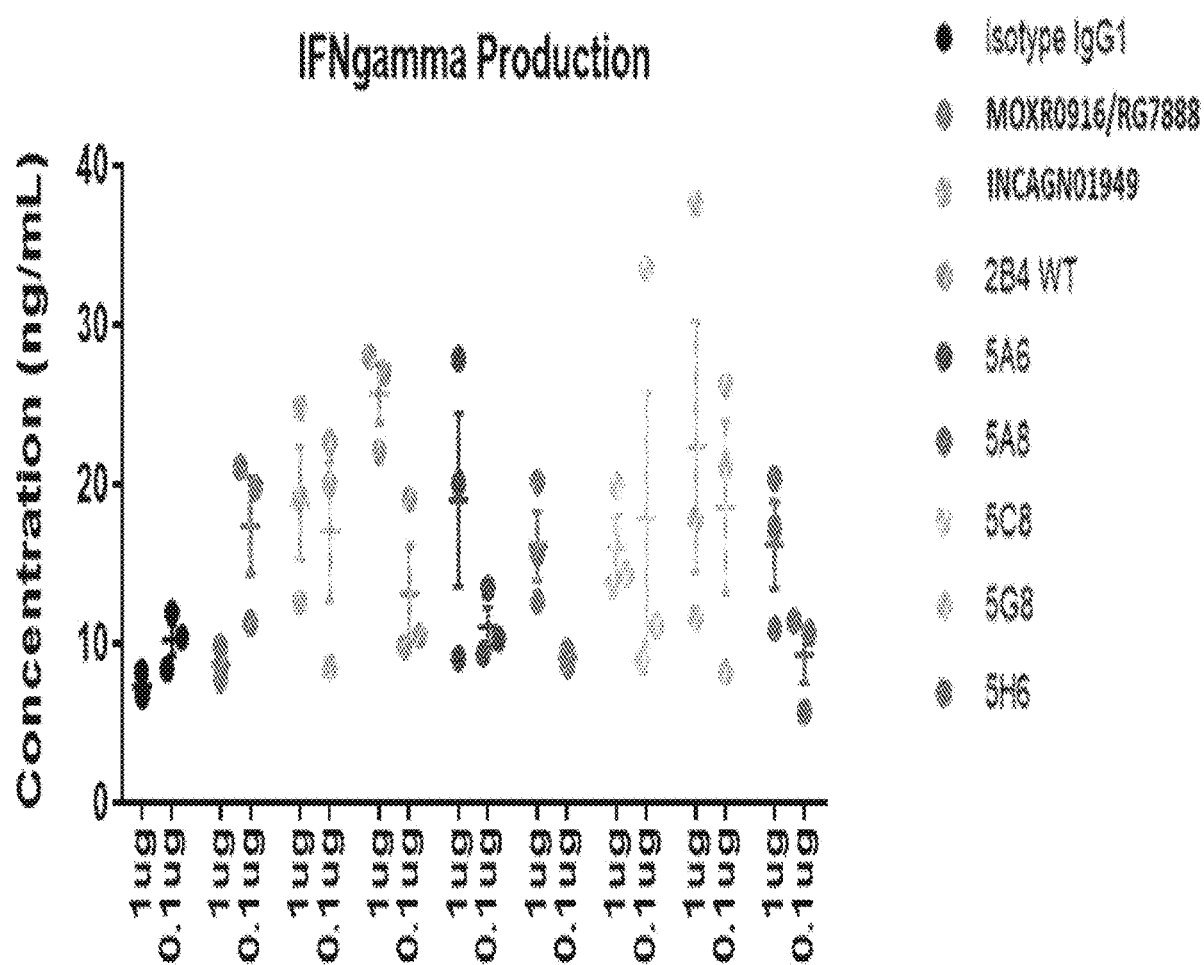
FIG. 7 shows a comparison of the five anti-OX40 variants to parent 2B4, Genentech (MOXR0916/RG7888) and Agenus (INCAGN01949) in a 3-way MLR Assay (plate-bound format) at 10 µg/ml antibody concentration. This assay evaluates the agonist activity of plate-bound optimized 2B4-variant clones using a human 3-way MLR assay. The graph shows from left to right along the X-axis: isotype IgG1, MOXR0916/RG7888, INCAGN01949, 2B4 (WT), 5A6, 5A8, 5C8, 5G8 and 5H6.

The variant anti-OX40 antibodies induce IFNγ production in at a level comparable to MOXR0916/RG78888 (Genentech), and at a greater level compared to INCAGN01949 (Agenus) and wild type 2B4 as demonstrated in a 3-way mixed lymphocyte reaction assay (plate-bound format) (FIG. 7).

Figure 10A:
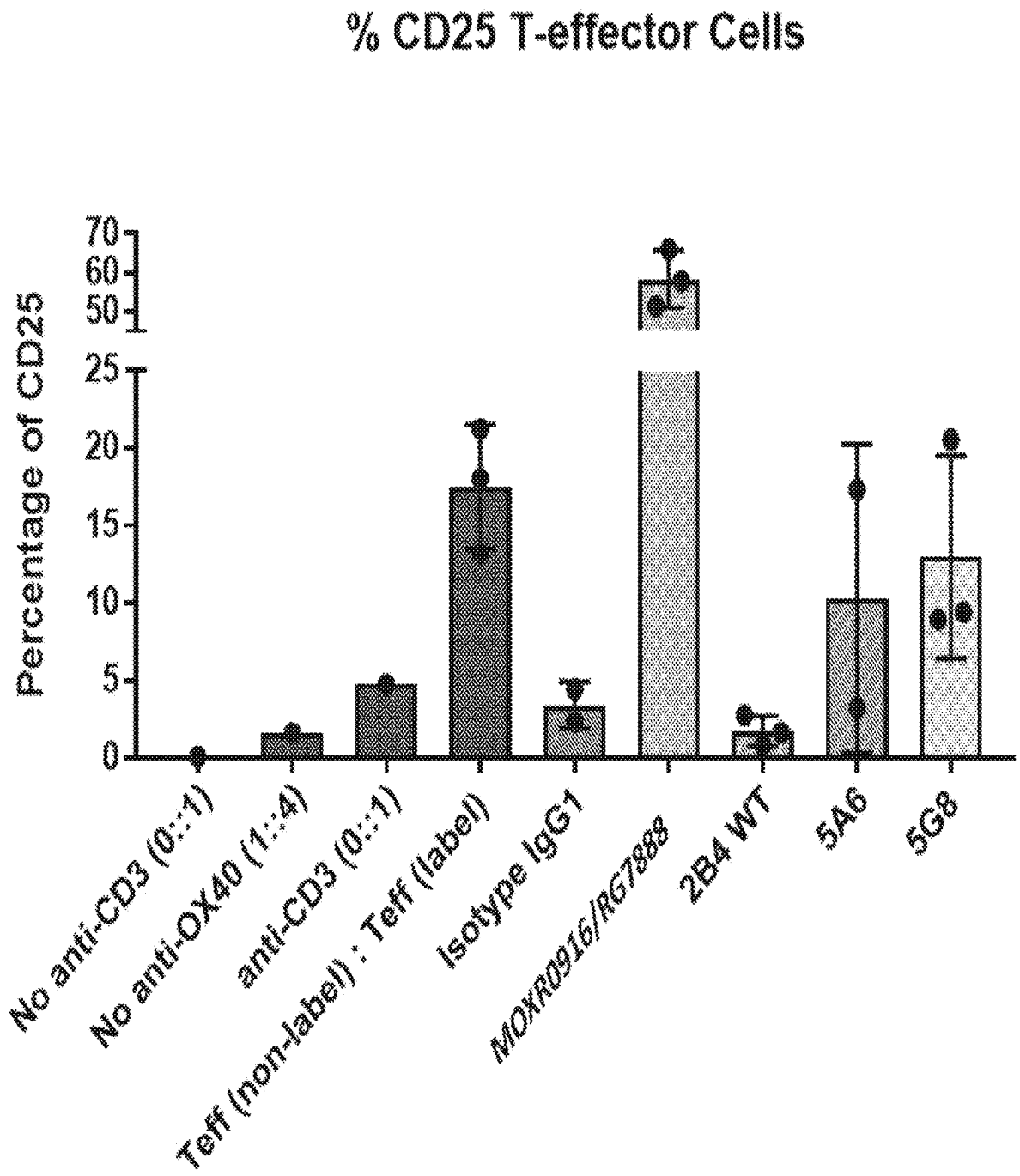
FIG. 10A shows the percentage of CD25 cells detected in a Treg suppression assay comparing MOXR0916/RG7888, 2B4(WT) and two variant clones, 5A6 and 5G8.
Figure 10B:
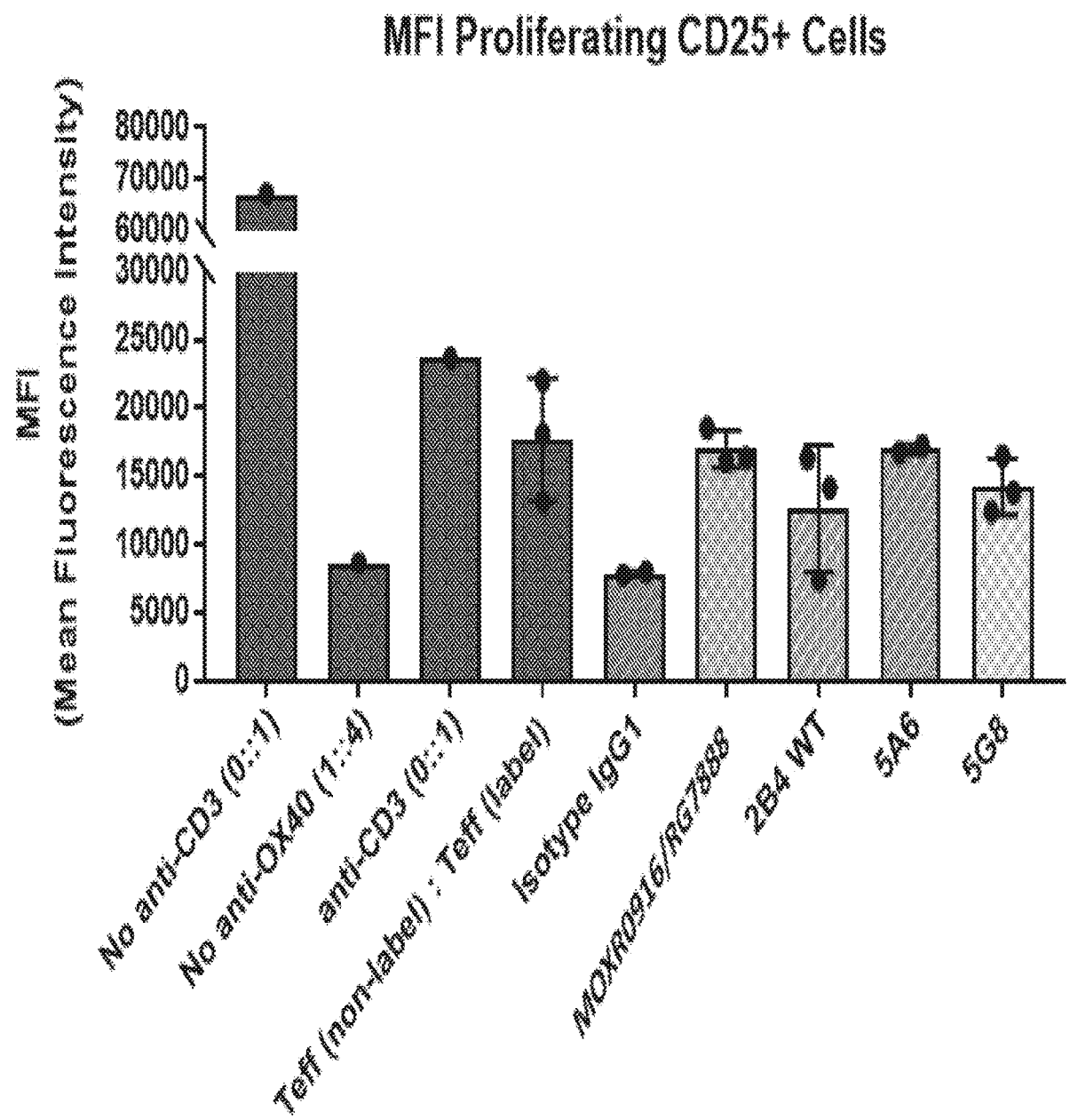
FIG. 10B shows the results of a Treg suppression assay comparing MOXR0916/RG7888, 2B4(WT) and two variant clones, 5A6 and 5G8.

Two of the variant anti-OX40 antibodies promoted the proliferative capacity of Teff cell in the presence of Treg cells. In particular the variant antibodies 5A6 and 5G8 exhibited improved activity compared to 2B4 wild type clone (FIGS. 10A and B).

EXAMPLES

The following examples are meant to be illustrative and can be used to further understand embodiments of the present disclosure and should not be construed as limiting the scope of the present teachings in any way.

Example 1

ELISA binding assays were conducted using wild type 2B4 and variant anti-OX40 antibodies. A table showing the resulting IC50 is also shown (FIG. 1).

A high binding half-area plate was coated with 20 ul per well of anti-OX40 antibody solution at a concentration of 5 ug/ml in PBS and then incubated overnight at 4° C. overnight. After washing the plate with 0.05% PBS/Tween, 100 ul of Blocker™ Casein in PBS (Thermo Fisher Catalog Number: 37523) was added to the plate. The plates were incubated for one hour at room temperature. Then human OX40 antigen dilutions were added and incubated for one hour at room temperature. The plate was washed again with 0.05% PBS/Tween and incubated with 50 ul of Jackson Immuno Research Peroxidase AffiniPure Goat Anti-Human IgG, Fcγ Fragment (Catalog Number: 109-035-098) for one hour at room temperature. After washing, the plate was developed with 1-Step™ Ultra TMB-ELISA Substrate Solution (Thermo Fisher Catalog Number:34028). The plate was read in the FlexStation 3 at OD 450.

The variant anti-OX40 antibodies (5A6, 5A8, 5C8, 5F5, 5G8 and 5H6) exhibit better binding capabilities to human OX40 compared to the wild type 2B4 antibody, and exhibit an IC50 that is at least one order of magnitude lower than the IC50 of wild type B24 antibody as measured by an ELISA assay (see FIG. 1 and the table at FIG. 1).

Example 2

Binding affinity studies were conducted using surface plasmon resonance (SPR) analysis (FIGS. 2A-J). Antibodies analyzed included wild type 2B4 antibody, six different variant anti-OX40 antibodies, and MOXR0916/RG7888 antibody (Genentech).

Kinetic interactions between antibodies and human OX40 proteins were measured at 25° C. using Biacore T200 surface plasmon resonance (GE Healthcare). Anti-human fragment crystallizable region (Fc region) antibody was immobilized on a CM5 sensor chip to approximately 8000 resonance units (RU) using standard N-hydroxysuccinimide/N-Ethyl-N'-(3-dimethylaminopropyl) carbodiimide hydrochloride (NHS/EDC) coupling methodology. The anti-OX40 antibody (2 μg/mL) was captured for 60 seconds at a flow rate of 10 μL/minute. Recombinant human OX40/His was serially diluted in a running buffer of 0.01 M HEPES pH 7.4, 0.15 M NaCl, 3 mM EDTA, 0.05% v/v Surfactant P20 (HBS-EP+). All measurements were conducted in HBS-EP+ buffer with a flow rate of 30 μL/minute. A 1:1 (Langmuir) binding model was used to fit the data.

The variant anti-OX40 antibodies (5A6, 5A8, 5C8, 5F5, 5G8 and 5H6) exhibit binding affinities that are about two orders of magnitude better when binding to human OX40 compared to wild type 2B4 antibody. The variant antibodies exhibit overall improved affinity and binding kinetics compared to wild type 2B4 as demonstrated by surface plasmon resonance (SPR) analysis (FIGS. 2A-J). All of the variant anti-OX40 antibodies bind to human OX40 with a $K_d$ of less than $5 \times 10^{-9}$ M (see the table at FIG. 2H) which is comparable to the $K_d$ of MOXR0916/RG7888 (Genentech) (see table at FIG. 2J).

Example 3

FACS binding studies were conducted using cells expressing OX40 and anti-OX40 antibodies. Anti-OX40 antibodies analyzed include: wild type 2B4 (FIGS. 3A-D), wild type 2B3 and 4G9 (FIGS. 3A and B), variant anti-OX40 antibodies (FIGS. 3C and D), MO XR0916/RG7888 (Genentech), and INC AGN01949 (Agenus).

Materials: Goat αh-IgG-AF647 (Southern Biotech, cat #2040-31), FACS buffer (PBS1X, 2% FCS/FBS, 0.05% sodium azide), V-bottom 96-well plates.

Protocol: (use 4° C. cold FACS buffer throughout the staining)

Plated approximately 80K MJ or HEK cells per well in a V-bottom 96-well plate. Spun the cells at 1,500 rpm for 2 min and removed the supernatant by quickly flipping the plate. Washed the cells with 170 μl/well of FACS buffer (PBS1X+2% FCS). Spun the cells (1,500 rpm; 2 min) and removed supernatant by quickly flipping the plate.

Resuspended the cells in 80 μl/well of FACS buffer containing serial dilution of anti-OX40 antibodies (from 10 to 0.00003 μg/ml). Incubated for 20 min at 4° C. Spun the cells at 1,500 rpm for 2 min and removed the supernatant by quickly flipping the plate. Washed the cells with 170 μl/well of FACS buffer. Spun the cells (1,500 rpm; 2 min) and remove supernatant by quickly flipping the plate. Repeated the washing step twice.

Resuspended the cells in 80 μl/well of FACS buffer containing AF647-labeled anti-human IgG antibody (Southern Biotech; Cat. No. 2040-31; Lot. K471X873C) diluted 1:1,000 in FACS buffer. Incubated for 20 min at 4° C. in the dark. Spun the cells (1,500 rpm; 2 min) and removed supernatant by quickly flipping the plate. Washed the cells with 170 μl/well of FACS buffer. Spun the cells at 1,500 rpm for 2 min and removed the supernatant by quickly flipping the plate. Repeated washing steps twice.

Resuspended the cells in 80 μl of FACS buffer and analyzed using a flow cytometer. Acquired samples on the flow cytometer maximum 1 h after the end of the staining.

The variant anti-OX40 antibodies (5A6, 5A8, 5C8, 5F5, 5G8 and 5H6) exhibit better binding to membrane-bound human OX40 (cells expressing OX40) compared to the wild type 2B4 and INCAGN01949 antibody (from Agenus) (FIGS. 3C and D).

Example 4

Cross-reactivity ELISA binding analysis was conducted using human, mouse and rhesus OX40 antigen, reacted against anti-OX40 antibodies which included: wild type anti-OX40 antibodies 2B4, 2B3 and 4G9; and MOXR0916/RG7888 (Genentech) (FIGS. 4A and B).

Ni-NTA plate was captured with 50 ul per well of human, mouse, and rhesus OX40 antigen solutions at a concentration of 1 ug/ml in PBS and incubated 1 hour at room temperature. After washing the plate with 0.05% PBS/Tween, 1 ug/mL the human anti-OX40 antibodies in Blocker™ Casein in PBS (Thermo Fisher Catalog Number: 37528) were added with 50 ul per well and incubated for one hour at room temperature. The plate was washed again with 0.05% PBS/Tween and incubated with 50 ul of Jackson Immuno Research Peroxidase AffiniPure Goat Anti-Human IgG, Fcγ Fragment (Catalog Number: 109-035-098) for one hour at room temperature. After washing, the plate was developed with 1-Step™ Ultra. TMB-ELISA Substrate Solution (Thermo Fisher Catalog, Number:34028). The plate was read in the FlexStation 3 at OD 450.

Wild type anti-OX40 antibodies 2B4, 2B3 and 4G9 exhibit cross-reactivity as they bind human OX40 and cynomolgus OX40 but do not bind mouse OX40 (FIG. 4A).

Example 5

Figure 5B:
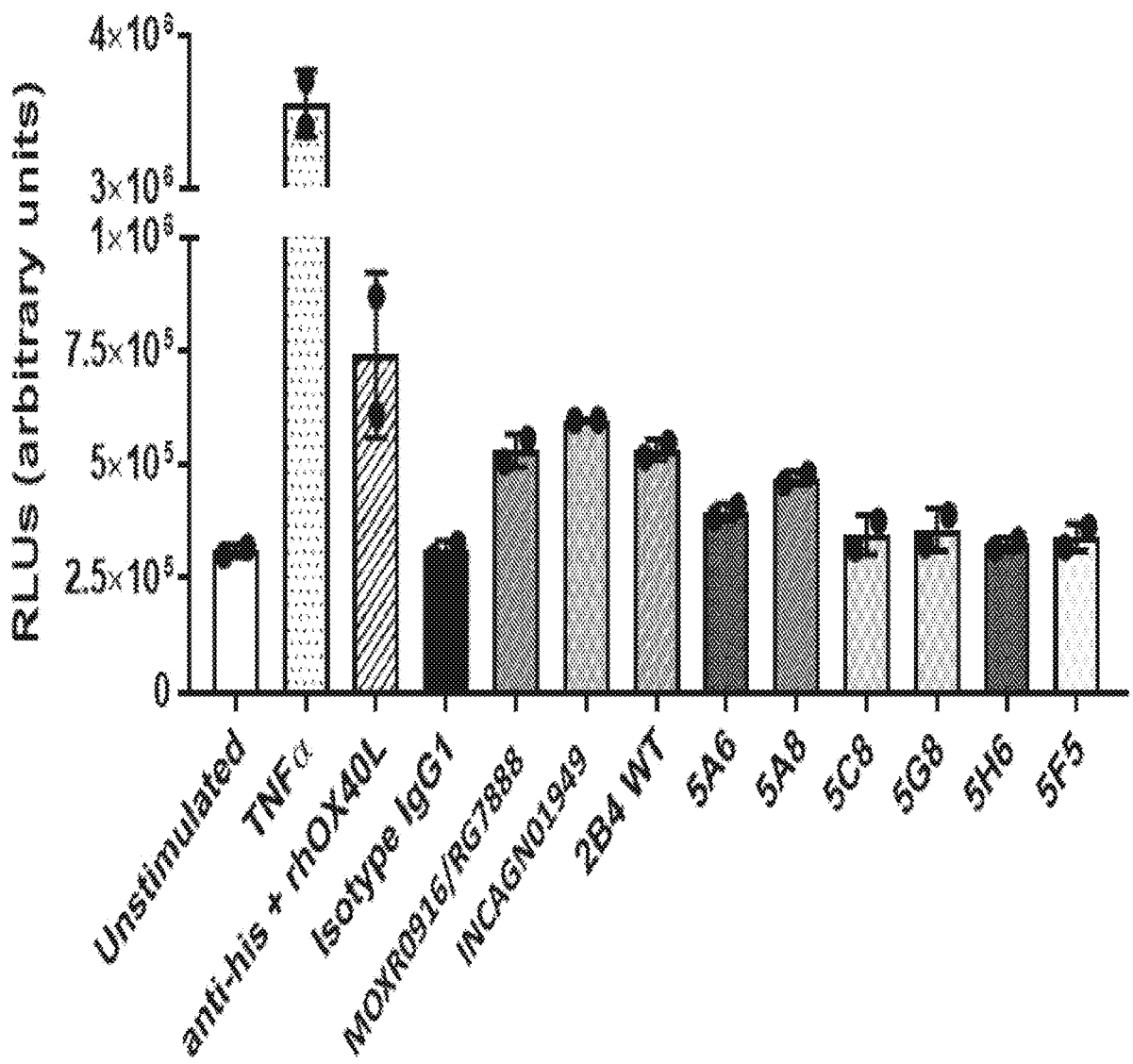
FIG. 5B shows a comparison of the six variant clones (5A6, 5A8, 5C8, 5G8, 5H6 and 5F5), wild type 2B4 clone, Genentech (MOXR0916/RG7888) and Agenus (INCAGN01949) antibodies to evaluate the ability of anti-OX40 antibodies to activate the NFkB signaling pathway on human OX40-expressing cell lines at 10 µg/ml antibody concentration (soluble assay).
Figure 5C:
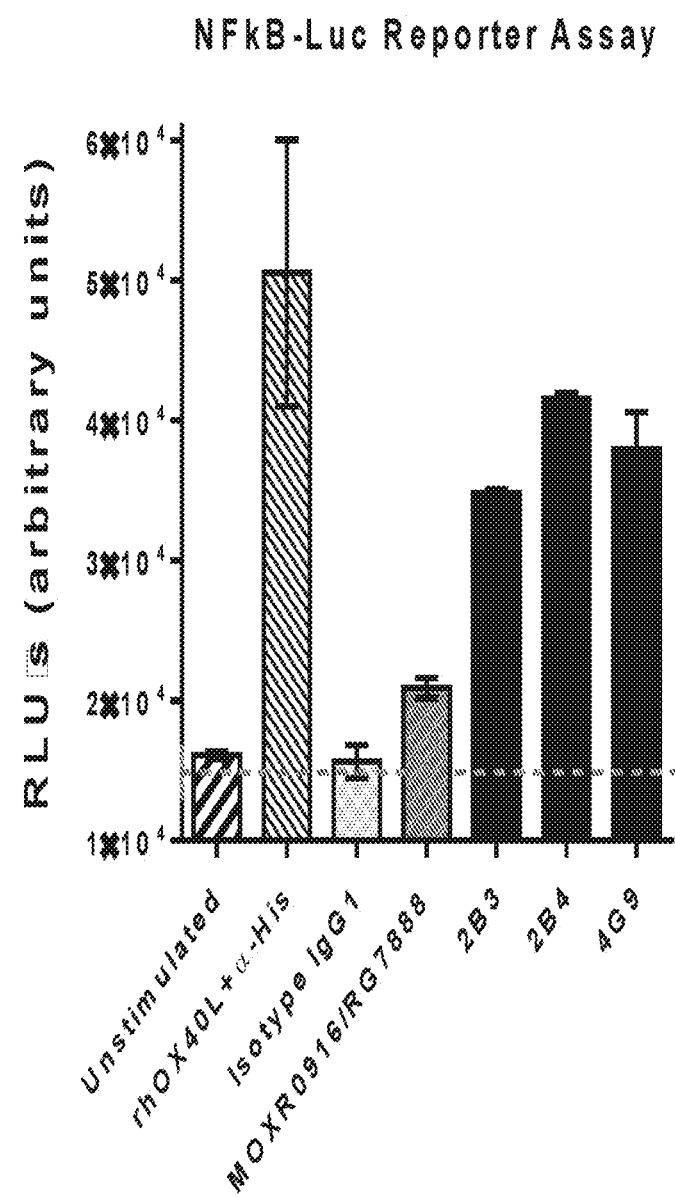
FIG. 5C shows the results of an NFκB reporter assay of MOXR0916/RG7888, clone 2B4 and two other wild type clones.

Variant anti-OX40 antibodies were tested for their ability to induce OX40-mediated signal transduction in OX40-expressing cells using an NFkB reporter assay. Anti-OX40 antibodies tested in this assay included: wild type 2B4; variant anti-OX40 antibodies 5A6, 5A8, 5C8, 5G8, 5H6 and 5F5; MOXR0916/RG7888 (Genentech); INCAGN01949 (Agenus); anti-His+rhoOX40L; and isotype IgG1. Both plate-bound (FIG. 5A) and soluble (FIGS. 5B and C) NFkB reporter assays were conducted.

Plate-bound NFkB Reporter Assay:

Cell Culture: OX40+ HEK293-NFkB-luciferase reporter stable cell line cultured in complete medium: RPMI-1640+ 10% FCS+80 ug/mL Hygromycin+0.4 ug/mL Puromycin.

Day −1 (Day Minus 1):

In a white flat-bottom 96-well microplate, diluted the isotype control and anti-OX40 antibodies (stock stored at 4° C.) to 10 μg/ml in 100 μL of DPBS 1×.

Stored at 4° C. overnight.

Day 0:

The antibody plate was prepared first.

Washed antibody plate twice with 150 µL of complete media (RPMI-1640+10% FCS).

Prepared cell plate second.

OX40+ HEK293-NFkB-luciferase reporter stable cells were counted and resuspended in the 1004, of RPMI-1640+ 20% FCS needed to plate in the following manner: distributed 1×10e5 cells per well; diluted TNFα (stock stored at −20° C.) (Biolegend) to 100 ng/mL in the 1004, of cells per well; diluted anti-Histidine (stock stored at 4° C.) (Biolegend) to 2 µg/ml in combination with diluted, purified rhOX40L (stock stored at 20° C.) (Biolegend) to 500 ng/ml in the 100 µL of cells per well.

Added 200 uL PBS to surrounding (non-sample) wells to eliminate edge-effect.

Incubated the cells overnight (for approximately 15 h) at 37° C. in 5% CO2.

Day 1:

After stimulation, the luciferase activity was revealed by adding 100 µl/well of Bio-Glo® Luciferase Assay system (Promega) to the wells containing 100 uL of cells/antibody.

The plate was incubated at room temperature in the dark for 10 min under slow shaking conditions.

The luciferase activity was obtained by reading with the FlexStation3 (Molecular Devices) (luminescence reading, 500 ms).

Soluble Format NFkB Reporter Assay:

Cell Culture: OX40+ HEK293-NFkB-luciferase reporter stable cell line cultured in complete medium: RPMI-1640+ 10% FCS+80 ug/mL Hygromycin+0.4 ug/mL Puromycin.

Day 0:

Prepare Cell Plate First:

OX40+ HEK293-NFkB-luciferase reporter stable cells were counted and resuspended in the volume of RPMI-1640+20% FCS needed to plate in the following manner: in a white flat-bottom 96-well microplate, distributed 1×10e5 cells per well in a 50 µl volume (in duplicate); kept plate at 37° C. until antibody plate has been prepared (step 2).

Prepare Antibody Plate Second:

In an ultra-low attachment U-bottom well plate (Corning), the reagents below are diluted in RPMI-1640 (no FCS):

a) Diluted TNFα (stock stored at −20° C.) (Biolegend) to 100 ng/mL.

b) Diluted anti-Histidine (stock stored at 4° C.) (Biolegend) to 2 µg/ml in combination with diluted, purified rhOX40L (stock stored at 20° C.) (Biolegend) to 500 ng/ml.

c) Diluted the isotype control and anti-OX40 clones (stock stored at 4° C.) to 20 µg/ml (for a final concentration of 10 µg/mL).

Distributed 50 uL of each antibody into each well of the prepared cell plate (total volume per well is now 100 uL). Added 200 uL PBS to surrounding (non-sample) wells to eliminate edge-affect. Incubated the cells overnight (for approximately 15 h) at 37° C. in 5% CO2.

Day 1:

After stimulation, the luciferase activity was revealed by adding 100 µl/well of Bio-Glo® Luciferase Assay system (Promega) to the wells containing 100 uL of cells/antibody.

The plate was incubated at room temperature in the dark for 10 min under slow shaking conditions.

The luciferase activity was obtained by reading with the FlexStation3 (Molecular Devices) (luminescence reading, 500 ms).

The variant anti-OX40 antibodies exhibit improved agnostic capabilities compared to INCAGN01949 (Agenus), including enhanced CD3-mediated proliferation of T cells, increased IFNγ production in OX40-expressing human T cells, and enhanced IFNγ production. The variant anti-OX40 antibodies are agnostic antibodies that increase CD4+ effector T cell proliferation and increase cytokine production by CD4+ effector T cell cells, compared to wild type 2B4 antibody and compared to INCAGN01949 (Agenus) (FIG. 5A).

The variant anti-OX40 antibodies induce nuclear factor kappa B (NFkB) signal transduction in a target cell expressing OX40, as detected by monitoring NFkB signaling. Several of the variant anti-OX40 antibodies (5A6, 5A8 and 5C8) are more effective in activating NFkB signaling pathway in human OX40-expressing cell lines compared to wild type 2B4 and INCAGN01949 antibody (from Agenus) (FIG. 5A; plate-bound assay).

Example 6

Figure 6D:
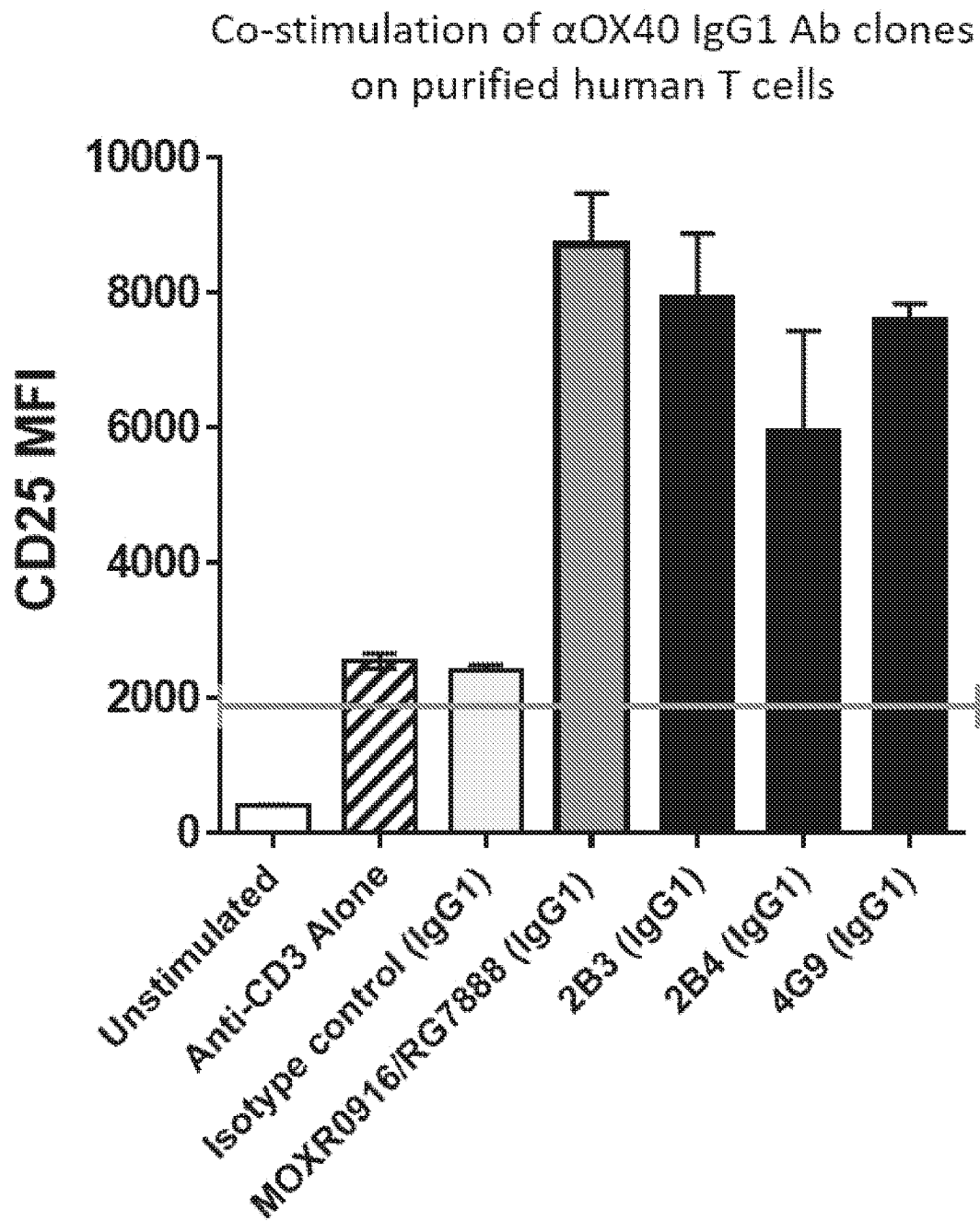
FIG. 6D shows results of a CD3-mediated T-cell activation assay comparing MOXR0916/RG7888, clone 2B4 and two other clones.

Variant anti-OX40 antibodies were tested for their ability to induce CD3-mediated activation of primary human T cells by inducing a co-stimulatory (agonist) signal. T cell activation assays were conducted using wild type 2B4 antibody; variant anti-OX40 antibodies 5A6, 5A8, 5C8, 5G8, 5H6 and 5F5; MOXR0916/RG7888 (Genentech); INCAGN01949 (Agenus); and isotype IgG1. Both soluble format (FIGS. 6A-C) and plate-bound (FIG. 6D) assays were conducted. CD25+ T cells were detected (see FIGS. 6A, B and D) and gamma-interferon production was detected (see FIG. 6C).

T cell Activation Assay with Detection of CD25+ T Cells:

Day −1 (Day Minus 1):

Diluted αCD3 to 2 ug/mL in 50 uL volume per well of DPBS 1×.

Diluted anti-OX40 antibodies in the diluted αCD3 (from step above) to 20 µg/mL and 2 µg/mL (or 1 µg and 0.1 of antibody per well).

Coated a U-bottom 96-well plate in triplicate (50 uL per well).

Covered the plate with plastic film and incubate overnight at 4° C.

Day 0:

Labeled purified human T cells using the Cell Proliferation Dye eFluor 670 (eBioscience).

Resuspended from 10×10e6 up to 100×10e6 cells in 1.5 ml of sterile pre-warmed PBS-0.1% BSA and add 1.5 µl of dye eFluor 670 in DMSO (stock stored at −20° C.).

Vortexed and incubated in aluminum foil for 10 min at a 37° C. water bath.

Quenched the staining by adding 12 ml of ice-cold complete medium (RPMI1640+10% FCS+Pen/Strep), mix and spin the cells at 1350 RPM for 5 min.

Washed the cells by resuspending in 12 ml of fresh complete medium, mix and spin the cells at 1350 RPM for 5 min.

Purified human T cells were counted using the Ready-Probes® Cell Viability Imaging Kit, Blue/Red (Thermo Fisher). Placed 50 µl of cells in a 450 µl DPBS 1× in an Eppendorf™ tube and added 1 drop of each reagent (blue and red). Mixed by vortexing and incubated at room temperature for 5 min. Counted the cells using the Countess II-FL cell counter (Alive cells=DAPI (blue)–PI (red) cell counts).

The pre-coated U-bottom plate (from day −1) were washed three time by using 150 µl of sterile complete medium per well under a sterile hood.

Resuspended labeled purified T-cells in complete medium to plate 2×10e4 cells/well in a 200 µl volume per well.

The plate was incubated at 37° C. for 4 days.

Day 4:

On day 4, the cells were transferred into a V-bottom 96-well plate.

Spun the cells at 1350 RPM for 5 min.

100 μl of supernatant per well were collected and stored at −80° C. to measure cytokines levels.

Cells are washed twice with cold FACS buffer (DPBS 1×+2% FCS) and stained with PE-labelled anti-human CD25 (clone M-A251) at 5 μl/well in 80 μl of FACS buffer for 20 min at 4° C.

Spun the cells at 1500 RPM for 2 min and remove the supernatant by quickly flipping the plate.

Washed the cells with 170 μl/well of FACS buffer. Spun the cells at 1500 RPM for 2 min and remove the supernatant by quickly flipping the plate. Repeat the washing step twice.

Resuspended the cells in 150 μl/well of FACS buffer and analyzed by Flow.

Acquired samples not later than 1 h after the end of the staining otherwise fix the cells using 150 ul of fixation buffer (Biolegend) and stored in aluminum foil at 4° C.

T Cell Activation Assay with Detection of INFγ:

Materials:

Proinflammatory panel 1 (human) kit (Meso Scale Discovery-MSD).

Protocol:

1) Thawed supernatant samples (from T cell activation assay described above) in a sterile cell culture incubator (37° C., 5% CO2).

2) Prepared tubes for standard:

a) Using Calibrator 1 (MSD kit), added 1000 uL of Diluent 2 (MSD kit) to the lyophilized calibrator vial (MSD kit).

b) Inverted at least 3 times (Do Not Vortex).

c) Let the solution equilibrate to room temperature for 15 minutes.

d) Prepared a 1:4 dilution according to kit manual instructions by transferring 100 uL of the highest calibrator to 300 uL of Diluent 2, mixed well. Repeated 4-fold serial dilutions 5 additional times to generate 7 calibrators (vortexed Eppendorf™ tube before transferring the 100 uL) (100 uL calibrator: 300 uL diluent 2).

3) Prepared dilution for supernatant samples to 1:5×:

a) In the first round-bottom plate, added 40 uL of supernatant sample to 60 uL of complete media (RPMI 1×+10% FBS) into the wells (1:2.5× dilution).

b) In a second round-bottom plate, added 50 uL of the 1:2.5× diluted sample into 50 uL of diluent two (MSD kit) into the wells (this dilution is a 1:2× with a final total dilution of samples at 1:5×).

4) Washed the MSD Plate 3 times with 300 uL/well of 1×KPL wash buffer.

5) Added 50 uL of standard samples (from step 2) as well as the 1:5× diluted samples (from step 3) (1:5× diluted samples) onto the washed MSD plate.

6) Sealed the plate with an adhesive plate seal and incubated at room temperature with shaking for 2 hours.

7) Prepared the detection antibody solution:

a) For one plate added 60 μL of SULFO-TAG Anti-hu IFN-γ detection antibody (MSD kit) to 2.94 mL of diluent 3 (total final volume of 3 mL).

8) Without pouring out the samples, washed the plate 3 times with 300 uL/well of 1× KPL wash buffer.

9) Added 25 uL of detection antibody cocktail solution to each well.

10) Sealed the plate with an adhesive plate seal and incubated at room temperature with shaking for 2 hours.

11) Prepared a 2× Read Buffer (prepare a 1:2× dilution of the 4× read buffer in the MSD kit in cell culture grade H2O).

12) Washed the MSD Plate 3 times with 300 uL/well of 1×KPL wash buffer.

13) Added 25 uL of read buffer (MSD kit) to each well.

14) Analyzed the plate on an MSD plate reader (waited no more than one hour to read after adding read buffer).

The variant anti-OX40 antibodies induce CD3-mediated proliferation of CD25-expressing T cells at a level comparable to MOXR0916/RG78888 (Genentech), and at a greater level compared to wild type 2B4 and INCAGN01949 (Agenus) antibodies (FIGS. 6A and B).

In the CD3-mediated T cell activation assay, the variant anti-OX40 antibodies induce IFNγ production at a higher level compared to wild type 2B4 and INCAGN01949 antibodies (FIG. 6C). Two of the variant clones, 5A6 and 5G8, induced IFNγ production at a level that is comparable to MOXR0916/RG7888 antibody (FIG. 6C).

Example 7

Figure 8A:
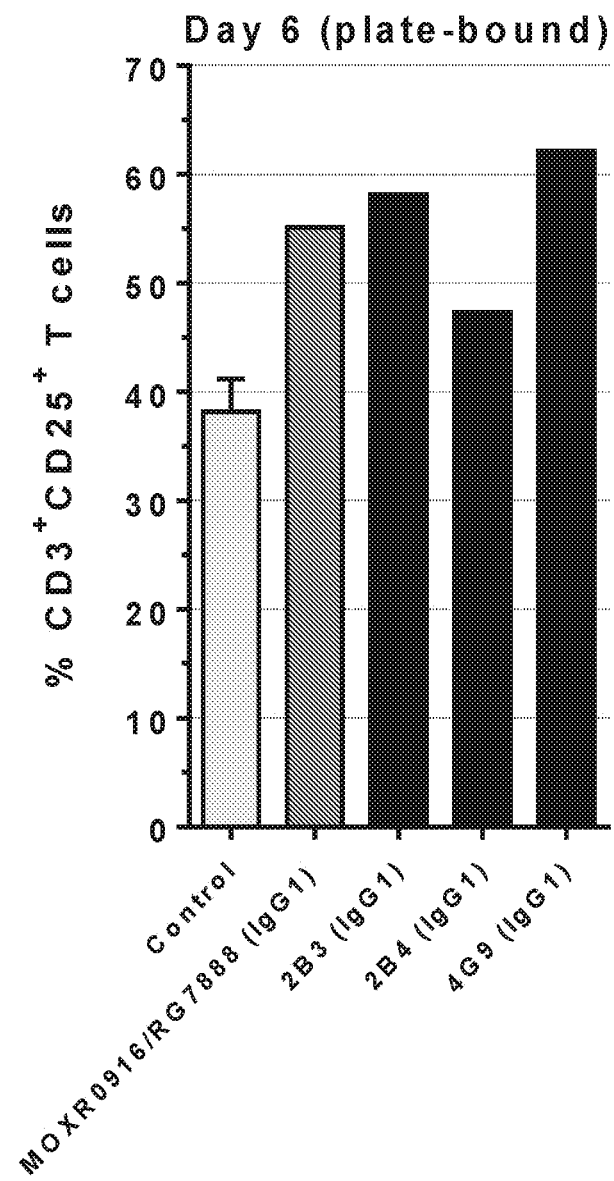
FIG. 8A shows the results of a plate-bound format MLR assay comparing MOXR0916/RG7888, 2B4(WT) and two other clones.
Figure 8B:
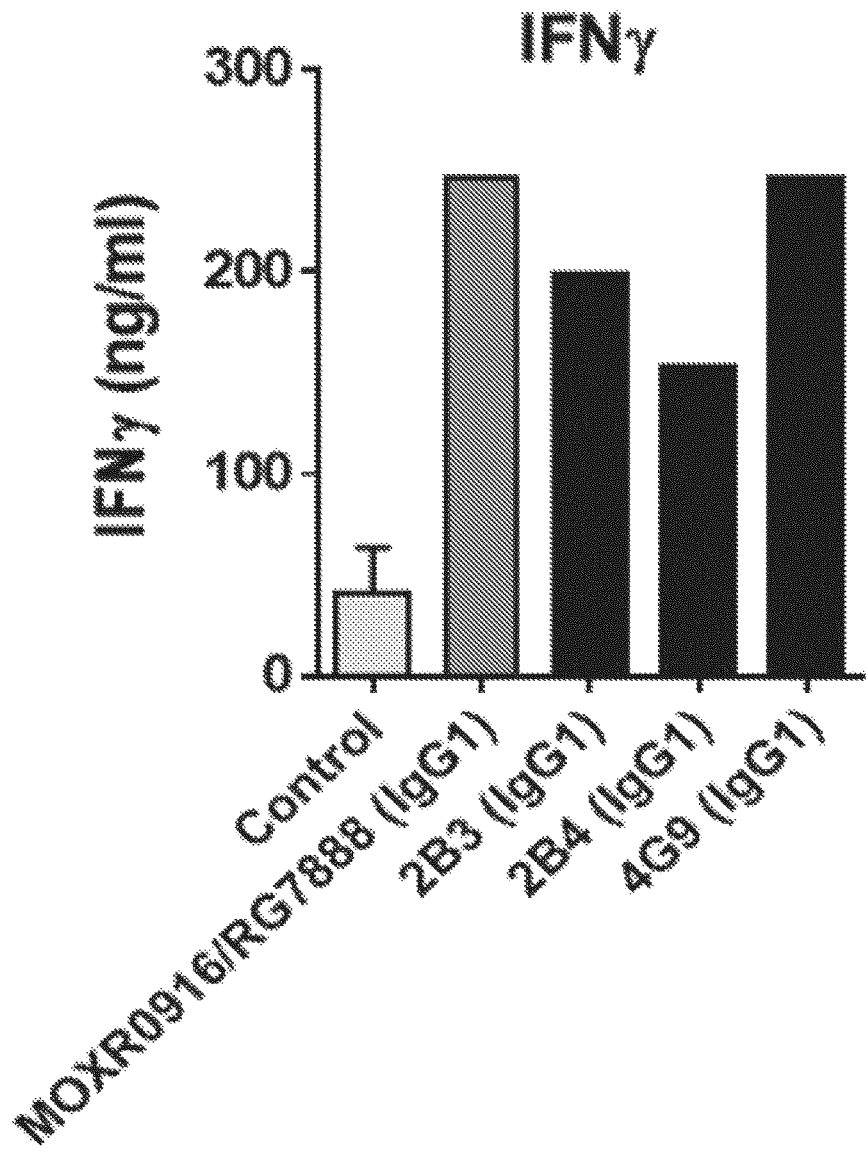
FIG. 8B shows the level of IFNγ detected in a plate-bound format MLR assay comparing MOXR0916/RG7888, 2B4 (WT) and two other clones.
Figure 8C:
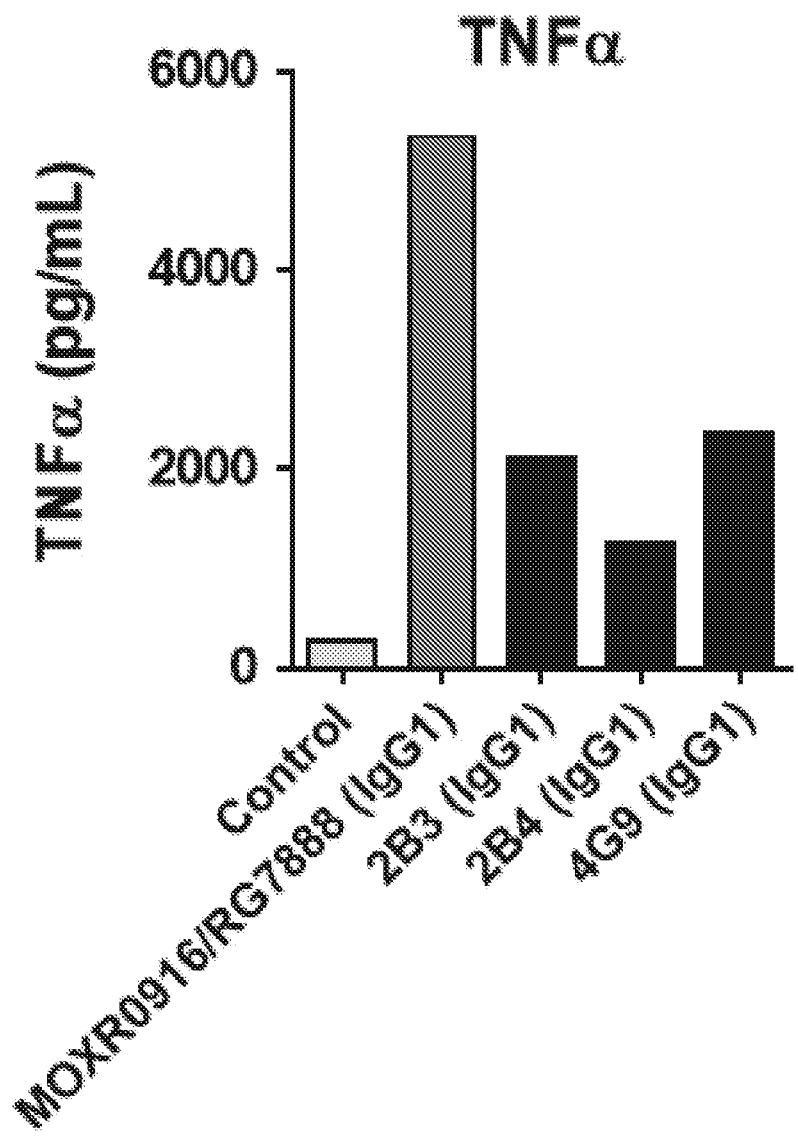
FIG. 8C shows the level of TNFα detected in a plate-bound format MLR assay comparing MOXR0916/RG7888, 2B4(WT) and two other clones.
Figure 8D:
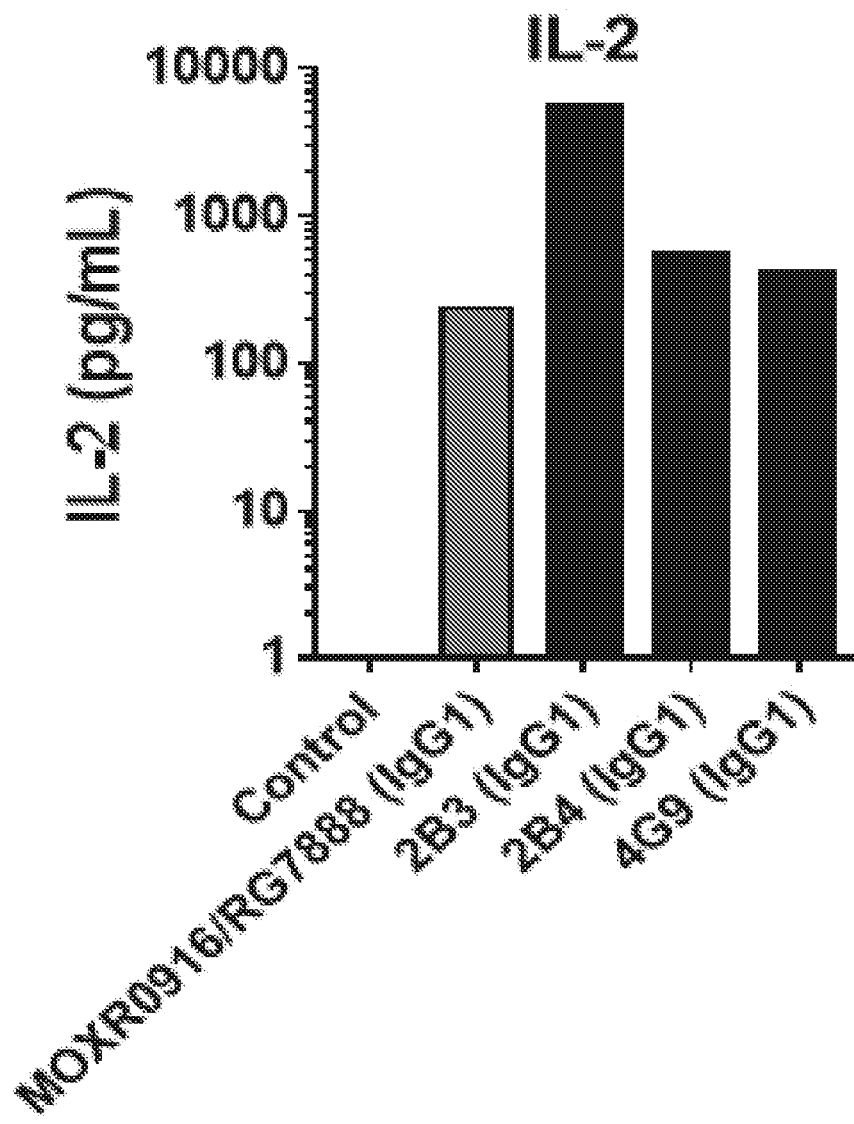
FIG. 8D shows the level of IL-2 detected in a plate-bound format MLR assay comparing MOXR0916/RG7888, 2B4 (WT) and two other clones.
Figure 8E:
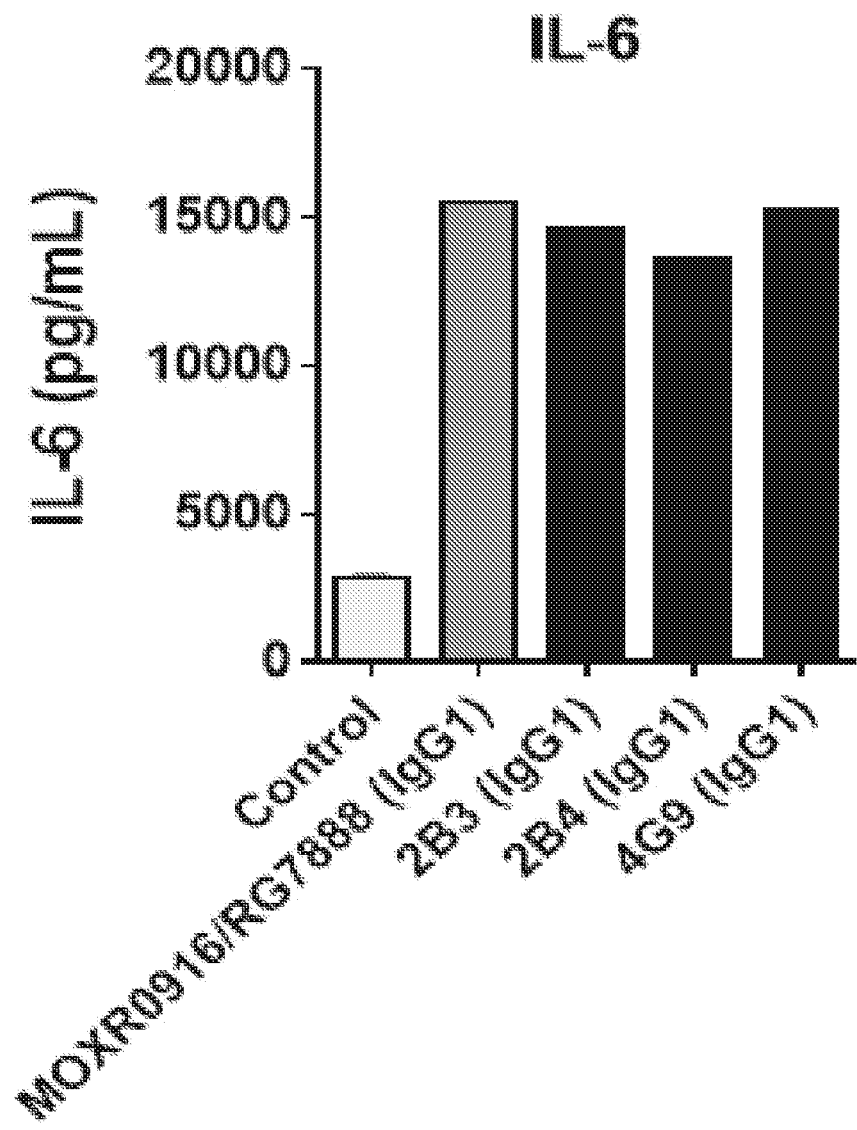
FIG. 8E shows the level of IL-6 detected in a plate-bound format MLR assay comparing MOXR0916/RG7888, 2B4 (WT) and two other clones.
Figure 8F:
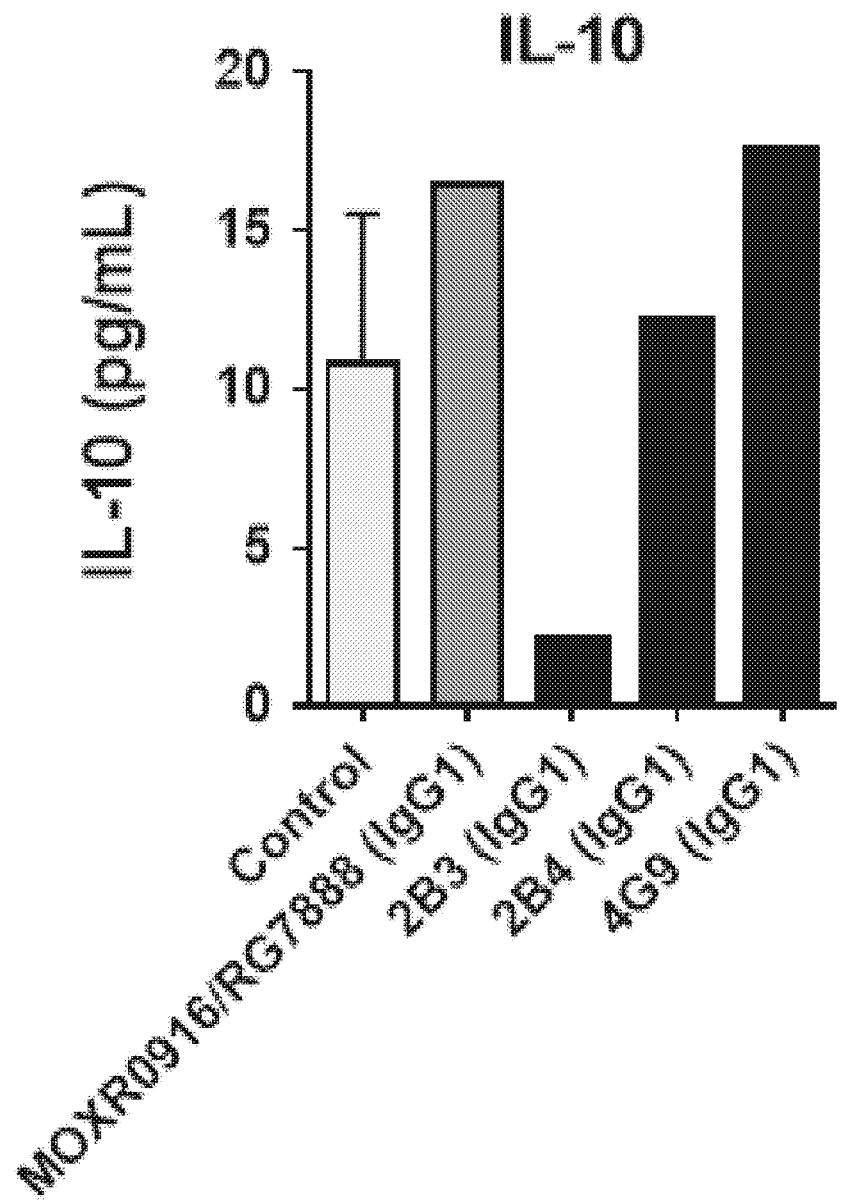
FIG. 8F shows the level of IL-10 detected in a plate-bound format MLR assay comparing MOXR0916/RG7888, 2B4(WT) and two other clones.
Figure 9A:
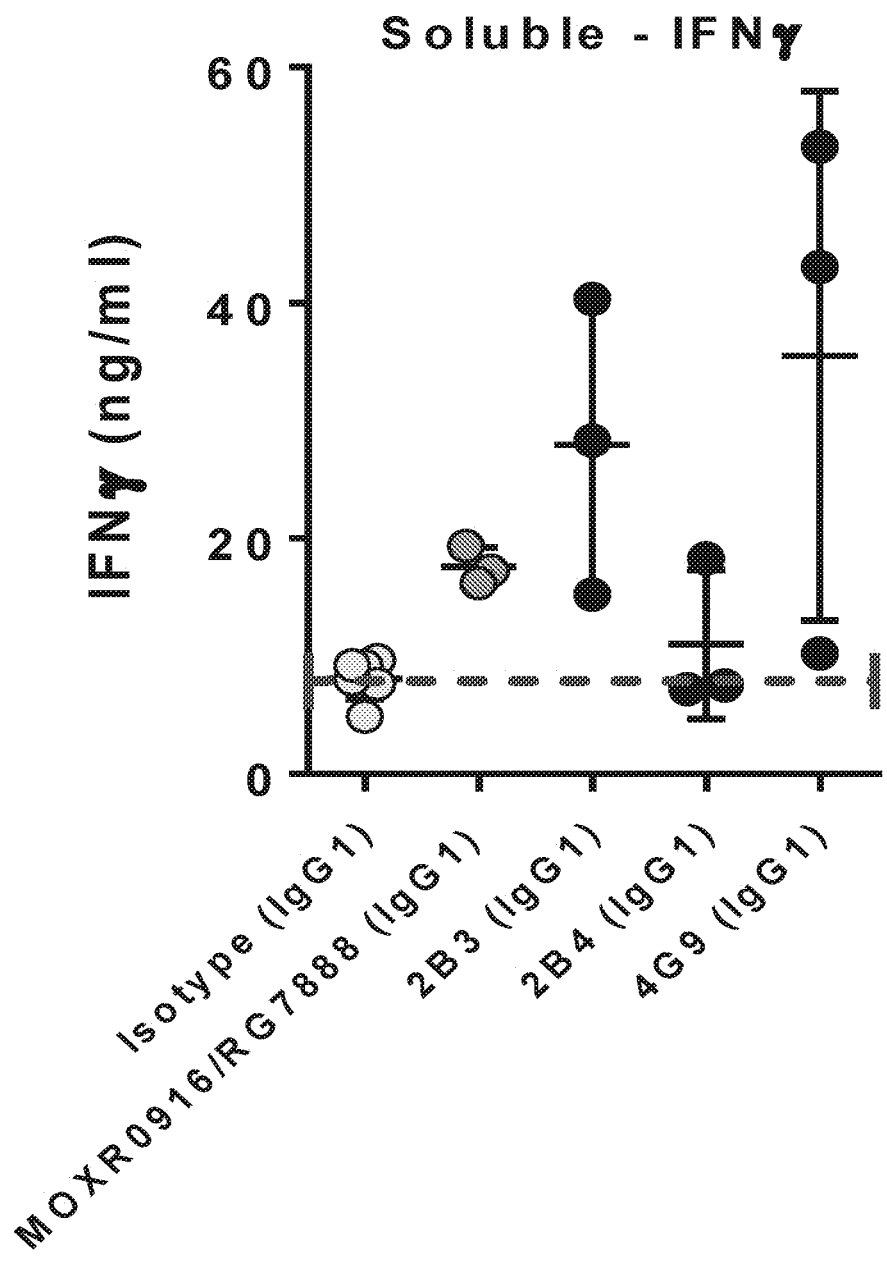
FIG. 9A shows the level of IFNγ detected in a soluble format MLR assay comparing MOXR0916/RG7888, 2B4 (WT) and two other clones.
Figure 9B:
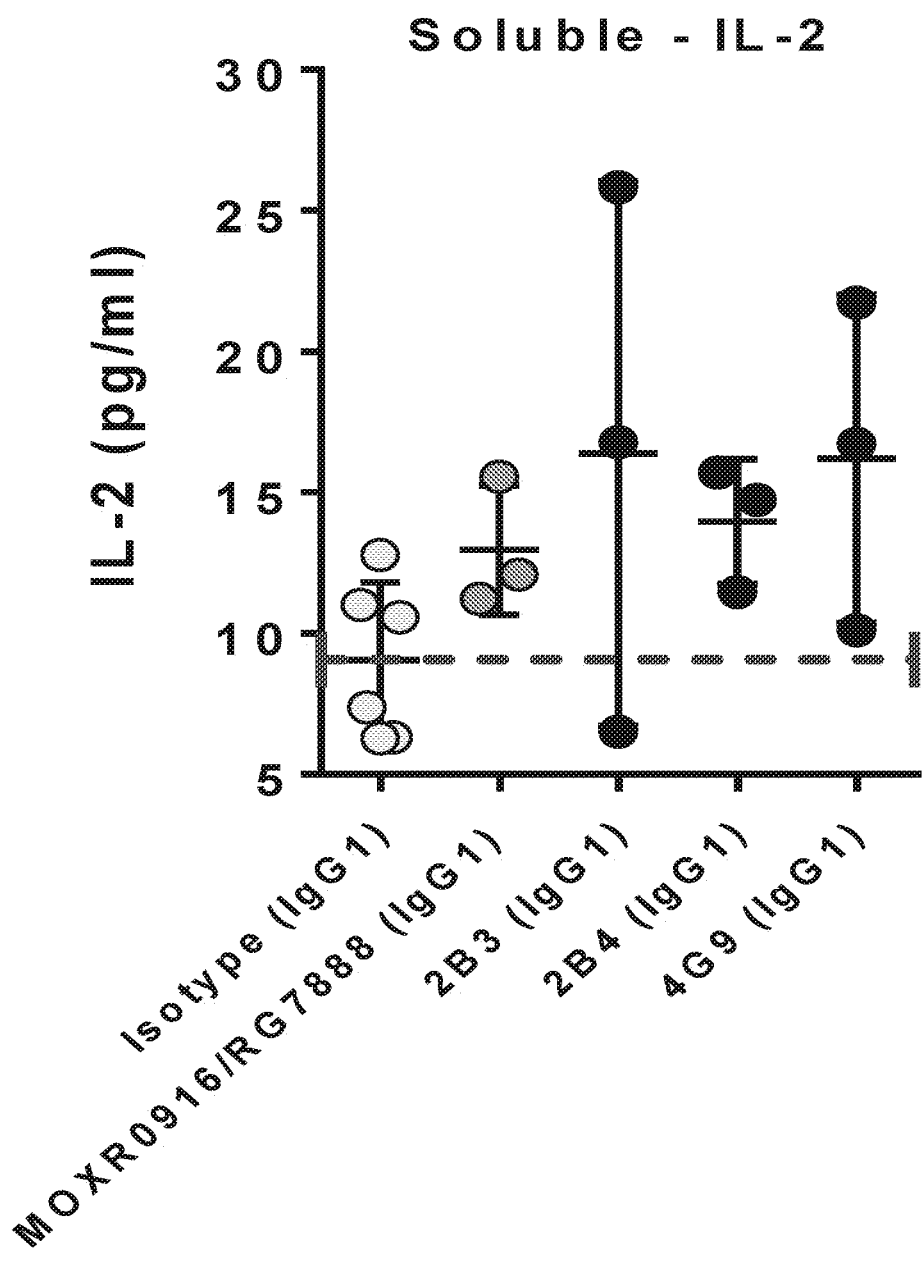
FIG. 9B shows the level of IL-2 detected in a soluble format MLR assay comparing MOXR0916/RG7888, 2B4 (WT) and two other clones.
Figure 9C:
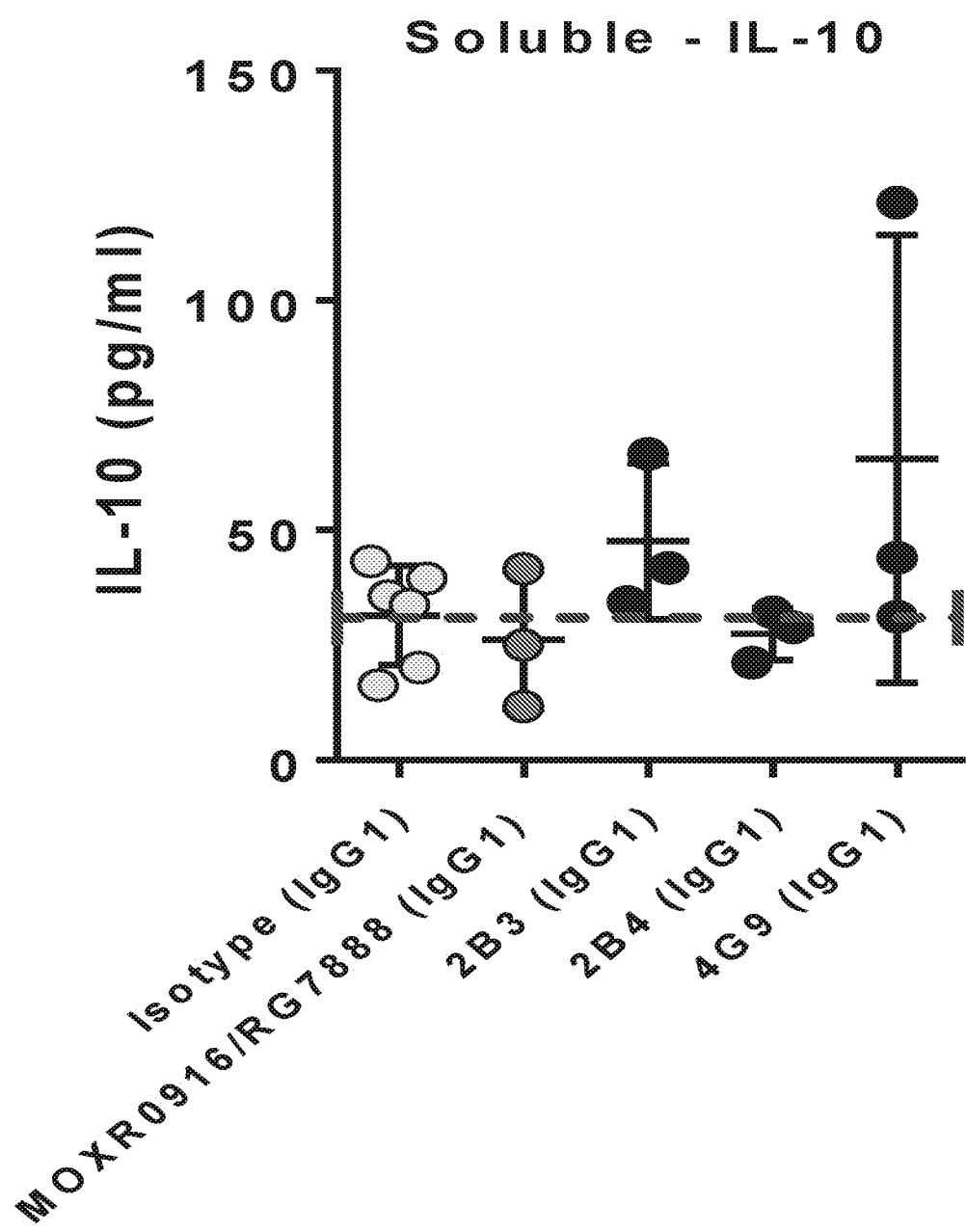
FIG. 9C shows the level of IL-10 detected in a soluble format MLR assay comparing MOXR0916/RG7888, 2B4 (WT) and two other clones.
Figure 9D:
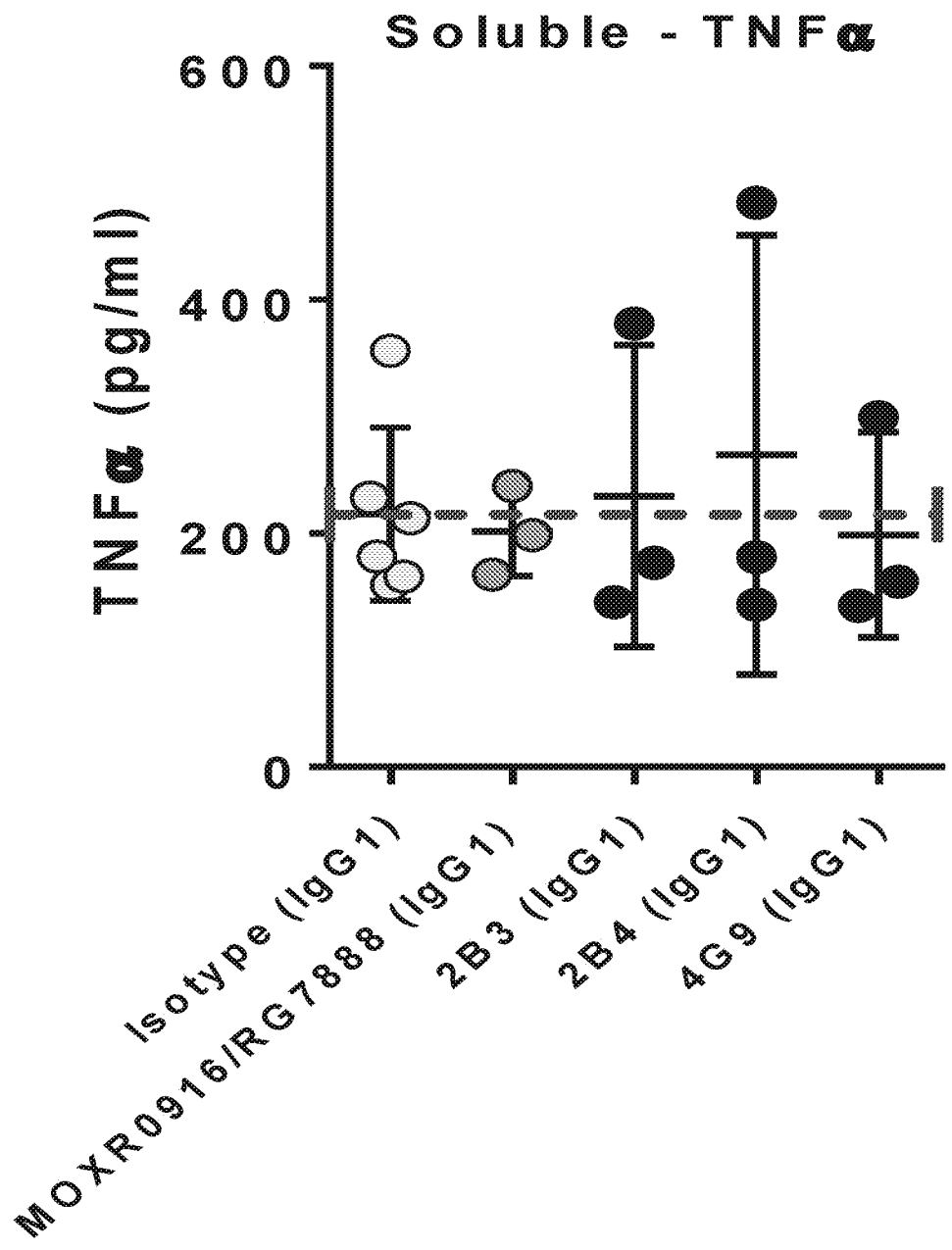
FIG. 9D shows the level of TNFα detected in a soluble format MLR assay comparing MOXR0916/RG7888, 2B4 (WT) and two other clones.

Variant anti-OX40 antibodies were tested for their ability to induce cytokine production using supernatant from a plate-bound 3-way mixed lymphocyte reaction (MLR) assay. The gamma-interferon assays were conducted using wild type 2B4 antibody; variant anti-OX40 antibodies 5A6, 5A8, 5C8, 5G8, 5H6 and 5F5; MOXR0916/RG7888 (Genentech); INCAGN01949 (Agenus); and isotype IgG1 (FIG. 7; samples read at one hour). Supernatants obtained from day six of 3-way MLR assays were analyzed for CD3+ CD25+ T cells (FIG. 8A) and cytokines gamma-interferon, TNFα, IL-2, IL-6 and IL-10 (see FIGS. 8B-F and 9A-D; 6 day samples).

Materials:

Proinflammatory panel 1 (human) kit (Meso Scale Discovery-MSD).

Protocol:

1) Thawed supernatant samples (from T cell activation assay described in Example 6 above) in a sterile cell culture incubator (37° C., 5% CO2).

2) Prepared tubes for standard:

a) Using Calibrator 1 (kit), added 1000 uL of Diluent 2 (kit) to the lyophilized calibrator vial.

b) Inverted at least 3 times (Do Not Vortex).

c) Let the solution equilibrate to room temperature for 15 minutes.

d) Prepared a 1:4 dilution according to kit manual instructions by transferring 100 uL of the highest calibrator to 300 uL of Diluent 2, mixed well. Repeated 4-fold serial dilutions 5 additional times to generate 7 calibrators (vortexed Eppendorf™ tube before transferring the 100 uL) (100 uL calibrator:300 uL diluent 2).

3) Prepared dilution for supernatant samples to 1:10×:

a) In the first round-bottom plate, added 20 uL of supernatant sample to 80 uL of complete media into the wells (1:5× dilution).

b) In a second round-bottom plate, added 50 uL of the 1:5× diluted sample into 50 uL of diluent two into the wells (this dilution is a 1:2× with a final total dilution of samples at 1:10×).

4) Washed the MSD Plate 3 times with 300 uL/well of 1×KPL wash buffer

5) Added 50 uL of standard samples (from step 2) as well as the 1:5× diluted samples (from step 3) (1:5× diluted samples) onto the washed MSD plate.

6) Sealed the plate with an adhesive plate seal and incubated at room temperature with shaking for 2 hours.

7) Prepared the detection antibody solution:
   a) For one plate add 60 μL of SULFO-TAG Anti-hu IFN-γ detection antibody (MSD kit) to 2.94 mL of diluent 3 (total final volume of 3 mL).
8) Without pouring out the samples, washed the plate 3 times with 300 uL/well of 1×KPL wash buffer.
9) Added 25 uL of detection antibody cocktail solution to each well.
10) Sealed the plate with an adhesive plate seal and incubated at room temperature with shaking for 2 hours.
11) Prepared a 2× Read Buffer (prepare a 1:2× dilution of the 4× read buffer in the MSD kit in cell culture grade H2O).
12) Washed the MSD Plate 3 times with 300 uL/well of 1×KPL wash buffer
13) Added 25 uL of read buffer (MSD kit) to each well.
14) Analyzed the plate on an MSD plate reader (waited no more than one hour to read after adding read buffer).

The variant anti-OX40 antibodies induce IFNγ production in at a level comparable to MOXR0916/RG78888 (Genentech), and at a greater level compared to INCAGN01949 (Agenus) and wild type 2B4 as demonstrated in the 3-way mixed lymphocyte reaction assay (plate-bound format) (FIG. 7).

Example 8

Variant anti-OX40 antibodies were tested for their ability to suppress the inhibitory activity of regulatory T cells (Treg). The anti-OX40 suppression assay was conducted using wild type 2B4 antibody; variant anti-OX40 antibodies 5A6 and 5G8; MOXR0916/RG7888 (Genentech); and isotype IgG1 (FIGS. 10A and B).

Materials (for Cell Isolation):
SepMate™-50 isolation tubes (StemCell Technologies).
DPBS 1×+2% FBS (at room temperature, filter sterilize, no sodium azide).
Ficoll-Paque PLUS (GE Healthcare).
EasySep Human CD4+ T-cell Isolation Kit (StemCell Technologies).

Day −1 (Day Minus 1):
1) Diluted αCD3 to 5 μg/mL in 50 uL per well of DPBS 1× and added to a 96-well U-bottom plate.
2) Diluted antibodies to 4 ug/mL in 50 μL per well of DPSB 1× and added to the plate from step 1 (final concentration of αCD3 at 2.5 μg/mL and antibodies at 2 μg/mL in the 100 μL final volume per well).

SepMate™ PBMC Isolation Protocol:
Pipetted 15 mL of the Ficoll density gradient medium through the central hole of the 50 mL SepMate™ insert.
   a) The top of the Ficoll will be slightly above the insert.
   b) Keep bubbles to a minimum.
2) Diluted blood samples 1:10× in room temperature DPBS 1×+2% FBS buffer (for example, for 5 ml of blood, diluted in 145 ml of buffer).
3) Distributed the blood in equal volumes to each SepMate™-50 tube with Ficoll.
   a) Poured into the Sepmate™ tube vertically, slowly down the side of the tube so as to not mix into the Ficoll (take care to not pour the blood/buffer down the center hole of the SepMate™-50 tube).
4) Centrifuged at 1200×g for 10 minutes at room temperature, with the brake on (deceleration of 1).
5) Poured off the top layer, which contained the enriched MNCs (mononuclear cells) into a new tube.
6) Washed enriched MNCs with 20 mL DPBS 1×+2% FBS and centrifuged for 300×g for 8 minutes at room temperature with the brake on.
7) Some red blood cells may be present in the MNC pellet, therefore added approximately 2 mL of 1×RBC lysis buffer per tube for 5 min.
8) Added 10 mL of DPBS 1×+2% FBS to one sample to stop the lysis process, followed by pooling this sample with the remaining samples. Centrifuged at 300×g for 8 minutes.
9) Resuspended the single pooled sample in 20 ml of DPBS 1×+2% FBS and counted the cell concentration.

CD3+ Cell Isolation:
1) Spun cells at 300×g for 8 minutes and resuspended in DPBS 1×+2% FBS at 5×10e7 cells per mL.
2) Added isolation cocktail (from kit) to cell suspension at 50 μL/mL.
3) Mixed and incubated at room temperature for 5 minutes.
4) Vortexed RapidSpheres™ (from kit) for 30 seconds and add to cell suspension+cocktail sample at 50 μL/mL.
5) Topped off volume to 2.5 (or 5 mL) with DPBS 1×+2% FBS and mixed gently by pipetting up and down 2-3 times.
6) Placed the tube without the lid into an EasySep Magnet, incubated at room temperatures for 3 minutes.
7) Picked up magnet and in one continuous motion, inverted the magnet and tube, pouring the enriched cell suspension into a new tube.
8) Spun cells and resuspended cells 20×10e6 cells/ml in FACS buffer and kept on ice.

Materials (Cell Sorting and Plating):
Suppression Assay Complete media: IMDM+5% FBS+1% Human AB Serum.
FACS Buffer: DPBS 1×+2% FBS.
Cell Proliferation Dye eFluor 670 (eBioscience) (stock stored at −20° C.).
(PRE-WARMED) Proliferation Dye Media: PBS+0.5% BSA.
hCD8a-FITC (Biolegend, clone H1T8a).
hCD56-FITC (Biolegend, clone HCD56).
hCD127-APC (Biolegend, clone M-A251).
hCD25-PE (5 ul/1×10e6 cells).

Sorting Protocol:
1) Stained with the following antibodies and kept on ice for 20 minutes:
   a) CD8a-FITC (2 ul/1×10e6 cells)
   b) CD56-FITC (2 ul/1×10e6 cells)
   c) CD127-APC (5 ul/1×10e6 cells)
   d) CD25-PE (5 ul/1×10e6 cells)
2) After staining, washed twice with FACS Buffer.
3) Filtered cells with a 70 μm filter.
4) Resuspended cells at 10×10e6 cells/ml in FACS buffer, kept on ice.
5) Prepared receiving tubes (5 mL FACS tubes) with 600 ul complete media.
6) Using a Fortessa™ Cell Sorter, gated using the following schematic:
   a) Gate out FITC-labeled cells.
   b) Gate on Treg and Teff cells.
7) Kept sorted Treg cells on ice, stain Teff cells with proliferation dye eFlour 670.
8) Resuspended Teff cells from 10×10e6 up to ∼100×10e6 in 1.5 ml of sterile pre-warmed DPBS 1×+0.5% BSA and added 1.5 μl of dye eFluor 670 in DMSO.
9) Mixed by vortexing and incubated in the dark (aluminum foil) for 10 minutes in 37° C. water bath.
10) To quench the staining added 12 ml of ice-cold complete medium, mixed and spun the cells at 1350 RPM for 5 minutes.

11) Washed the cells by resuspending in 12 ml of fresh complete medium, mixed and spun the cells at 1350 RPM for 5 minutes. Proceeded to counting.

Plating Assay: (Final Volume 200 ul/well)
1) Based on the cell count, resuspended the total number of cells needed for the following:
 a) First, plated 30,000 Teff cells in diluted anti-CD28 at 2.5 μg/mL in 100 uL complete media per well.
 b) Second, plated the appropriate number of Teff cells to achieve the Treg to Teff ratio of 1:4 cells in 100 ul/well (without APCs).

2) Spun plate 1000 rpm for 2 min with a low brake.
3) Resuspended cells in 2004, complete media and incubated for 5 days, incubated at 37° C.
4) After 5 days, spun cells and resuspended in FACS buffer, washed twice with 1504, FACS Buffer, and resuspended in final volume of 1504, FACS Buffer.

Two of the variant anti-OX40 antibodies (5A6 and 5G8) promoted the proliferative capacity of Teff cell in the presence of Treg cells at an improved level compared to wild type 2B4 antibody (FIGS. 10A and B).

TABLE list of sequences

| anti-OX40 antibody clone: | Heavy chain variable domain region | Light chain variable domain region |
|---|---|---|
| 2B4 | SEQ ID NO: 1<br>QMQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 2<br>QPVLTQPASVSGSPGQSITI<br>SCTGTSSDLGAYDYVSWYQQ<br>QPGQAPKLIIYDVNNRPSGV<br>SNRFSGSKSGNTASLTISGL<br>QAEDEADYYCSSYTSSSTLV<br>YVFGTGTKVTVL |
| 5-A6 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 3<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTFDTGLV<br>YVFGTGTKVTVL |
| 5-A8 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 4<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTFHTGLV<br>YVFGTGTKVTVL |
| 5-C8 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 5<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTHNTGLV<br>YVFGTGTKVTVL |
| 5-F5 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 6<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTYDTGLV<br>YVFGTGTKVTVL |
| 5-G8 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 7<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTYYTELV<br>YVFGTGTKVTVL |

TABLE-continued list of sequences

| anti-OX40 antibody clone: | Heavy chain variable domain region | Light chain variable domain region |
|---|---|---|
| 5-H6 | SEQ ID NO: 9<br>QVQLVQSGAEVKKPGASVKV<br>SCKTSGYTFTGYYLHWVRQA<br>PGQGLEWMGIINPSDGSTRN<br>AQKFEGRVTMTRDTSTSTVY<br>MELSSLSPEDTAVYYCARDL<br>EYIGSGSLSWFDPWGQGTLV<br>TVSS | SEQ ID NO: 8<br>QSALTQPASVSGSPGQSITI<br>SCTGSSSDIGGYNSVSWYQQ<br>YPGKAPKLIIYDVNNRPSGV<br>SNRFSGSKSGNTASLTISGL<br>QAEDEADYYCSSYTYDNDLV<br>YVFGTGTKVTVL |

I claim:

1. An anti-OX40 antibody, or an antigen binding fragment thereof, that binds to an OX40 epitope, wherein the anti-OX40 antibody or antigen binding fragment thereof comprises a heavy chain variable domain comprising the amino acid sequence of SEQ ID NO. 9, and a light chain variable domain comprising the amino acid sequence of SEQ ID NO 7.

2. The anti-OX40 antibody, or antigen binding fragment thereof, of claim 1, wherein the anti-OX40 antibody is an IgG isotype.

3. The anti-OX40 antibody, or antigen binding fragment thereof, of claim 1, comprising an Fab, an Fab', an F(ab')$_2$, an Fv, a domain antibody, a single chain antibody, a diabody, a triabody, or a tetrabody.

4. The anti-OX40 antibody, or antigen binding fragment thereof, of claim 1, comprising a polypeptide comprising the anti-OX40 antibody or antigen-binding fragment thereof.

5. The anti-OX40 antibody, or antigen binding fragment thereof, of claim 1, wherein the anti-OX40 antibody or antigen binding fragment thereof binds to the OX40 epitope with a $K_d$ less than $1 \times 10^{-8}$ M.

6. A method for inducing proliferation of effector T cells, comprising: contacting the effector T cells with the anti-OX40 antibody, or antigen binding fragment thereof, of claim 1.

7. The method of claim 6 further comprising: detecting an increase in proliferation of the effector T cells.

8. The method of claim 6, further comprising contacting the effector T cells with CD3.

9. The method of claim 6, wherein the effector T cells are CD4+ effector T cells.

10. A method for inducing effector T cells to increase production of at least one cytokine, comprising: contacting effector T cells with the anti-OX40 antibody, or antigen binding fragment thereof, of claim 1.

11. The method of claim 10, further comprising: detecting an increase in production of the at least one cytokine by the effector T cells.

12. The method of claim 10, wherein the at least one cytokine is selected from a group consisting of gamma-interferon, IL-2, IL-4 and tumor necrosis factor (TNF).

13. The method of claim 10, further comprising contacting the effector T cells with CD3.

14. The method of claim 10, wherein the effector T cells are CD4+ effector T cells.

15. A method for inducing proliferation of effector T cells (Teff) in the presence of regulatory T cells (Treg), comprising: contacting the effector T cells and the regulatory T cells with the anti-OX40 antibody, or antigen binding fragment thereof, of claim 1.

16. The method of claim 15, further comprising detecting an increase in proliferation of the effector T cells.

17. The method of claim 15, further comprising contacting the effector T cell and the regulatory T cell with CD3.

18. The method of claim 15, wherein the effector T cells express CD25.

19. The method of claim 15, wherein the effector T cells produce at least one cytokine selected from a group consisting of IL-2, IL-4 and INFγ.

* * * * *

SEQUENCE LISTING

<160> NUMBER OF SEQ ID NOS: 10

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Met Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Ile Ile Asn Pro Ser Asp Gly Ser Thr Arg Asn Ala Gln Lys Phe
    50                  55                  60

Glu Gly Arg Val Thr Met Thr Arg Asp Thr Ser Thr Ser Thr Val Tyr
65                  70                  75                  80

Met Glu Leu Ser Ser Leu Ser Pro Glu Asp Thr Ala Val Tyr Tyr Cys
                85                  90                  95

Ala Arg Asp Leu Glu Tyr Ile Gly Ser Gly Ser Leu Ser Trp Phe Asp
            100                 105                 110

Pro Trp Gly Gln Gly Thr Leu Val Thr Val Ser Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Ala Tyr
            20                  25                  30

Asp Tyr Val Ser Trp Tyr Gln Gln Pro Gly Gln Ala Pro Lys Leu
        35                  40                  45

Ile Ile Tyr Asp Val Asn Asn Arg Pro Ser Gly Val Ser Asn Arg Phe

```
                    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                     85                  90                  95

Ser Thr Leu Val Tyr Val Phe Gly Thr Gly Thr Lys Val Thr Val Leu
                100                 105                 110

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Ile Gly Gly Tyr
                20                  25                  30

Asn Ser Val Ser Trp Tyr Gln Gln Tyr Pro Gly Lys Ala Pro Lys Leu
            35                  40                  45

Ile Ile Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Phe Asp
                     85                  90                  95

Thr Gly Leu Val Tyr Val Phe Gly Thr Gly Thr Lys Val Thr Val Leu
                100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Ile Gly Gly Tyr
                20                  25                  30

Asn Ser Val Ser Trp Tyr Gln Gln Tyr Pro Gly Lys Ala Pro Lys Leu
            35                  40                  45

Ile Ile Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Phe His
                     85                  90                  95

Thr Gly Leu Val Tyr Val Phe Gly Thr Gly Thr Lys Val Thr Val Leu
                100                 105                 110

<210> SEQ ID NO 5
<211> LENGTH: 112
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 5

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Ile Gly Gly Tyr
            20                  25                  30

Asn Ser Val Ser Trp Tyr Gln Gln Tyr Pro Gly Lys Ala Pro Lys Leu
        35                  40                  45

Ile Ile Tyr Asp Val Asn Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr His Asn
                85                  90                  95

Thr Gly Leu Val Tyr Val Phe Gly Thr Gly Thr Lys Val Thr Val Leu
            100                 105                 110

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Ile Gly Gly Tyr
            20                  25                  30

Asn Ser Val Ser Trp Tyr Gln Gln Tyr Pro Gly Lys Ala Pro Lys Leu
        35                  40                  45

Ile Ile Tyr Asp Val Asn Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Tyr Asp
                85                  90                  95

Thr Gly Leu Val Tyr Val Phe Gly Thr Gly Thr Lys Val Thr Val Leu
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Ile Gly Gly Tyr
            20                  25                  30

Asn Ser Val Ser Trp Tyr Gln Gln Tyr Pro Gly Lys Ala Pro Lys Leu
        35                  40                  45

```
Ile Ile Tyr Asp Val Asn Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Tyr Tyr
                 85                  90                  95

Thr Glu Leu Val Tyr Val Phe Gly Thr Gly Thr Lys Val Thr Val Leu
            100                 105                 110
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Ile Gly Gly Tyr
             20                  25                  30

Asn Ser Val Ser Trp Tyr Gln Gln Tyr Pro Gly Lys Ala Pro Lys Leu
         35                  40                  45

Ile Ile Tyr Asp Val Asn Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Tyr Asp
                 85                  90                  95

Asn Asp Leu Val Tyr Val Phe Gly Thr Gly Thr Lys Val Thr Val Leu
            100                 105                 110
```

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Val Gln Leu Val Gln Ser Gly Ala Glu Val Lys Lys Pro Gly Ala
 1               5                  10                  15

Ser Val Lys Val Ser Cys Lys Thr Ser Gly Tyr Thr Phe Thr Gly Tyr
             20                  25                  30

Tyr Leu His Trp Val Arg Gln Ala Pro Gly Gln Gly Leu Glu Trp Met
         35                  40                  45

Gly Ile Ile Asn Pro Ser Asp Gly Ser Thr Arg Asn Ala Gln Lys Phe
         50                  55                  60

Glu Gly Arg Val Thr Met Thr Arg Asp Thr Ser Thr Ser Thr Val Tyr
 65                  70                  75                  80

Met Glu Leu Ser Ser Leu Ser Pro Glu Asp Thr Ala Val Tyr Tyr Cys
                 85                  90                  95

Ala Arg Asp Leu Glu Tyr Ile Gly Ser Gly Ser Leu Ser Trp Phe Asp
            100                 105                 110

Pro Trp Gly Gln Gly Thr Leu Val Thr Val Ser Ser
            115                 120
```

```
<210> SEQ ID NO 10
<211> LENGTH: 249
<212> TYPE: PRT
<213> ORGANISM: Homo sapiens

<400> SEQUENCE: 10

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
        130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
                180                 185                 190

Leu Gly Leu Val Leu Gly Leu Leu Gly Pro Leu Ala Ile Leu Leu Ala
            195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```